(12) United States Patent
Rescigno et al.

(10) Patent No.: US 12,324,820 B2
(45) Date of Patent: *Jun. 10, 2025

(54) USE OF A POSTBIOTIC-BASED COMPOSITION FOR THE TREATMENT OF SKIN DISEASES

(71) Applicant: POSTBIOTICA S.R.L., Milan (IT)

(72) Inventors: Maria Rescigno, Milan (IT); Giuseppe Penna, Milan (IT); Francesca Algieri, Milan (IT)

(73) Assignee: POSTBIOTICA S.R.L., Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/965,469

(22) PCT Filed: Feb. 4, 2019

(86) PCT No.: PCT/EP2019/052665
§ 371 (c)(1),
(2) Date: Jul. 28, 2020

(87) PCT Pub. No.: WO2019/149940
PCT Pub. Date: Aug. 8, 2019

(65) Prior Publication Data
US 2020/0353021 A1 Nov. 12, 2020

(30) Foreign Application Priority Data
Feb. 2, 2018 (IT) .................. 102018000002369

(51) Int. Cl.
| | |
|---|---|
| *A61K 35/747* | (2015.01) |
| *A61K 8/99* | (2017.01) |
| *A61K 35/00* | (2006.01) |
| *A61P 17/06* | (2006.01) |
| *A61P 17/10* | (2006.01) |
| *A61P 17/12* | (2006.01) |
| *C07K 14/335* | (2006.01) |
| *C12N 1/02* | (2006.01) |

(52) U.S. Cl.
CPC .............. *A61K 35/747* (2013.01); *A61K 8/99* (2013.01); *A61P 17/06* (2018.01); *A61P 17/10* (2018.01); *A61P 17/12* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 8,101,167 B2 | 1/2012 | Gueniche | |
| 9,980,991 B2* | 5/2018 | Fasano ................ | A23C 19/032 |
| 10,258,656 B2* | 4/2019 | Fasano ................ | A23L 7/10 |
| 10,729,733 B2* | 8/2020 | Fasano ................ | A61K 35/747 |
| 2011/0206650 A1* | 8/2011 | De Haen ............. | A61K 35/745 |
| | | | 424/93.4 |
| 2012/0087902 A1* | 4/2012 | Rescigno ............. | A61P 1/16 |
| | | | 435/7.1 |
| 2015/0079040 A1* | 3/2015 | O'Neill ............... | A61K 35/747 |
| | | | 424/93.3 |
| 2016/0113973 A1* | 4/2016 | Fasano ................ | A23C 19/032 |
| | | | 424/115 |
| 2017/0065648 A1* | 3/2017 | Fasano ................ | A23L 7/104 |
| 2018/0271920 A1* | 9/2018 | Fasano ................ | A23L 33/40 |
| 2019/0175670 A1* | 6/2019 | Rescigno ............ | A61K 35/747 |
| 2020/0353021 A1* | 11/2020 | Rescigno ............ | A61K 35/747 |
| 2021/0052678 A1* | 2/2021 | Rescigno ............ | A61K 35/747 |
| 2021/0267232 A1* | 9/2021 | Jury .................... | A23K 10/18 |

FOREIGN PATENT DOCUMENTS

| | | | | |
|---|---|---|---|---|
| CA | 3031379 A1 * | 2/2018 | .......... | A61K 35/747 |
| EP | 3493823 A1 * | 6/2019 | .......... | A61K 35/747 |
| FR | 2912917 A1 | 8/2008 | | |
| KR | 10-2004-0006886 A | 1/2004 | | |
| WO | 0228402 A1 | 4/2002 | | |
| WO | 2015012421 A1 | 1/2015 | | |
| WO | WO-2018024833 A1 * | 2/2018 | .......... | A61K 35/747 |
| WO | WO-2019149940 A1 * | 8/2019 | .......... | A61K 35/747 |
| WO | WO-2019149941 A1 * | 8/2019 | ............ | A23K 10/12 |
| WO | WO-2020006663 A1 * | 1/2020 | | |
| WO | WO-2020216863 A1 * | 10/2020 | ............ | C12N 1/205 |

OTHER PUBLICATIONS

Ashraf et al, Critical Reviews in Food Science and Nutrition. 2014. 54:7, 938-956 . . . published online: Feb. 5, 2014. (Year: 2014).*
Amiri et al, Scientific Reviews, 2021. 10.2478/AMB-2021-0015. 6 pages. (Year: 2021).*
Kump et al. Inflamm. Bowel Dis. 19: 2155-2165, 2013.*
Mahmud et al. Gut Microbes 14: e2096995-1 to e2096995-29, 2022.*
"Shocking Super Extract Essence", Database GNPD [Online] Mintel, 2017,XP055507896, pp. 1-4.

(Continued)

*Primary Examiner* — S. Devi

(74) *Attorney, Agent, or Firm* — Lucas & Mercanti, LLP

(57) ABSTRACT

The present invention refers to a composition including a fermented supernatant of *Lactobacillus casei* or *paracasei* species The species is characterized by having in its DNA genome at least one DNA sequence essentially identical to one of the sequences selected from the group consisting of: SEQ ID No 1 to 5, and proper diluents and/or carriers and/or excipients. The compositions can be used in the treatment and/or prevention of skin and/or dermatological diseases related to inflammation, allergic reactions, contact hypersensitivity reactions and intolerance, excessive sebaceous secretion, exfoliation or microbial dysbiosis, preferably of the epidermis.

Figure 1:
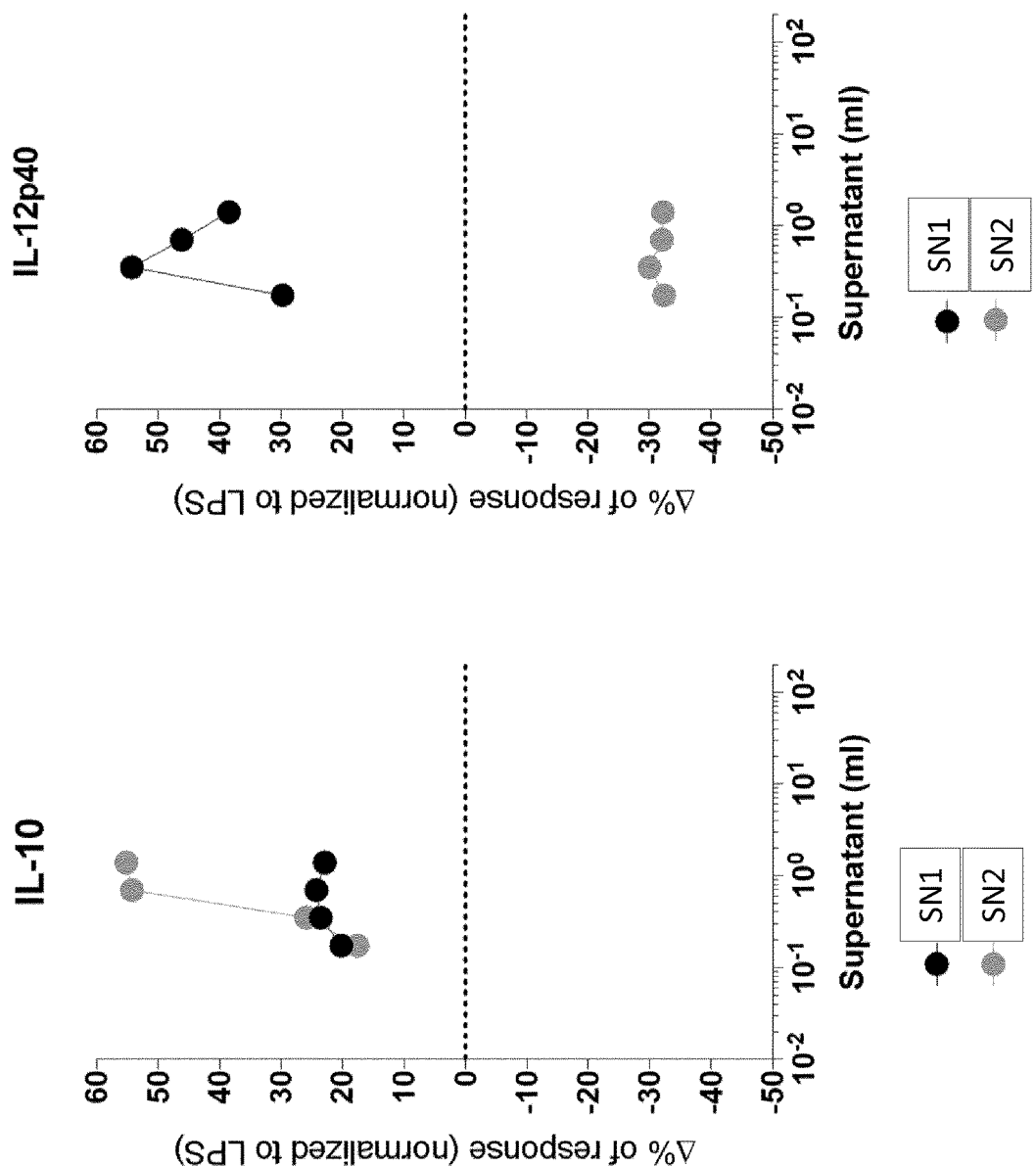

16 Claims, 6 Drawing Sheets
Specification includes a Sequence Listing.

(56) References Cited

OTHER PUBLICATIONS

"Active Hydrating Milk", Database GNPD [Online] Mintel, 2011, XP055507876, pp. 1-3.
Makarova et al., "Comparative genomics of the lactic acid bacteria", Proceedings of the National Academy of Sciences, 2006, vol. 103, No. 42, pp. 15611-15616.
Mileti et al., "Comparison of the Immunomodulatory Properties of Three Probiotic Strains of Lactobacilli Using Complex Culture Systems: Prediction for In Vivo Efficacy", PLOS ONE, 2009, vol. 4, No. 9, pp. 1-16.
Broadbent et al., "Influence of polysorbate 80 and cyclopropane fatty acid synthase activity on lactic acid production by Lactobacillus casei ATCC 334 at low pH", Journal of Industrial Microbiology and Biotechnology, 2013, vol. 41, No. 3, pp. 545-553.
International Search Report and Written Opinion for Corresponding International Application No. PCT/EP2019/052665 (Apr. 26, 2019) (17 Pages).
Search Report for Corresponding Italian Application No. 201800002369 (Sep. 25, 2018) (11 Pages).
EPO, Office Action issued for European Patent Application No. 19705930.6, dated Jun. 29, 2023, 12 pages.
C. C. Sieo, et al., "Effect of prebiotic oligosaccharides on growth of Lactobacillus strains used as a probiotic for chickens," 2011, African Journal of Microbiology Research, vol. 5 n. 1, p. 57-64.
C.E. Rycroft, et al., "A comparative in vitro evaluation of the fermentation properties of prebiotic oligosaccharides," 2001, Journal of Applied Microbiology, vol. 91 n. 5, p. 878-887.
Siok-Koon Yeo, et al., "Effect of prebiotics on viability and growth characteristics of probiotics in soymilk," 2010, Journal of the Science of Food and Agriculture, vol. 90 n. 2, p. 267-275.

* cited by examiner

USE OF A POSTBIOTIC-BASED COMPOSITION FOR THE TREATMENT OF SKIN DISEASES

CROSS-REFERENCE TO RELATED APPLICATIONS

This application is a 371 of PCT/EP2019/052665, filed Feb. 4, 2019, which claims the benefit of Italian Patent Application No. 102018000002369, filed Feb. 2, 2018.

FIELD OF INVENTION

The invention refers to a fermented product obtained from *Lacatobacillus casei o paracasei* species, able to significantly reduce, in a dose dependent manner, IL-6 and IL-8 cytokines, chemotactic factor CCL2/MCP1 and long isoform "lfTSLP" (inflammatory) levels and increase the level of short isoform "sfTSLP" (homeostatic), in eukaryotic cells exposed to inflammatory stimuli, in particular epidermal cells, more in particular human keratinocytes. Said fermented product finds application in a variety of dermatological and cosmetic applications.

BACKGROUND OF THE INVENTION

The skin is considered the organ with the largest surface of our body. It covers a protective, sensorial, secretory, thermoregulatory, absorption, permeability and aesthetic action. In utero, the skin is considered sterile and only after birth, the environmental microbial communities begin colonization of the stratum corneum, and evolving into a complex microbial ecosystem, which is actively involved in the formation and in the maintenance of cutaneous homeostasis and of a correct inflammatory response (Dominguez-Bello et al., 2010) (Capone et al., 2011). The complexes of microbes present on the skin surface, whether resident or transient, are called skin microbiota (Cho and Blaser, 2012). The interaction between host and microbiota is fundamental for the development and maintenance of the symbiotic status. The bioactive molecules derived from the bacteria metabolism during the fermentation process, called postbiotics, constitute the molecular signals underlying this interaction. In some pathological conditions the dysbiosis of the cutaneous microbiota, can contribute to immunological homeostasis breaking thus amplifying the symptoms of the disease (Kong et al., 2012) (Naik et al., 2012). Modifications of the cutaneous microbiota have been associated with the rising of allergies and chronic inflammatory epidermal diseases (Ehlers et al., 2010). The immune response of the skin, in particular the production of cytokines by epidermal keratinocytes, is influenced by cutaneous microbiota, as shown by the significant increase in "germ free" mice, devoid of microbiota, of the cytokine Thymic Stromal Lymphopoietin (TSLP) (Yockey et al., 2013). The TSLP protein is an immunological mediator, involved both in multiple immunological diseases (Ziegler, 2012) (Siracusa et al., 2011) and in the maintenance of immunological tolerance (Watanabe et al., 2005) (Hanabuchi et al., 2010). The identification of two distinct forms of TSLP, the long (lfTSLP) and short (sfTSLP) form and their functional characterization have shed light on the opposite biological functions of the molecules. The lfTSLP exerts a pathogenic role and is induced by inflammatory stimuli while the sfTSLP is released constitutively and exerts an anti-inflammatory and homeostatic role (Fornasa et al., 2015). The imbalance of the 2 isoforms, favoring the inflammatory form lfTSLP has been identified in skin diseases such as atopic dermatitis (Fornasa et al., 2015). The release of inflammatory mediators, such as IL-6, IL8, CCL2/MCP1 and inflammatory TSLP (lfTSLP), by skin keratinocytes, is the basis for multiple skin diseases (Jang et al., 2013) (Wilson et al., 2013) (Schaper et al., 2016) (Volpe et al., 2014). In particular, human epidermal keratinocytes express the inflammatory form of TSLP (lfTSLP), only in response to inflammatory stimuli such as polyinosinic: polycytidylic acid (poly I: C) or invasive bacteria such as *Salmonella Typhimurium*, while constitutively release the homeostatic form of TSLP (sfTSLP), which is reduced by pathogenic bacteria (*Salmonella typhimurium*) and increased by anti-inflammatory agents such as vitamin D3 (Fornasa et al., 2015). Furthermore, the sfTSLP form exerts an antibacterial activity, through the modulation of the microbiota, favoring the skin protective action (Bjerkan et al., 2015).

Probiotics and Postbiotics

Probiotics are defined as live microorganisms that exert beneficial effects on the host when administered in adequate amounts. Probiotics are in general isolated from fecal samples of healthy individuals, mostly from breast-fed infants. The microbiota may belong to either symbiotic or pathobiont classes of microorganisms and may have divergent immunomodulatory properties. Different strains, even among the same species, may have opposing effects, as has been shown in a number of studies (Kaci et al., 2011; Van Hemert et al., 2010). Furthermore, recent data suggest that certain beneficial effects observed after the administration of probiotics may be mediated by molecules or factors produced and secreted by the bacteria into the gut lumen, henceforth herein called postbiotics (or "fermented product" or "fermented supernatant"). In the context of the present invention, for postbiotic is intended any factor resulting from the metabolic activity of a probiotic or any released molecule capable of conferring beneficial effects to the host in a direct or indirect way.

*Lactobacillus paracasei* Supernatant

The putative therapeutic use of strains of *Lactobacillus paracasei* strain CNCM I-1390 (Budapest Treaty deposit), redeposited by IEO—Istituto Europeo di Oncologia S.r.l., Via dei Filodrammatici 10, 20121 Milano, on Jul. 26, 2017, according to Budapest Treaty, with CNCM (Collection Nationale de Cultures de Microorganismes, Institut Pasteur, 25,28 rue du Docteur Roux 75724 Paris CEDEX 15, FR) with the no. 1-5220 (hereinafter also named as B21060), in particular of the fermentation supernatant thereof as an anti-inflammatory in intestinal diseases, is described in WO 2011/009848 A2.

It is still felt the need of a postbiotic, able to prevent or treat dermatological diseases.

DESCRIPTION OF THE INVENTION

The inventors have found that the metabolic products or the supernatant (herein both and/or together defined as "fermented product") by *Lactobacillus Paracasei* strain CNCM I-5220, of Institute Pasteur collection, is able to modulate keratinocyte activation, favouring the inflammatory response, the epidermal and cutaneous microbiota homeostasis. The present invention relates to the use of a formulation containing the postbiotic generated by bacterial strain *Lactobacillus Paracasei* CNCM I-5220 fermentation, in pathological epidermal manifestation such as psoriasis, atopic and contact dermatitis, eczema, rosacea, acne, surgical scars and sunburn, itching, cold sores and dry skin (senile xerosis, asteatosis).

It is therefore object of the present invention a composition comprising a fermented supernatant (or fractions thereof) of *Lactobacillus casei* or *paracasei* species, said species being characterized by comprising in its DNA genome at least one DNA sequence essentially identical to one of the sequences selected from the group consisting of: SEQ ID No 1 to 5, and proper diluents and/or carriers and/or excipients for use in the treatment and/or prevention of skin and/or dermatological diseases related to inflammation, allergic reactions, contact hypersensitivity reactions and intolerance, excessive sebaceous secretion, exfoliation or microbial dysbiosis (modification of the microbiota composition), preferably of the epidermis. Said pathology is preferably selected from the group consisting of: psoriasis, contact and atopic dermatitis, eczema, rosacea, acne, surgical scars and sunburn, itching, cold sores, dry skin (e.g. xerosis senile, asteatosis), greasy or itchy dandruff, trichodynia, seborrheic dermatitis.

Said fermented supernatant is preferably obtainable by a method characterized by the fermentation of said *Lactobacillus casei* or *paracasei* species in a minimum solution additioned with a lactate salt, preferably sodium lactate, calcium lactate, potassium lactate.

Preferably, said minimum solution is a solution which does not contain carbon and/or nitrogen sources or micromolar concentration of minerals (e.g. iron, sulfur etc.), more preferably it is saline, phosphate buffer, H2O, a minimum isotonic solution or a hypotonic solution.

Preferably, said method comprises two fermentations of said *Lactobacillus casei* or *paracasei* species into a minimum solution, at least one of which is carried out into a minimum solution additioned with a lactate salt, preferably sodium lactate, calcium lactate, potassium lactate.

In a preferred embodiment of the invention said second fermentation is carried out at a temperature of 0° C.-10° C., preferably of 4° C.

Preferably, said fermented supernatant is a dry powder, e.g. obtained by lyophilization, freeze-drying, granulation, spray drying.

Preferably, the fermented supernatant comprises:
a) after a first fermentation into a minimum solution:
oleic acid and/or decanoic acid and/or benzopropanoic acid and/or citric acid, preferably in the following concentration:
oleic acid: 3-9 mg/L, preferably 4-8 mg/L, more preferably about 7.98 mg/L; and/or
decanoic acid: 1-3 mg/L, preferably about 1.30 mg/L; and/or
benzopropanoic acid: 1-4 mg/L, preferably 2-3 mg/L; more preferably about 2.69 mg/L and/or
citric acid: 10-15 mg/L, preferably 12-14 mg/L; more preferably about 13.05 mg/L.
and/or
b) after a second fermentation into a minimum solution additioned with a lactate salt, preferably sodium lactate:
7 hexadecenoic acid and/or tridecanoic acid and/or vaccenic acid and/or oleic acid, preferably in the following concentration:
7 hexadecenoic acid: 2-6 mg/L; 5-6 mg/L; about 5.12 mg/L; and/or
tridecanoic acid: 2-6 mg/L; 5-6 mg/L; about 5.42 mg/L; and/or
vaccenic acid: 10-15 mg/L; preferably 12-14 mg/L; more preferably about 12.23 mg/L and/or
oleic acid: 3-5 mg/L, preferably 3-4 mg/L, more preferably about 3.21 mg/L.

More preferably, the fermented supernatant comprises after a first fermentation into a minimum solution:
oleic acid, decanoic acid, benzopropanoic acid, citric acid, in the following concentration:

|  | mg/L |
|---|---|
| oleic acid | 7.98 |
| decanoic acid | 1.30 |
| benzopropanoic acid | 2.69 |
| citric acid | 13.05 |

More preferably, the fermented supernatant comprises after a second fermentation into a minimum solution additioned with a lactate salt, preferably sodium lactate: 7 hexadecenoic acid and tridecanoic acid and vaccenic acid and oleic acid, in the following concentration:

|  | mg/L |
|---|---|
| 7 hexadecenoic acid | 5.12 |
| tridecanoic acid | 5.42 |
| vaccenic acid | 12.23 |
| oleic acid | 3.21 |

Preferably, the fermented supernatants, when analyzed by MALDI TOF mass spectrometry, are characterized by the peptide signal profile of Table 2A.

Preferably, the fermented supernatant after two fermentations of said *Lactobacillus casei* or *paracasei* species into a minimum solution, at least one of which is carried out into a minimum solution additioned with a lactate salt (such as sodium lactate), when analyzed by MALDI TOF/TOF mass spectrometry, is characterized by the peptide signal profile of Table 2B.

Preferably, the fermented supernatant after two fermentations of said *Lactobacillus casei* or *paracasei* species into a minimum solution, at least one of which is carried out into a minimum solution additioned with sodium lactate, is characterized by comprising at least one of the peptides of SEQ ID NO: 19-41.

Said fermented supernatant is preferably obtainable by a method comprising the following steps:
a) growing an inoculum of *Lactobacillus* strain as defined above in a suitable culture medium, at a temperature ranging from 4 to 40° C., preferably of 37° C., to obtain a biomass and allowing fermentation of said biomass into a minimum solution to proceed for 12 to 36 hours, preferably for about 24 hours, to get a fermented biomass;
b) centrifuging said fermented biomass to get a pellet of fermented biomass and a first fermented product;
c) incubating said pellet of fermented biomass into a minimum solution for 12 to 36 hours, preferably for about 24 hours, at a temperature ranging from 4 to 40° C., preferably ranging from 4 to 20° C., more preferably of 4° C., to obtain a further fermented biomass;
d) separating said further fermented biomass from a second fermented product by centrifugation.

Preferably, one of the minimum solutions from step a) and c) comprises a lactate salt, such as sodium lactate, preferably the minimum solution of step c) comprises a lactate salt, such as sodium lactate.

First and/or second fermented product obtainable from step b) or d) respectively are used in the invention and collectively will be defined as "fermented product". They may be used as active ingredients for the composition and formulation accordingly to the invention, either individually or combined. In a preferred embodiment of the invention, the fermented supernatant is the product obtainable from step d), more preferably obtainable by a method wherein only the minimum solution of step c) comprises a lactate salt, such as sodium lactate. The minimal solution of step a) and c) is for example a saline solution, phosphate buffer, H$_2$O, etc.

In the present invention the above species is preferably characterized by comprising in its DNA genome DNA sequences essentially identical to SEQ ID No 1-5.

Preferably, the *Lactobacillus* species is *Lactobacillus paracasei*, more preferably a strain characterized by comprising in its DNA genome at least one DNA sequence essentially identical to sequences SEQ ID No 6-18. Preferably said strain comprises in its DNA genome DNA sequences essentially identical to SEQ ID No 6-18.

Preferably, the *Lactobacillus paracasei* is the strain deposited according to Budapest Treaty with no. CNCM I-5220.

The strain B21060 (or CNCM I-5220) was deposited under the Budapest Treaty at Collection Nationale de Cultures de Microorganismes (CNCM), with number CNCM I-5220 on 26 Jul. 2017 (deposit information:
  Microorganism Deposit Accession No.: CNCM I-5220;
  Depositary Institution name: Collection nationale de cultures de microorganismes (CNCM));
  Depositary Institution address: Institut Pasteur, 25 Rue du docteur Roux, 75724 Parise Cedex 15, France;
Deposit Date: 26 Jul. 2017
  Name and Address of Depositor: IEO—Istituto Europeo di Oncologia S.r.l., Via Filodrammatici 10, 20121 Milano, Italy).

In a preferred embodiment, the composition further comprises at least one adjuvant and/or other therapeutic agents.

Preferably, the composition according to the invention is in a formulation for topical administration, preferably selected from the group consisting of: cream, emulsion, dispersion, gel, ointment, lotion, serum.

In the composition as above defined, the fermented product is preferably present at 0.1-1% w/w. A further object of the invention is the cosmetic use of the composition as defined above, preferably to prevent and/or reduce the signs of skin aging, skin imperfections, hyperhidrosis and for hair care. The composition for use according to the invention is preferably a pharmaceutical composition. The composition according to the present invention may further comprises at least one adjuvant and/or other therapeutic agents.

Preferably, the above defined species are characterized by at least one of the gene selected from the group consisting of SEQ ID NO. 1-5 and/or by at least one of the gene selected from the group consisting of SEQ ID NO. 6-8 and/or by at least one of the genome DNA sequences selected from the group consisting of SEQ ID NO:9-18. Preferably, the above defined species are characterized by the genes having the sequences essentially identical to SEQ ID NO. 1-5. Preferably, the above defined species are characterized by the genes having the sequences essentially identical to SEQ ID NO. 6-8. Preferably, the above defined species are characterized by genome DNA sequences essentially identical to SEQ ID NO:9-18. In the context of the present invention, for postbiotic is intended the supernatant or any factor resulting from the metabolic activity of a probiotic or any released molecule capable of conferring beneficial effects to the host in a direct or indirect way. Therefore, the term "postbiotic", "fermented product" or "fermented supernatant" in the context of the present invention may comprise also any factor resulting from the metabolic activity of a probiotic or any released molecule capable of conferring beneficial effects to the host in a direct or indirect way. In the context of the present invention the term "fermented product" and "fermented supernatant" are exchangeable. In the context of the present invention the fermented supernatant also comprises any factor resulting from the metabolic activity of a probiotic or any released molecule capable of conferring beneficial effects to the host in a direct or indirect way. The preferred supernatant of the invention is a postbiotic product obtained by the fermentation of *L. paracasei* CNCM I-5220 and does not contain food and live bacteria. Said preferred embodiment is preferably lyophilized. In the context of the present invention "the solution supernatant" or the "fermented supernatant" may be also defined as "fermented product" and may also include fractions thereof and/or metabolic components thereof. The fermented product according to the invention is preferably obtained at a non-canonical fermentation temperature. The fermentation product used in the present invention may be obtained through the fermentation of different substrates such as sodium lactate or prebiotic ingredient (GOS, FOS, etc), plant extracts (e.g. Aloe, chamomile, mallow, *Echinacea*). The fermented product or composition according to invention may be lyophilized according to any method known to the skilled in the art. The fermented supernatant may be a dry powder, e.g. obtained by lyophilization, freeze-drying, granulation, spray drying. The pharmaceutical composition according to the invention is formulated to be administered to a subject in a therapeutically effective amount, depending on the type of subject, severity of the disease and route of administration. Typically, the therapeutically effective amount of the fermented product is about 0.01-10 mg/day, preferably 1 mg/day. The administration is e.g. carried out with 1-2 administrations/die of 0.5-5 g of fermented product or composition as defined above, at the concentration of 0.01-5% by weight of the final composition. In a further preferred embodiment, the composition comprises at least an additional ingredient, preferably selected from vitamin C, vitamin C derivatives, vitamin E, vitamin E derivatives, tocopherols, vitamin A, vitamin A derivatives, retinal, retinoic acid, vitamin D3, Vitamin K, Vitamin B1, B3, B5, B6, B12 and chemical elements such as zinc or essential amino acids, prebiotic ingredients and plant extracts (echinacea, mallow, chamomile, aloe, etc.) In the context of the present invention, the term fermented supernatant also comprises fractions thereof. In the context of the present invention, when referring to specific DNA sequences, it is intended that it is comprised within the invention also RNA molecules identical to said polynucleotides, except for the fact that the RNA sequence contains uracil instead of thymine and the backbone of the RNA molecule contains ribose instead of deoxyribose, RNA sequence complementary to the sequences herein disclosed, functional fragments, mutants and derivatives thereof, proteins encoded therefrom, functional fragments, mutants and derivatives thereof. The term "complementary" sequence refers to a polynucleotide, which is non-identical to the sequence, but either has a base sequence to the first sequence complementary or encodes the same amino acid sequence as the first sequence. A complementary sequence may include DNA and RNA polynucleotides. The term "functional" or "functional" may be understood as capable of maintaining the same activity. "Fragments" are preferably long at least 10 aa., 20 aa., 30 aa., 40 aa., 50 aa., 60 aa., 70 aa., 80 aa., 90 aa., 100 aa., 150 aa., 200 aa., 300 aa., 400 aa., 500 aa., 600 aa., 700 aa., 800 aa., 900 aa., 1000 aa., 1200 aa., 1400 aa., 1600 aa., 1800 aa. or 2000 aa. "Derivatives" may be recombinant or synthetic. The term "derivative" as used herein in relation to a protein means a chemically modified protein or an analogue thereof, wherein at least one substituent is not present in the unmodified protein or an analogue thereof, i.e. a protein that has been covalently modified. Typical modifications are amides, carbohydrates, alkyl groups, acyl groups, esters and the like. As used herein, the term "derivatives" also refers to longer or shorter polynucleotides/proteins and/or having e.g. a percentage of identity of at least 85%, 86%, 87%, 88%, 89%, 90%, 91%, 92%, 93%, 94%, 95%, 96%, 97%, 98%, more preferably of at least 99% with the sequences herein disclosed. In the present invention "at least 70% identity" means that the identity may be at least 70%, or 75%, or 80%, or 85% or 90% or 95% or 100% sequence identity to referred sequences. This applies to all the mentioned % of identity. Preferably, the % of identity relates to the full length of the referred sequence. Sequence alignment to determine percental sequence identity may be determined according to any method known to the skilled in the art, for example using public domain software such as BLAST, BLAST-2, ALIGN o Megalign (DNASTAR) software. In the context of the present invention a carrier may be any vehicle or composition involved in delivery of the fermented product into the subject or that facilitate the storage of the composition. The present invention finds application in the treatment of humans and in veterinary. The derivative of the invention also includes "functional mutants" of the polypeptides, which are polypeptides that may be generated by mutating one or more amino acids in their sequences and that maintain their activity. Indeed, the polypeptide of the invention, if required, can be modified in vitro and/or in vivo, for example by glycosylation, myristoylation, amidation, carboxylation or phosphorylation, and may be obtained, for example, by synthetic or recombinant techniques known in the art. In the present invention "functional" is intended for example as "maintaining their activity" e.g. immunomodulatory activity or anti-inflammatory activity. Also within the scope of the subject invention are polynucleotides which have the same nucleotide sequences of a polynucleotide exemplified herein except for nucleotide substitutions, additions, or deletions within the sequence of the polynucleotide, as long as these variant polynucleotides retain substantially the same relevant functional activity as the polynucleotides specifically exemplified herein (e.g., they encode a protein having the same amino acid sequence or the same functional activity as encoded by the exemplified polynucleotide). Thus, the polynucleotides disclosed herein should be understood to include mutants, derivatives, variants and fragments, as discussed above, of the specifically exemplified sequences. The subject invention also contemplates those polynucleotide molecules having sequences which are sufficiently homologous with the polynucleotide sequences of the invention so as to permit hybridization with that sequence under standard stringent conditions and standard methods (Maniatis, T. et al, 1982). Polynucleotides described herein can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be of 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or greater as compared to a sequence exemplified herein. According to the present invention, the pH of the fermentation medium is adjusted to be within the range of 5-7.5 prior to the fermentation. It is preferable that the pH is adjusted within the above-mentioned range, for example, by diluting with distilled water, etc., without using a pH adjustor after suitably processing the vegetative raw material, or by suitably adjusting the kind or amount of the vegetative raw material. If it is necessary to use a pH adjustor, one which is generally used for foods may be added as long as it does not deteriorate the effect of the present invention, and the kind thereof is not particularly limited. Examples of a preferable acid include citric acid, potassium sorbate, and examples of a preferable base include potassium carbonate. If the pH adjustor used is in a form of crystals, it is preferable to use an aqueous solution thereof. It is preferable that *Lactobacillus casei* or *paracasei* as defined above is used for the fermentation of medium after being precultivated. Using conventional methods the precultivation may carry out. Fermentation of the medium using *Lactobacillus casei* or *paracasei* may be carried out by using conventional methods. For example, the above-mentioned precultivated product may be inoculated so as to cultivate said *Lactobacillus casei* or *paracasei*. The amount of inoculation is preferably in the range of 0.1 to 10% by volume, the temperature during the cultivation is in the range of 4 to 40° C., preferably of 37° C. and the time period for the cultivation is preferably 16-30 hours. According to the present invention, the pH of the fermented product at the end of the fermentation is 5.5 or greater and less than 7.0. The composition according to the invention also comprises a fermented product of *Lactobacillus casei* or *paracasei* having the same bacteriological properties as those of the CNCM I-5220 strain. A further object of the invention is a fermented supernatant of *Lactobacillus casei* or *paracasei* species, as defined above, for use in the treatment and/or prevention of skin and/or dermatological diseases related to inflammation, allergic reactions, contact hypersensitivity reactions and intolerance, excessive sebaceous secretion, exfoliation or microbial dysbiosis (modification of the microbiota composition), preferably of the epidermis. The fermentation product of the present invention is preferably obtained by fermentation using a CNCM I-5220 strain, or a mutant strain of the CNCM I-5220 strain having the same ability, or a strain isolated from *Lactobacillus casei* or *paracasei* having the same bacteriological properties as those of the CNCM I-5220 strain. In particular, the second fermentation is preferably performed under anaerobic conditions at a temperature of 4 to 40° C., preferably 4 to 37° C., in particular 4° C. The fermentation is desired to be performed at a pH of 4 to 8.0, preferably 5.0 to 7.0, particularly preferably about 6.5. It should be noted that the above-mentioned fermentation product is desirably contained at a concentration of 1 to 20% or more in terms of dry weight. The fermented product as described above is therefore used as an active ingredient in the preparation of compositions for dermatological and/or cosmetic use. These compositions can be used, for example, to prevent or reduce the phenomenon of skin aging, in particular wrinkles, and/or to improve the appearance of the skin or scalp (in particular reduction of sebaceous secretion, itching due to dandruff and rebalancing of the hair follicle's microbiota). The compositions of the invention comprise the fermented product as described above and other dermatologically acceptable additional components. The definition "dermatologically acceptable" as used herein indicates that the compositions or the described components are suitable for application on human skin or on the scalp without toxicity risk, incompatibility, instability, allergic response, and the like. The fermented product as described above may be used in compositions appropriately formulated in an acceptable dermatological vehicle. The dermatologically acceptable vehicle can be an aqueous or hydroalcoholic solution, an emulsion water-in-oil, an emulsion oil-in-water, a microemulsion, an aqueous gel, an anhydrous gel, a serum or a dispersion of vesicles. The compositions may include, for example, vegetable oils, such as oil sweet almonds, olive, sunflower and/or beeswax. Moreover the compositions may include hyaluronic acid and/or glycolic acid and/or serum and sun protection factor. The compositions may include different additional ingredients, which can be active ingredients, functional agents or agents normally used in cosmetic products, products for personal care or for pharmaceutical use of topical or transdermal type. The decision to include an additional ingredient and its choice depends on the specific application and product formulation. A wide variety of additional ingredients that can be added into the compositions of the invention are mentioned in CTFA Cosmetic Ingredient Handbook, 10th edition, 2004 (published by Cosmetic, Toiletry and Fragrance Association, Inc, Washington, D.C.). Additional ingredients include amino sugars, vitamin B3 derivatives, dehydroacetic acid (DHA), phytosterols, salicylic acid, ascorbic acid and derivatives, sunscreens, keratolytic, anti-oxidant and anti-radical agents, antimicrobial agents, antibacterial agents, antifungals, thickening agents, anti-odorants and fatty acids. The compositions of the invention may comprise at least one vehicle acceptable from the dermatological point of view, which is chosen accordingly to the final formulation of the product. Preferably the vehicle is present at a concentration between 50% and 99.99%, more preferably between 60% and 99.9%, even more preferably between 70% and 98% by composition weight. The compositions of the invention may be obtained by any suitable method known to those skilled in the art for the manufacture of a cosmetic and/or dermatological composition. Said compositions may for topical applications. They may be present in different formulations, including creams, lotions, ointments, milks, gels, emulsions, suspensions, anhydrous preparations, lotions for scalp treatment, creams or lotions for skin or hair care, sunscreens, transdermal patches, spray formulations and soaps. Said compositions may be also in the form of lip sticks or, in general, of products suitable for face makeup. The invention will be illustrated by means of non-limiting examples with reference to following figures.

FIG. 1 PBMCs were stimulated with LPS (100 ng/ml) and treated with SN1 (supernatant of first fermentation) or its control (broth medium), or SN2 (supernatant of second fermentation) or its control PBS for 24 h. Concentrations of IL-10 and IL-12p40 were determined by ELISA. The delta % of response (normalized to LPS) was calculated as the net effect of each fermented product versus each relative control medium.

Figure 2:
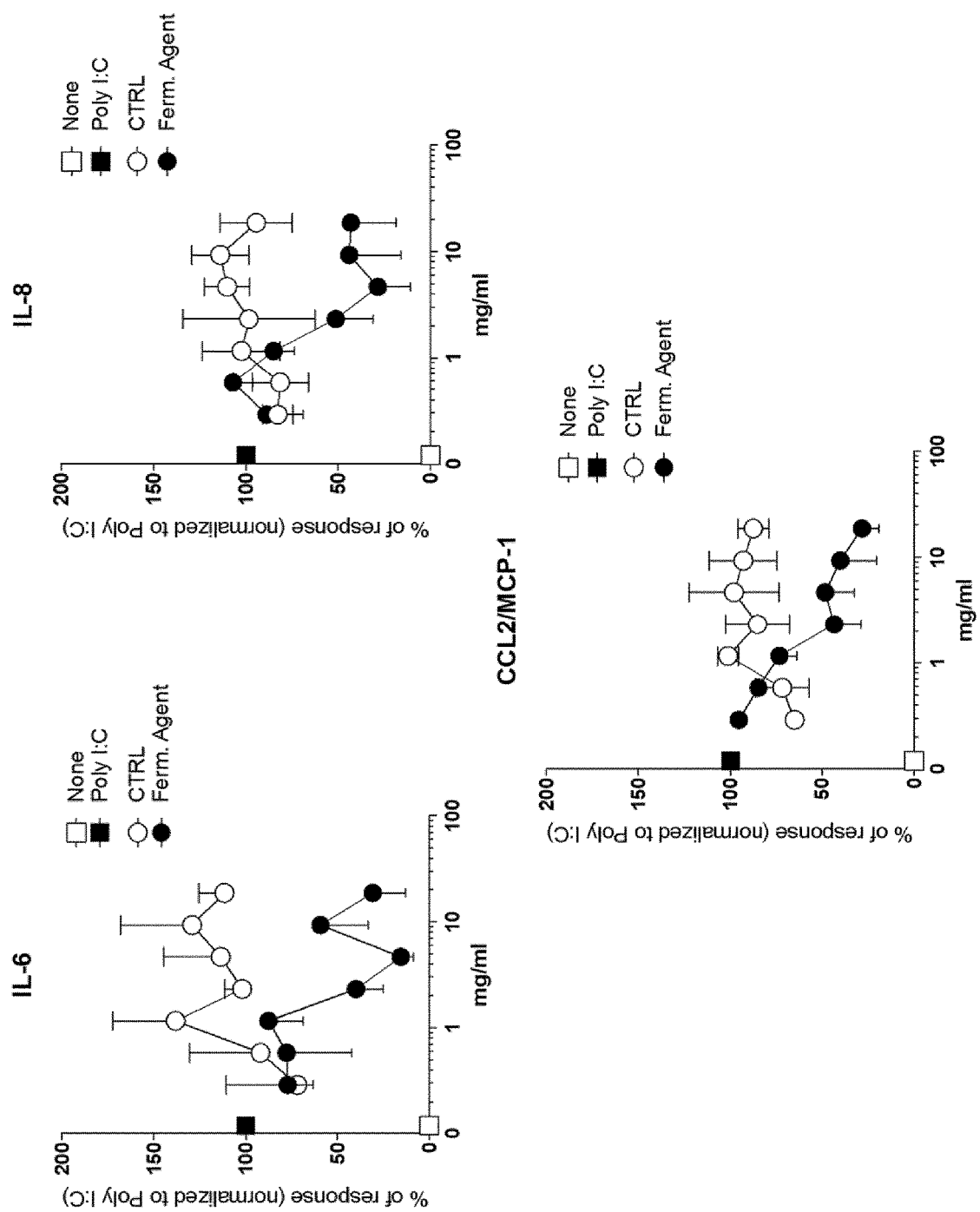

FIG. 2 HaCat cells were stimulated by Poly I:C (1 µg/ml) and treated with the Postbiotic and the relative control containing Mannitol and sodium lactate for 24 h. IL-6, IL-8 and CCL2-MCP-1 level were determined by ELISA. Mean of 3 experiments it is shown.

Figure 3:
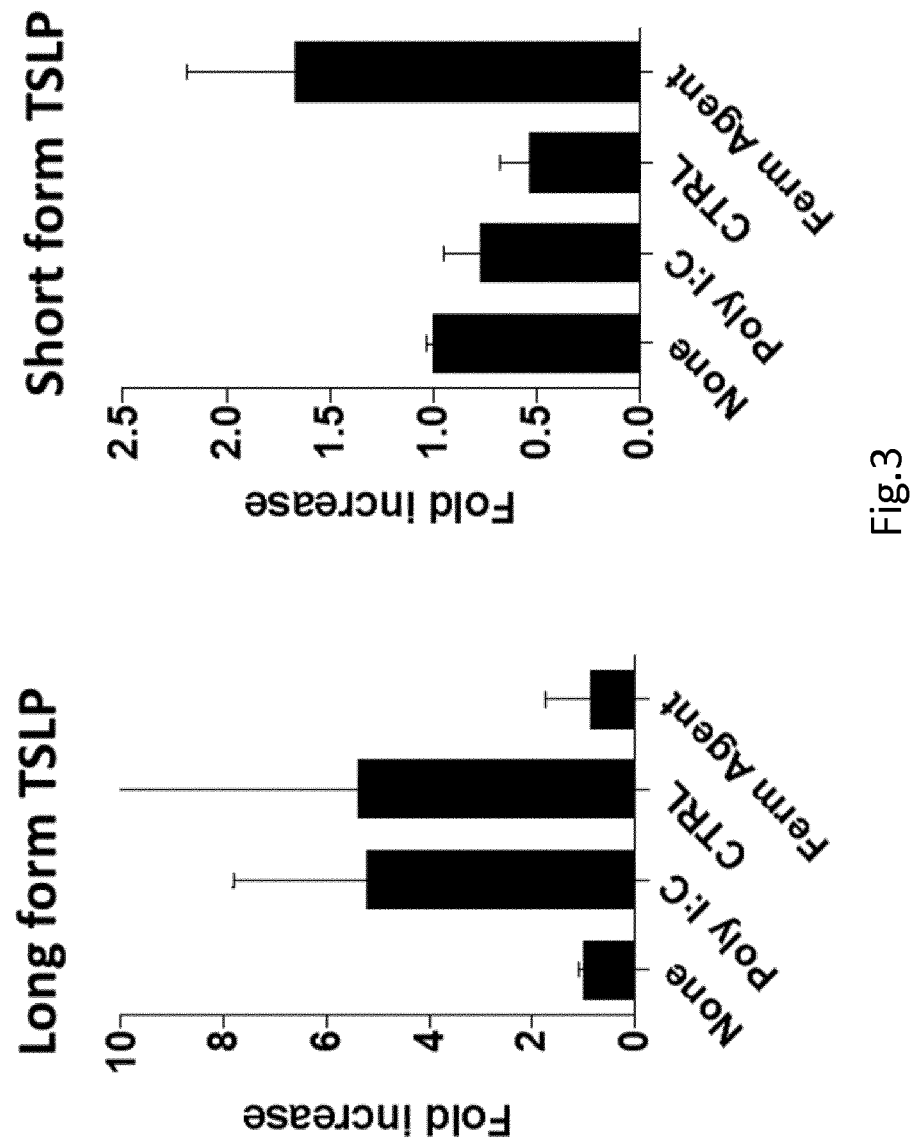

FIG. 3 HaCat cells were stimulated by Poly I:C (1 µg/ml) and treated with the Postbiotic and the relative control containing Mannitol and sodium lactate for 6 h. Gene expression of TSLP forms, lTSLP and sTSLP, were evaluated by qPCR.

Figure 4:
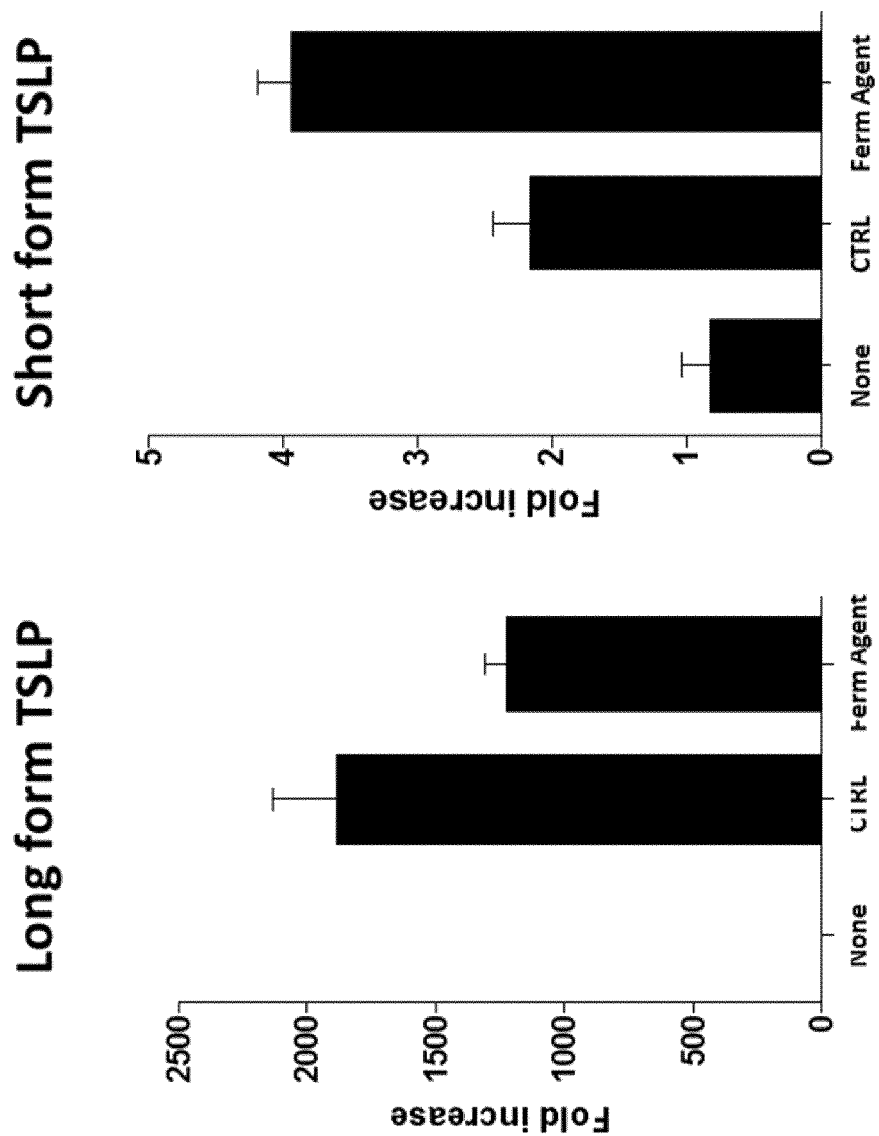

FIG. 4 NHEK cells were stimulated by Poly I:C (1 µg/ml) and treated with the Fermented Agent (Postbiotic) and the relative control containing Mannitol and sodium lactate for 6 h. Gene expression of TSLP forms, lTSLP and sTSLP, and its receptor, were evaluated by qPCR. Statistical comparisons were based used Mann-Whitney U Test. *$p<0.01$. Untreated and Fermented Agent (Postbiotic)-treated cells were compared with postbiotic Control. CTRL/Fermented Agent=1 mg/ml.

Figure 5:
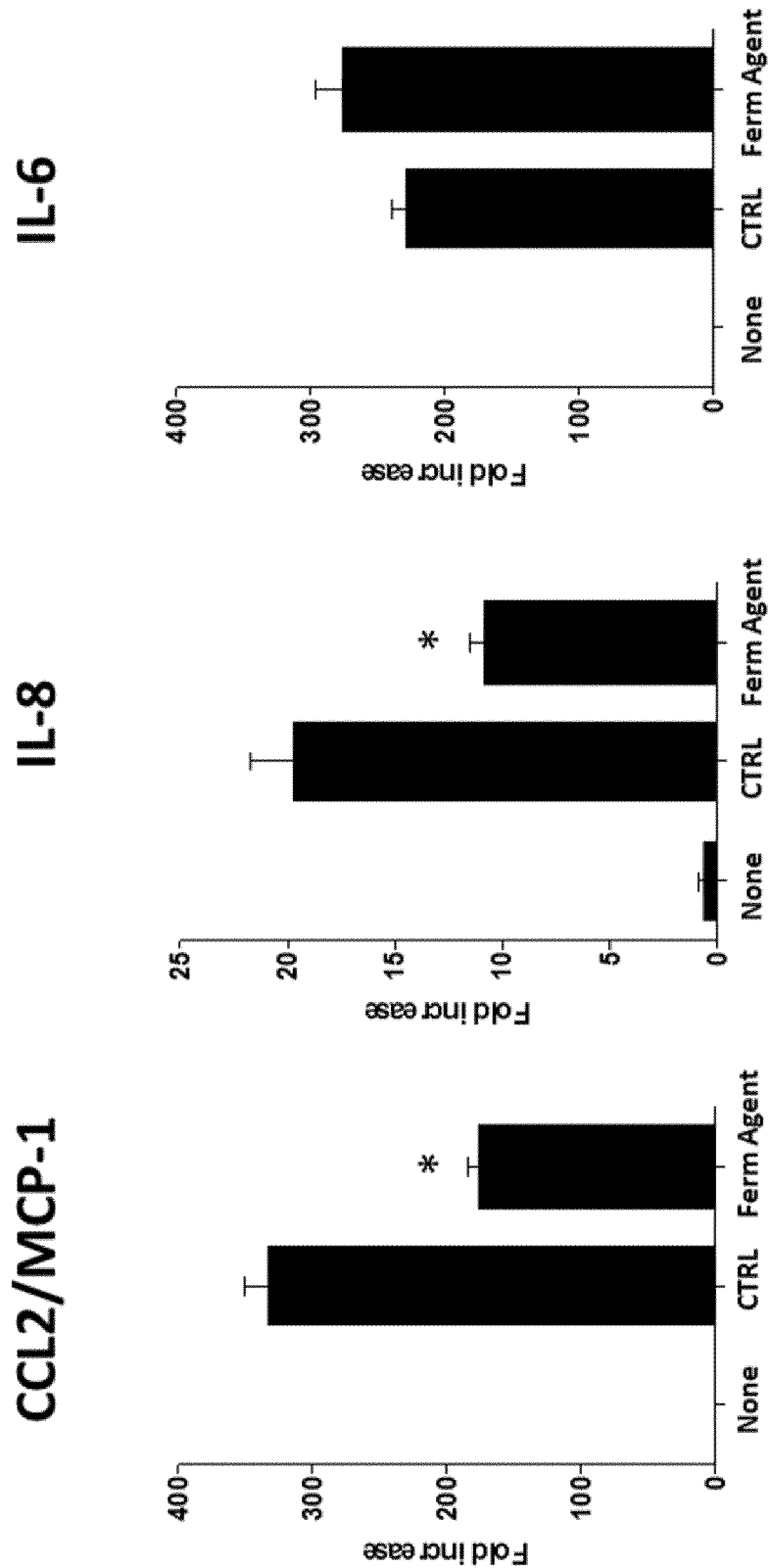

FIG. 5 NHEK cells were stimulated by Poly I:C (1 µg/ml) and treated with the Fermented Agent (Postbiotic) and the relative control containing Mannitol and sodium lactate for 6 h. Gene expression of CCL2/MCP-1, IL-6 and IL-8 were evaluated by qPCR. Statistical comparisons were based used Mann-Whitney U Test. *$p<0.01$. Untreated and Fermented Agent (Postbiotic)-treated cells were compared with postbiotic Control. CTRL/Fermented Agent=lmg/ml.

Figure 6:
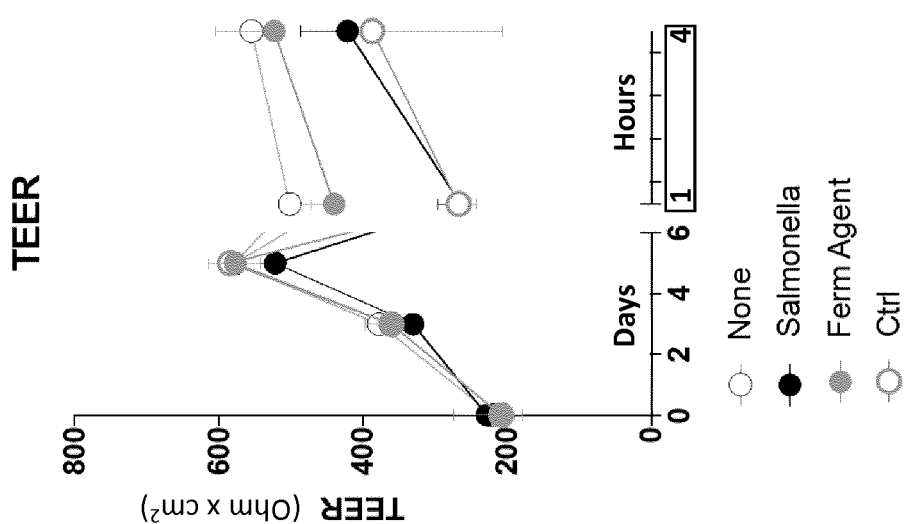

FIG. 6 Caco-2 epithelial cells were stimulated with *Salmonella* SL1344 ($6\times108$ CFU/well) for 1 h and 30' and treated with Fermented Agent (Postbiotic) and the relative control containing Mannitol and sodium lactate for the next 4 hours (CTRL/Fermented Agent=10 mg/ml). Trans-epithelial resistance was measured by chopstick electrode.

EXAMPLES

Material and Methods
Fermentation Process:
First Fermentation: *Lactobacillus Paracasei* Biomass Preparation An inoculum of *Lactobacillus Paracasei* strain CNCM I-5220 of Institute Pasteur collection, were grown in MRS medium at a temperature of 37° C. then gently stirred to avoid oxygenation of the culture medium, as MRS medium. The biomass is then allowed to grow for about 12 to 36 hours, preferably for about 24 hours, until the desired concentration of lactobacilli is reached comprise between $2\times10^8$ and $5\times10^{10}$ CFU/ml. The obtained bacterial suspension is centrifuged at 3500 rpm for 10 minutes to separate bacteria (biomass) from the supernatant to obtain SN1.

Second Fermentation: *Lactobacillus Paracasei* Supernatant Preparation (Postbiotic)

The *lactobacillus* biomass, as defined above, is transferred to a minimum solution (saline, phosphate buffer, H2O, etc.) with or without sodium lactate (appr. 5 5 g/L) and allowed to ferment for 12 to 36 hours, preferably for about 24 hours with or without agitation. The bacteria suspension is then centrifuged to separate them from the, second fermented product (SN2, here also referred to as "fermented product"), and the latter is used for the preparation of the formulation for topical use.

The "postbiotic" used below, is the fermentation product (SN2) mentioned above obtained in the presence of sodium lactate.

Preparation of the Topic Formulation

The fermentation product obtained from the first and/or the second fermentation (i.e. SN1 or SN2) is used in a topical formulation diluted to 0.01-10%, preferably to 0.5% in cream base made up with e.g. 60 g vegetable oil such as sweet almond oil, olive oil, sunflower oil and 3 gr of beeswax, hyaluronic acid (0.1%), glycolic acid, serum and sun protection factor (Spf20). The % of fermented product also depends on the concentration of bacteria obtained during the second fermentation.

Fatty Acid Analysis by GC/MS 250 ml of samples (of SN1 or SN2) were lyophilized and suspended in 500 µL. Trans-esterification was carried out by adding 850 µL of chloroform, 150 µL of H2SO4 and 1 mL of methanol. Thus, samples were heated at 100° C. overnight and to stop the reaction and eliminate water 2 mL of a 100 mg/mL sodium bicarbonate solution and 1 g of 99% bicarbonate were added. Subsequently, fatty acids were extracted using chloroform. 1 ul of the extract was analyzed in GC MS using a C18 30 m column. The fragmentation spectrum interpretation was performed by comparison with theoretical spectra in the NIST database. The area of the peaks was interpolated with a calibrator (FAME, Sigma Aldrich) to perform a quantitative analysis.

Peptide Analysis by MALDI-TOF 200 ml of samples (of SN1 or SN2) were lyophilized and suspended in 4 mL of 1% formic acid. 1 ml, of concentrated samples were analyzed by HPLC-UV on RP C18 column using 0.1% formic acid (eluent A) and acetonitrile containing 0.1% formic acid (eluent B) as eluents (flow rate 0.5 mL/min; absorption wavelength 220 nm). Fractions were collected and analyzed by MALDI TOF mass spectrometry in positive ion mode, using α-Cyano-4-hydroxycinnamic acid as matrix. Signals of interest underwent to tandem mass spectrometry analysis using MALDI TOF/TOF. The fragmentation spectra were collected and interpreted. The peptide sequences confirmed by alignment with the BLAST program.

Peripheral Blood Mononuclear (PBMC) Cells and Stimulation Conditions

Buffy coats were obtained from healthy donors having signed an informed consent for research use. PBMC were separated with Ficoll (GE Healthcare) gradient centrifugation and then resuspended and cultured in RPMI 1640 medium (Lonza) containing 10% fetal bovine serum (Gibco), 1% Glutamine, 1% pyruvate, 1% non essential AA and 1% Penicillin-Streptomycin. PBMCs were incubated with Lipopolysaccharides (LPS) from *Escherichia coli* O111:B4 (Sigma-Aldrich) in the presence or absence of serial dilution of 1.3% v/v liquid supernatant of first fermentation (SN1) or supernatant of second fermentation (SN2) for 24 h. Supernatants were tested for cytokine abundance by ELISA (R&D systems). The delta of normalized response to LPS of each fermented product was calculated by subtracting the effect of the media of fermentation (broth medium in case of SN1, PBS in case of SN2) from effect obtained by treatment with SN1 or SN2.

Stimulation of Human Keratinocytes in the Presence or Absence of Postbiotic.

Human keratinocytes cell line HaCat (Fornasa et al., 2015) was cultured in DMEM supplemented with 10% FBS, 1% Glutamine, 1% Penicillin-Streptomycin. Cells were stimulated with 1 µg/ml of Polyinosinic:polycytidylic acid (Poly I:C) and treated with serial dilution (factor 2) starting from concentration of 20 mg/ml of Postbiotic (i.e. lyophilized SN2 resuspended in water) and its relative control containing Mannitol and sodium lactate for 24 h. Then, supernatant was recovered and levels of inflammatory mediator IL-6, IL-8 and CCL2/MCP-1 were measured by ELISA technique (R&D systems).

Gene Expression of the Two Form of TSLP, lTSLP and sTSLP, was Evaluated by qPCR, after HaCat Cells Stimulation as Described Above, after 6 h.

Total RNA was extracted from the cells treated as described, by RNeasy Mini Kits (Qiagen), adding a DNase digestion step to clean the contamination of genomic DNA. 1 µg of RNA was reverse transcribed with the reverse transcriptase enzyme (Im-prom-II-reverse transcriptase, Promega), primers oligo (dT) (Invitrogen). Real time PCR (qPCR) was performed with Fast SYBR Green PCR kit on Applied Biosystems 7500 Fast Real Time PCR System (Applied Biosystems) with 20 ng of cDNA and specific primers for the two forms of TSLP (Fornasa et al., 2015). Gene expression was normalize to the expression the housekeeping gene, glyceraldehyde-3-phosphate dehydrogenase (GAPDH). The relative mRNA quantification was calculated by ΔΔCt method.

Stimulation of Primary Normal Human Keratinocytes in the Presence or Absence of Postbiotic Normal Human Epidermal primary keratinocytes (NHEKs, MatTek Corporation) were cultured in NEHK growth medium supplemented with 1% growth supplement (NHEK-GS, MatTek Corporation) and 50 µg/ml Gentamycin. Cells were stimulated with 1 µg/ml of Polyinosinic: polycytidylic acid (Poly I:C) and treated with 1 mg/ml of Postbiotic (i.e. lyophilized SN2 resuspended in water) and its relative control containing Mannitol and sodium lactate for 6 h. Then, gene expression of the two forms of TSLP, lTSLP and sTSLP, and inflammatory mediator IL-6, IL-8 and CCL2/MCP-1 was evaluated by qPCR. Total RNA was extracted from the cells treated as described, by RNeasy Mini Kits (Qiagen), adding a DNase digestion step to clean the contamination of genomic DNA. 1 µg of RNA was reverse transcribed with the reverse transcriptase enzyme (Im-prom-II-reverse transcriptase, Promega), primers oligo (dT) (Invitrogen). Real time PCR (qPCR) was performed with Fast SYBR Green PCR kit on Applied Biosystems 7Flex Fast Real Time PCR System (Applied Biosystems) with 20 ng of cDNA and specific primers for the two forms of TSLP (Fornasa et al., 2015). Gene expression was normalized to the expression the housekeeping gene, glyceraldehyde-3-phosphate dehydrogenase (GAPDH). The relative mRNA quantification was calculated by ΔΔCt method.

Stimulation of Human Epithelial Cells in the Presence or Absence of Postbiotic

Caco-2 cells (human epithelial colorectal adenocarcinoma cells) were maintained in DMEM supplemented with 10% FBS, 1% Glutamine, 1% Penicillin-Streptomycin. Experiments were performed seeding $6 \times 10^4$ cells/well on polycarbonate membranes (Transwell 6.5 mm in diameter, 5 µm pore size) (Costar Corp). Caco-2 cells growth were monitored by measuring the trans-epithelial electrical resistance (TEER) until confluence by chopstick electrodes (Millicell-ERS, Millipore). TEER is a widely accepted quantitative technique to measure the integrity of tight junction dynamics in cell culture models of epithelial monolayers. Then, the cells were stimulated with $6 \times 10^8$ colony forming units (CFU)/well *Salmonella typhimurium* during 1 h 30' and then the cells were treated with Postbiotic (i.e. lyophilized SN2) and its relative control containing Mannitol and sodium lactate for the next 4 hours and the TEER was measured to evaluate the integrity of the monolayer at endpoint.

Results

Chemical and Functional Characterization of Fermented Processes Supernatant

In order chemically characterize the supernatants a quantification of fatty acid was performed by Gas Chromatography with Mass Spectrometric Detection (GC/MS). The inventors found that the fermented product (supernatant/SN) derived from the first fermentation process (SN1) and from the second fermentation process (SN2) had a different fatty acid profile (Table 1). Both supernatants contain oleic acid which is reduced in SN2 compare SN1. These results indicate that the composition of the supernatants is different. Moreover, supernatant was analyzed for bio-peptides content by MALDI-TOF technique. The inventors found that the SN1 and SN2 had also a different bio-peptides profile. In particular, for SN1 was not detected any signals by MALDI/

TOF compare to SN2 (Table 2a) and relative fragmentation (Table 2b). These results further confirm that the components present into the two supernatants are different. In addition, the inventors have evaluated the immunomodulatory proprieties of the two supernatants on LPS-stimulated PBMC. Peripheral blood mononuclear cells (PBMC) are a heterogeneous cell population that includes myeloid as well as lymphoid immune cells. Supernatants, SN1 and SN2, were tested for their ability to modulate cytokines release in particular IL-12p40 and IL-10 by LPS-stimulated PBMC, which is a stimulation that mimicking innate immune activation. The inventors found that SN1 (fermented product derived from first fermentation) and SN2 (fermented product derived from second fermentation) have different immunodulatory profile. The net effect of each fermented product was calculated subtracting the contribution of the relative fermentation media (see material and methods). The inventors found that SN2 led to a reduction of IL12-p40. Conversely, SN1 induces IL12-p40.

In addition, SN2 significantly increase secretion of IL-10 (FIG. 1) compare to SN1. Those results indicate that SN2 has immunomodulatory proprieties characterized by the reduction of proinflammatory cytokine IL-12p40 and increase of anti-inflammatory cytokine IL-10 controlling activation of both innate and adaptive immune system compartment. These result, clearly demonstrate that the two supernatants are different both in term of chemical composition that biological/immunomodulatory function.

The Effect of Postbiotic on Keratinocytes

The epithermal epithelial cells, keratinocytes, play an essential role to the formation of cutaneous barrier and in the orchestration of innate and adaptive immune response to external stimuli. Alterations of these responses are responsible for several epidermal diseases. In particular, increased secretion of IL-6 and IL-8, cytokines by keratinocytes, promotes a reduction of cornified-envelope-associated protein such as filagrin, loricrina and keratin (Noh et al., 2010) (Jin et al., 2014). Moreover, the release of chemotactic factors such as CCL2/MCP-1 will recruit cells of the immune system, amplifying the inflammatory response. Such immune response in combination with the long inflammatory form of TSLP, lfTSLP, and with an altered release of the constitutive form, sfTSLP, will favour the establishment of an allergic response, Th2, of itchy manifestations and a reduced antibacterial activity. The inventors have stimulated a human epidermal keratinocytes cell line, HaCaT, widely used and representative of primary human keratinocytes, with an inflammatory microbial derivative that mimics the double-stranded viral RNA, the Poly I:C, for 24 hours. The aforementioned stimulation induces the release of inflammatory cytokines as IL-6 and IL-8 and of chemotactic factor CCL2/MCP-1 (FIG. 2). The inventors have found that the presence of the Postbiotic during the stimulation significantly reduces, in dose-dependent manner, IL-6 and IL-8 cytokines and chemotactic factor CCL2/MCP-1 levels (FIG. 2). The inventors have also stimulated HaCaT cells, as described above, for 6 hours, and observed an increase of RNA level of the lfTSLP (inflammatory) and not of the sfTSLP (homeostatic) (FIG. 3). The inventors have discovered that the presence of the Postbiotic during the stimulation reduces the levels of the cytokine lfTSLP (inflammatory) and increases the levels of the cytokine sfTSLP (homeostatic) (FIG. 3). These results indicate that the postbiotic (fermentation product of L. paracasei), acts on keratinocytes by modulating the release of immunological mediators, favouring the re-establishment of skin homeostasis status. The inventors have also stimulated primary human epidermal keratinocytes, NHEK, with an inflammatory microbial derivative that mimics the double-stranded viral RNA, the Poly I:C, for 6 hours. The inventors have observed an increase of RNA level of the lfTSLP (inflammatory) and the sfTSLP (homeostatic) (FIG. 4). The inventors have discovered that the presence of the Postbiotic during the stimulation reduces the levels of the cytokine lfTSLP (inflammatory) and increases the levels of the cytokine sfTSLP (homeostatic) (FIG. 4). These results indicate that the postbiotic (fermentation product of L. paracasei according to the invention), acts also on primary human epidermal keratinocytes by modulating the release of immunological mediators, favouring the re-establishment of skin homeostasis status. The aforementioned stimulation induces the up-regulation of inflammatory cytokines as IL-6 and IL-8 and of chemotactic factor CCL2/MCP-1 (FIG. 5). The inventors have found that the presence of the Postbiotic during the stimulation significantly reduces chemotactic factor CCL2/MCP-1 and IL-8 cytokines expressions without affecting IL-6 level (FIG. 4). These results indicate that the postbiotic according to the invention, acts on keratinocytes by modulating the release of immunological mediators, favoring the re-establishment of skin homeostasis status.

The Effect of Postbiotic on Epithelial Barrier Integrity.

Epithelial cells create a protective layer for both the outside and the inside cavities and lumen of the body. Epithelial cells are connected to each other via intercellular junctions and barrier integrity is essential for the physiological activities of the tissue. The tight junctions create fusion points between epithelial cells, that regulates diffusion and allows both of these cell layers to form semipermeable cellular barriers that separate apical (luminal) and basolateral (abluminal) sides in the body, controlling the transport processes to maintain homeostasis. The inventors have seeded Caco-2 (human colon adenocarcinoma cell line) in transwells and their growths were monitored by measuring the transepithelial electrical resistance (TEER). When the junctions are strong, it is more difficult for the current to pass between the cells, thus TEER is high; otherwise when junctions are compromised the resistance is lower. The inventors tested the protective properties against enteric pathogen Salmonella on monolayer of Caco-2 cells on transwells. The cells were infected with $6 \times 10^8$ colony forming units (CFU)/well Salmonella typhimurium for 1 h 30' and then the cells were treated with Postbiotic (i.e. lyophilized SN2) and its relative control containing Mannitol and sodium lactate for the next 4 hours. During all the experiment TEER was measured to evaluate the integrity of the monolayer. The stimulation of Caco-2 cells with Salmonella typhimurium causes a monolayer breakage thus registering low values of TEER. The inventors found that Postbiotic was able to maintain the monolayer integrity after the damage caused by Salmonella typhimurium insult (FIG. 3) shown by high values of TEER that were similar to the unstimulated cells.

Tables

TABLE 1

|  |  | mg/L |  |  | mg/L |
|---|---|---|---|---|---|
| SN1 | oleic acid | 7.98 | SN2 | 7 hexadecenoic acid | 5.12 |
|  | decanoic acid | 1.30 |  | tridecanoic acid | 5.42 |
|  | benzopropanoic acid | 2.69 |  | vaccenic acid | 12.23 |
|  | citric acid | 13.05 |  | oleic acid | 3.21 |

Fatty acid profile quantification of the fermented product supernatant of *Lactobacillus Paracasei* strain CNCM I-5220 obtained from (A) first fermentation (SN1) and (B) second fermentation (SN2) process

TABLE 2

A

| SN1 m/z | SN2 m/z |
|---|---|
| NO signaL | 357.07 |
| | 423.06 |
| | 373.05 |
| | 406.07 |
| | 439.04 |
| | 489.05 |
| | 505.03 |
| | 538.05 |
| | 557.1 |

B

| | SN2 |
|---|---|
| Fractions | m/z |
| 3 | 1193.2 |
| | 855.2 |
| | 756.38 |
| 4 | 524.06 |
| | 542.08 |
| | 664.12 |
| | 756.38 |
| | 644.37 |
| 5 | 756.43 |
| 6 | 610.34 |
| 12 | 1006.8 |
| 13 | 1393.2 |
| | 1153.77 |
| | 1033.68 |
| | 707.28 |
| | 855.54 |
| 15 | 1153.76 |
| | 1393.8 |
| | 1033.65 |
| | 855.34 |
| 16 | 1153.76 |
| | 1393.8 |
| | 1033.65 |
| | 855.34 |

C

| | SN2 | | |
|---|---|---|---|
| Fractions | peptides | sequences | Protein |
| 3 | 855.2 | PDLKDVG (SEQ ID NO: 19) | riboflavin byosintesis protein |
| | 1193.2 | LEIHLNAAQ (SEQ ID NO: 20) | type 2 isopentenyl-diphosphate Delta-isomerase |
| | 1193.2 | GTNFATIENA (SEQ ID NO: 21) | |
| 4 | 756.43 | GTDTRAE (SEQ ID NO: 22) | riboflavin byosintesis protein |
| 5 | 756.43 | GTDTRAE (SEQ ID NO: 23) | riboflavin byosintesis protein |
| 6 | 610.34 | YINAM (SEQ ID NO: 24) | type 2 isopentenyl-diphosphate Delta- |
| | | FMWQ (SEQ ID NO: 25) | |

TABLE 2-continued

| | | | |
|---|---|---|---|
| | | HLIQT (SEQ ID NO: 26) | isomerase |
| 12 | 1006.8 | TAFAALTEL (SEQ ID NO: 27) | riboflavin byosintesis protein |
| 13 | 707.28 | MEANML (SEQ ID NO: 28) | riboflavin byosintesis protein |
| | 1393.8 | NDYEKIAMGLLS (SEQ ID NO: 29) | |
| | 1033.6 | FIPDLKDV (SEQ ID NO: 30) | |
| | 1153.7 | MPTEQ----- (SEQ ID NO: 31) | tetratrico-peptide repeat protein |
| | 855.2 | PDLKDVG (SEQ ID NO: 32) | riboflavin byosintesis protein |
| 15 | 855.34 | PDLKDVG (SEQ ID NO: 33) | riboflavin byosintesis protein |
| | 1393.8 | NDYEKIAMGLLS (SEQ ID NO: 34) | |
| | 1033.6 | FIPDLKDV (SEQ ID NO: 35) | |
| | 1153.7 | MPTEQ----- (SEQ ID NO: 36) | tetratrico-peptide repeat protein |
| 16 | 855.34 | PDLKDVG (SEQ ID NO: 37) | riboflavin byosintesis protein |
| | 1393.8 | NDYEKIAMGLLS (SEQ ID NO: 38) | |
| | 1033.6 | FIPDLKDV (SEQ ID NO: 39) | |
| | 1153.7 | MPTEQ----- (SEQ ID NO: 40) | tetratrico-peptide repeat protein |
| | 1006.8 | KLTEATVM (SEQ ID NO: 41) | tetratrico-peptide repeat protein |

Peptide profile of the fermented product supernatant of *Lactobacillus Paracasei* strain CNCM I-5220 (first fermentation (SN1) and second fermentation (SN2) process) obtained from MALDI TOF mass spectrometry (A). Signals of interest from SN2 were profiled by MALDI TOF/TOF (B) mass spectrometry. (C) Peptides sequence profile of the fermented product supernatant of *Lactobacillus Paracasei* strain CNCM I-5220 (second fermentation (SN2) process) obtained from MALDI TOF mass spectrometry. Fragmentation spectra of peptidic origin were interpreted and sequences confirmed by alignment with the BLAST program Sequences Included in the present invention are also nucleic acid sequences derived from the nucleotide sequences shown below, e.g. functional fragments, mutants, derivatives, analogues, and sequences having a % of identity of at least 70% with the below sequences.

In the following are disclosed five gene sequences, representing specific core genes of *L. paracasei* and *L. casei* species.

SEQ ID 1

ATGAATCAAAAAGCTTTGAATCAATTTCCTGAACTTACCTACACAGAA

CAAGTGTCGGTTGTTGGCGGCGATTTGTCAGTCGAAGTCATCATGAAA

GGTATCTTCACCGGTATCTTTGATGCTGGGTACCAAGTGGGTCAGTCA

ATCGCAAAATGGGTTAAGTAA

SEQ ID 2
ATGAAAGGTAAGCGGCAGCACTTACTTTTATATTTTGTTCTGGGTATG

ATGACAGGACTGGTGACGGCAGCGATTTTTCATATCATTTATGCCTGG

CTTTTTCATTGA

SEQ ID 3
ATGCCCAAAAGGGTCGATCAACATATACGTTCACGCCTTAAAGGCTTT

ACTTTAATTGAAGTGGTGGTCAGCCTGATTTTACTTGCGGCGGTCATG

CTGTTATGGCGACCGGTTTTATTGCATGTCACGCGGTTCACGCTTCAA

GACCATGTGCTAATCACGTCATTGCAAGCAGAGCATGACTTGCAAATG

TTTGTACGAGATAAAAAGTTGCGGTCTGTGGCCTTAATGTCGGTAAGG

GTGAGAAGTCCCGAGAAAGCTTACACGATCAATTTTTATCAGACCAAA

CATTTTCGCGGTATGGTTCGTGTGATGGGATCTGAAAATGGGCATATG

CCATTATTTACGCATCTAACCGGTGTCAATTTTAGCAAGGTAGCTCAA

GGCTTTCGCTATCGTCTGTATTTGACGACTTCGCAGAAGATTGACGGT

GGGGTGCAAATCGATGAAGATACGCGGTAG

SEQ ID 4
ATGGCCGCTGATTTCACCCAATTACAACAAGCCATTCGCTTGCTCAAT

GCCCATACTCGAGCTGCTGATGAGCAAGCGTGGCAAGTGCTTTTTGAT

CGTTGGCTGGCAACTTTATCCTCTGAAACTCGCCGGCAAATGCAAACA

GTTCGGTTTAATCATGCCCAATTGACGTTACTCACAACGCTGGATCAA

AGCAGTCGCAAACAACTGCGCAATCAGGATTTAACCGCTGCTGTTCCG

TTCTCACAAGGCCTAGTCTCACGCTATGTTGCTCGCCTTGTTCAATTA

AACTTGCTGACAAAATTATCCTTGCCCGACAATCGCAAGGCCTACATT

GTTGCACTAACTCCGCTTGGTCAACAAGTCGCTGCCTTACATCAGCAA

ATGCATCATCACACAAATGCTCAACTCGCCTCTGTACTTCATACCCTT

GATCCACAAGATGTTCAAACTACCATTCAGGTACTCACAAAACTGACG

GCTCAGCCTTTACATCCCAAGTCTTAG

SEQ ID 5
ATGGGCGGTGTCATTTGTTACGCGGTGCCGGTCTTTTGGAAAAGAATA

CTTCGCAGACACCTGATTCACGAGATTAAGACCCTGAATCAAGGATTG

CAGTTATCAAGCAAAGCCATGAGCCAATTAATTGATCCGGAAAATCCT

TATATGGTATTTGCTGATGAAAATGGTGAACTGGATTTTTCATTTTTG

TGGCTAGGCAACTTGCGTCAATTGAGGCGTGAACTGCGTCTAATTAAA

GAACAGAAAGCTAGGGTTTGA

In the following are disclosed unique sequences of *L. paracasei* B21060 with respect to the *L. paracasei* species publicly available in NCBI databases. SEQ ID 6 to 8 refers to gene sequences, whereas SEQ ID 9 to 18 refers to genome DNA sequences.

SEQ ID 6:
ATGAGTAAATATAAAGTTATTATTTGGGGATTAGGAAACGTTGGTCGTTCCGCAGTGAGA

ATGATCGCGGAAAGACAAAATATTTTTGAATTGGTTGCAGCCGTTGACGTTGATCCAAAG

AAGTTAGGTAAGGATGCCGGAGAAGTCTTTGATTTTGACAAAGTCGGCGTCAAAGTTTCA

GATGATATTGATGCAGCCTTGAAACTTCCAGCTGACATTGTGCTCGACTTTTGCCCAACG

GAAATGGACAAACAAGGAACATTCATGCCTTCTGCTATTCGACTCGCCAAATCGCTCGAT

GCCGGTAAAAACGTTATTACCACGATTCCGGTATATCATGTTCAAGACAGTCAGCCAGAA

GTATATGAATATCTAAATGAACATGCTAAAGCACATAATGTTGCTTTTGTACCATTTGGA

CTTTTGCCAGGCGATTATGCCTCATATATCCCACTAGTTTTGGCCGGGGCCATGGGCCAC

GTGGATAAAATTGTTGTTCAATCCGGTGAAGATGACTGGCACAACACATCAGGCTGGGTC

GATGTCTTCTCATATGGCGGCGATATCAATAAATATCCAAAACCAGACTCAGACGAAGAT

CTCTTGGCTAAGTTCATTTATGCTTATTATTCATCCGGCGTATACGAGATGGCCGATAGG

ATCGGTCTGAAATATGATACCTTCAAACCAGAGCATGAAGTCTTCACTGCACCCAAAGAT

TTGGAAACGATCAAGGGTACAGTCAAAAAGGGCAGCATTTATGCCCACAGATTTACCATG

GCACTTTACAACGGCAACGAACAAGTAGCCGCCTTAAGATATGTTCATAAAGTTGATAAT

AAAGAGACACCAGAATTACCGATCAATAATACGATTCATATTGAAGGCTTGCCGTCAGTC

GATGCGCAGATCGATGGATTGATCCCAGAAAGAGAAGGCTACGTTTCATCAGCCGCTCCA

GCAGTCAACTTGATCCCTAGCATTCTCGAGACCGACAAGACAGGTTATGTTGAAGTCTGC

GACCTTCCAGTAGTGATTGCCAGGCCATTGGATATTGGCGCAAAAAAATTAGTCTAG

SEQ ID 7:
ATGGCAACCTATTCGCAGATAGAACTAGACATAATCAAATCATTTAAAGGGCTGATGAAA

-continued

GACCATGAATTCACTGAGATCTCAATTAAAATGATCGCTGAAAAAGCCGATATCACTCGA

CGCGGCTTTTACAATCACTTCTTAGATAAATATGATCTTGTCAGTACCATCTTTGAGCAT

GATCTTTTTCCAACAGTCATCAGTTTGACGAATATCAATGACTGGGATCAAGGGTCGCTG

TTTATCGTGAATTATCTCCAAGACAATCGCGACTACTATAAAAAATTGTTGTCGCTTGAA

GGACAAAACTGTTTACAGACAGACTTTTATAAATTGACTGAGATGCAGATTGGGATCTTG

ATCCCAGAAATATTGGTCGGTAGGAAAATTTCTGACGAAGATCAGGCATTTTTAAGCGAT

TATTATTTTCACGCTTATATGGGACTGACTACCGAATGGGTCAAAGGTAAATATGGTTTT

TCAACTCAGGAGTTCGTTAAACGGTGGAAAGCCTTACTCAATAATTCAATGCATAATTAT

CTGGACAACTACGCTCGATGA

SEQ ID 8:
ATGAGTAAATATAAAGTTATTATTTGGGGATTAGGAAACGTTGGTCGTTCCGCAGTGAGA

ATGATCGCGGAAAGACAAAATATTTTTGAATTGGTTGCAGCCGTTGACGTTGATCCAAAG

AAGTTAGGTAAGGATGCCGGAGAAGTCTTTGATTTTGACAAAGTCGGCGTCAAAGTTTCA

GATGATATTGATGCAGCCTTGAAACTTCCAGCTGACATTGTGCTCGACTTTTGCCCAACG

GAAATGGACAAACAAGGAACATTCATGCCTTCTGCTATTCGACTCGCCAAATCGCTCGAT

GCCGGTAAAAACGTTATTACCACGATTCCGGTATATCATGTTCAAGACAGTCAGCCAGAA

GTATATGAATATCTAAATGAACATGCTAAAGCACATAATGTTGCTTTTGTACCATTTGGA

CTTTTGCCAGGCGATTATGCCTCATATATCCCACTAGTTTTGGCCGGGGCCATGGGCCAC

GTGGATAAAATTGTTGTTCAATCCGGTGAAGATGACTGGCACAACACATCAGGCTGGGTC

GATGTCTTCTCATATGGCGGCGATATCAATAAATATCCAAAACCAGACTCAGACGAAGAT

CTCTTGG CTAAGTTCATTTATGCTTATTATTCATCCGGCGTATACGAGATGGCCGATAG

GATCGGTCTGAAATATGATACCTTCAAACCAGAGCATGAAGTCTTCACTGCACCCAAAGA

TTTGGAAACGATCAAGGGTACAGTCAAAAAGGGCAGCATTTATGCCCACAGATTTACCAT

GGCACTTTACAACGGCAACGAACAAGTAGCCGCCTTAAGATATGTTCATAAAGTTGATAA

TAAAGAGACACCAGAATTACCGATCAATAATACGATTCATATTGAAGGCTTGCCGTCAGT

CGATGCGCAGATCGATGGATTGATCCCAGAAAGAGAAGGCTACGTTTCATCAGCCGCTCC

AGCAGTCAACTTGATCCCTAGCATTCTCGAGACCGACAAGACAGGTTATGTTGAAGTCTG

CGACCTTCCAGTAGTGATTGCCAGGCCATTGGATATTGGCGCAAAAAAATTAGTCTAG

SEQ ID 9 Position 102558 . . . 102986
AAAAACGGCTTAGAACGCTCATATTTGCGTTCTAAGCCGTTTTTATCAGCATAGGTTCTT

GACACCAATAAACATCTTTAGTAATTGATCAAATTTAGGCAATGTGCTTTTGTCGGTGAA

TGGCGATAGCCCTACCGAAGCTTCAGCTGAGGTTCTTCTGAGCCACGCAAGCGAAGCGCG

CTAGGGCAAGCCAACGGCGCGCAGGCGAAGCCGGAGTTAAATGTGGCGCAGCCACACCTT

TTTAGGGAGCAACGCGACCAGAATTTTGTATGGGGTTTGGGAAGAGGTTCTCCCCAAGGT

CTTTTGTGGTTATTAACAAGCAAAACACAAACACAAGCCTCGCGCGCGTTATATATACTT

CTAAATACTTTTAAATACTTTAAGTACTTAGGGAGACGAGAATGGCTCAACCACGCGTTT

AAATCGACT

SEQ ID 10 Position 103624 . . . 103864
ACGACCTCTCGACCACCCACTGCCTCACCAATCCCCAGGTGAACCGGGCCAAGGGCACTA

CCGAGCAACCCGACCCCTATATCCCGGTGGGCGTGGTGAAGCAGACCGATGGGGGCATCG

TGGTGCGGGGCGCGCGGATGCTCTCCACGCTGCCCACGGCGGATGAGCTTTTAGTCTTCC

-continued

```
CCAGCACTTTGCTCAAAGAAGGGCCGGGAGCCGACAAGTACGCCGTGGCCTTCGCCATCC
C

SEQ ID 11 Position 254291 . . . 261674
ATTGATCGCCTCCGGGTCACTTATATGTAACTAATAATACTCCCTTCTCTCTTTAGTTAC

AATAGGGTACAGCCTATCGAATCACTTACGCTTCCACTTTGAGATAACTTTTCGTTATTA

TTTATCAACGGCATTAACGATATCATTAACTGTTTGCAATGCATCGCTCAGTACACTAAT

TGGTGCTTGTTCAATATACTGCATGTGTCGTTGTACAAAATCAAAGGTGTGAAATTGTAA

CGGATTCACGTACCCTTCTATTTTTTCAGTCTGAATCGGTACCATCAAGCCTGTTTCAGC

TAAGCGATTATGTTTGGCATGCGTGATCGGACAAACCAACGCTAATCCAGTCATTTTGGC

ATATTGTTGATTGCTAATAACGAGCGCTGGTCGTCTTTTTTGAATTTCATGACCCCGACT

TGGCATGAAATCAATACTCACAACATCACCTTTGCGTGGTTGATAATGCCTAGTCCCACT

CACTTGGTAATACCTCGTTTTCTAACGTAATATCTTGTTGGTGTACTTGTTGCTTGTACC

AATCACCTTCAAATGGATTGCGGTGCTTCGGCAGATAAAGAATGCCACCATCATCACGTT

GCTCAACTGTAAATTCAGTTCCATCGGCGATTTTAATACTCTTTGGAATGGTTAATGTAA

TGGAATTGCCAACCCTTCTTGCTTTAACTGTCATTGAAATCATCCTTTCGTATACACCGA

GTATACACCAGCGCGAATGAATCTGCAACTCTTGTGCCCTCTTGTGTACAAACACCACTG

TCAATTTACTTTTGCCTATTGTGCTTTATCTCTTCTCGTTCTGTCATTAGTATGCCACCA

ACACGGCCGACTTCATCCGGCTCACCTTTGATGACGCCTTGAATACCATCGATTTGCTTC

CAAGTCTTTACTTCCAAGTTCTTCAAAGACTTTGATATCGTTTTTCGATGCCGGCAAACA

CTTCTTCATTCTGATGCCTTTCAAAGAATTCCTCTAGATCATTCATCAGAGATTCTCCTC

ACTTAAACCTAGTTGGCGTCAAATTCCATCTCAGCAATCGAATCTTCTAGGCTGTCCATT

ACTTCGTATGTTTCAATGAAGTTAACCCAGCTGTCATATGGATGTAGTTTGCTTTCTTTA

ATGCTAGTTCTAAGCTTTTCGTACACGTTGTCAATAAACTGCTCAACCATCCTATTAACC

GCACTATTAATAACCGCTTCGTTCCACTGCTTAGATGCTGCACGCTTTCGATTTTGACTA

TGCTGATGGGACAGCGCCCGGCTTCTGAACAACGCTACTGCCCTGCTGTTAGCATTCAGA

TAGGTTTCAAATTCTTCACGATCCATTACGTTTCCTCCTCAAAATAAGCCTCATTTCATA

GCACAGCTTCAGCAAAAGGCATGTCATCCTACATGCCTTTTTTCTGTTGCTCTTCAATAT

CAGTATAAAACGTCCTGCCGCTTTAGGCAAACGTATGTTCGCTATTAAGAACATACGTTT

GTATAATAACTATAAAAGATTTAAAGGAGGTCAATCGTATGGAAAACAATGTCCCGCGTG

AAAAATGGCTTTACCCTGACCGCTGCATGAAGAAATGGCTGGGCTGGATTCTAAGCGACC

ATTCCGCCTATATGGAAGAAGCGGCTATCTCAGAACAACCGGTGCTCCCAAAGCCTGAAC

AGACACAAGAAACCATTAATGGCGTACTCGAAGATGCTTGGCAAAACTCAAAAATTGTCG

CAGTTCAAATCGGTACGCCATACGATGATCTTCTGTTACCGGATATTGAAGGCGCCGTGA

TTGGTCATTGGGACGCTCAGGTTTATCTACAGCTTAAAACTGGTGAGATGCAATCCATTA

ATGCAGCGGACATTCGCAATGTGCAACTGCTCAATCCAGATCGGTGGTGGGCGTTAGTAT

GACGACACCATTAGATGATCCAACAAGGTTACCGGTACACGACATTATGTGCATTGACTG

TAAGTCCTTTTACGCCTCAGTTGAAGCTATCAGACGCGGGATTCATCCGTTAGCCGCCGA

CATTGCTGTTCTCAGCAAAGGTAATTCTCCTGGCGGTTTGGTGCTGGCTGCTAGTCCCAA

CTGCAAAAAGCGTTACCACGTAGGACTGAGTACACGCCGTTTTCAGCTAAGGGACGATAT

GTAGGTAGAACTTGCTGAACCGCGGATGGCTAATTACATTCGCAAGAATTACGGTATCAA

TCGTATTTACCGTCAGTTTACTGACGATGCTCACTGGTCTCCCTATTCCGTTGACGAGTC
```

-continued

```
CTTTATTGACGTTACCCACCCCCACAATCTCTTCGGTTCTAATGAAGAAATTGCTACCCA
AATACAGAAGAAGGTGTTTGATCAGTTTGGCATTGTCACAACAGTTGGCATTGGGCAAAA
TCCCCTATTGGCAAAATTAGCCCTAGATAACGAGGCTAAGAAGTCAACGCCTTGGCAAGC
CACTTGGACTTACGATCGTGTGCCAGAAACAATATGGAACTTGATGACTTGGTTGATTT
TTGGTCGATTGGTAATCGAACTGCCAAGAGCTTAACGCGATTGGCCTTCATAATCTTTAC
GACTTGGCTCATGCAGACCGCGCCATTCTGCACCAAAGATTCGGTGTTCTCGGTGATGCC
ATGTACTTTCACGCATGGGGTATTGATTACTCAGACTTAACCCGCCGCTACTTACCACGG
GCCGAAAATAAAGGCTACGGCAATAGTCAGGTACTCATGCGTGATTACACTCAGGCAAGG
GAGATTGAAGTCATGCTTAGCGAGATTGCTGATCAAGTGGCTGGCCGAATTCGCCATCAC
CAAGTCCAAGGTGAGGTCATTAGCGTTGGCATTGGTTATGCTGATGCAGAAGAAGCTGGC
ACCTCCGGTTTCGGTGCGCAAATGAAGATTGATCCCACAAATCGCACAGACGATTTAATT
CGCGCTACTCGATTTCTCTTCCATAGTAAGTGGAACGGACACGCTGTTAGAAATGTCTCA
GTTCGCGTTAATCGCATCAGCCAAGCAAGTACAATGCAACTTAGTCTATTTGAATCAGCA
GAGAAGGAGGAAGCAAACGCGGCTCCTATGCTGTAATTACGGATAAAAGAATCACCATCA
TTAGGTTTTTCGTCTAACAATTTTAGGAAACTTCACTTTCTAGGTCGTAACTTTATTTTT
GCAATCTAGGGTTTTTAAATATATACATTTTAGCTCGTTTGTGTTTAATATTATAATCA
CAACTATACCAATGATAAATGTCTAACATAAATATACAAACATGTTGACAGAAGCTCTTG
AATACGTTTACAATTATTTCGTTCAGGCGAGCTTTGTTTTTGAAAAAGTATTAATACAAG
ATAACTAGGTTAGTGGCTGTTGAATTAGGCCCCCGATTTCGGGACCACGACAGTCACTTG
ATACTCGATTTTTATCGTTTGCTGGCTTGATCGTACATTGAACGAAATTGGTACAGAAAA
AAGAGCTAAGAGCCGCTCCAAATTAGCCAAAACGATTGCGGCGTCAATGCTTACGGCGAT
CGTTTCTGCAGTTTTAGCTGTTACCAGATCAAGTCCTAGTTTCCCTTTGATGAAGGCAAA
CTCACGCTCGATCTCACCTCGTCGATTTTCGGCTTGTCGGTCTGCCTTACGTTTGGCCGG
ATCGACCTGCTTCGGCCGACGGCCCAATCTAGGACCGCTAAGTTTGATCCCAAGATCTGC
GCACAGCCCGATATTCGCCCGAGTCCGATAAAGCGTATCAGCCAAGATCTCATCCGGGTA
TGTACCATACGTGTCAAAATAATGGTCGATCGTTGCTGGTAAGTCAGCACTTTCGTTAAA
CGCATTGAACGCAAACCGTTCAACGGCCACGACGCCATGACTGATCGATACGTCGATCTT
GGGCCCGAATTCGACCGGATCCTTTGCTTTGCCGCGAATGATCGGTCGGATCGCTGGTTG
ATCAAGGCTTACGATCCGATCCGCGACTCGGTGAGTGTGCTGTCGATACATTTCAGTTTG
TTGCTCATACAATTTTCGAATGATCGTTAATCGTTGTGTCTGCCGTTGATTCAATTGCCC
GCCTTGTGCTTGCAGTTCTTTGACGTAACGCAAGTCACGTCGGATGTACTGTAATTGAGC
CTTGATCTGCTTATGGGTCGTTTTCACCCAACGGCGGGGTTTACGTGAAAAGGCGGTCCA
CGTTTGGTGGGCCTTGCGCTTATAGGTACGCGGCGGTTTGACCGCTAATTGCTTGGCCAT
GGCTGCGATGAATCGCTCTAAATTGAGCCGCGCCTGATTGAGTAGCTGCGTATCCTGCGG
ATACTTGATCTTTACTGGGACCGCAGTCGCATCAGTGATCAAGATCTTCTGATGGCCAAG
TTTAGCTTGGAGGCGATCGCGGACAAAATCGCTAATGATGTTCGTGATCAACTCGGAAAG
CGGCGCGATCCGGCGCCTGAAATAGGACAGCACCGAAAATGAAAACGGTGCTTGCGGCTG
ATACTCTGGCAGGCCAATAAAATACTGATAAGCCGGTGTATCGCGGATCGCTGCGACTAA
CTCACGGTCCGATAGCTGAGTGCGCTGCTTGATCAGTTGGGCGCCATAAAGCAGCCGAAA
GGGTTTACCTGCCCATCCTAAGTTAGACGGGAAAGCCAATTGGTACGCCTCTTCTAGTTG
```

-continued

```
CGGCCACGGAACTTGGTCGGCCAGTTGGACCCACTCGTTATCTGGACTTAATGGGGTGCT
TAAGCCGCTACCAAACGATTTGATCGATAATTGAACGGCTTTTCGACGATAAACCATGAT
CCATGCCTCCGATAGGGTCGTGTCAAATGCAAACGAAATGAGCACGATCCGTAAATTCAT
ATGCATTCATTATACGACGATAACGGGTTCAACTCGCATCAAATGTGGTTATATCAAATT
ATTCAACAGCCACTAGGTTAAGATCTTCATTTAAGTGATATTCATTTGCAAGCAATTGAA
AATTACTCATCACGAAGAGGATTTCATTGGCCATATTGGATAGCACGCAAATCACTTGCT
TTAAGAAAATCAGTTCCTTTAATGAGTCTCTTAAAGGACGGGGCTCTCACTTGTACTCAC
AATCAATGTTAACTGGAGATCAACAATATGGTCATAGATTCCCATAATAACATTGACTTG
ACTATCTAAAGAGGCTTCTAACTTTGATATTGGTGGGGTTATTGGTTGCTTGGCTGTAA
GCAGATAATCTTAACTTGGGTTATTTTCATTGTGTTGTAAAGACATTTGTTATAAAGGCC
GAAGTTATCGCTTTGACTTGTAATAAATTATTTTTGATTGAGATATCAGAAAATAAACGG
GGGATAATAATGAAAAGATTATTAGGATTGTTCTTTGTGTTGTTAGTTGCGTTAGTATC
ATGGTCGGATCGCTTGGGTTCTATTCAACTCCAAAGATCGTTAAAGCCGACAGTACATCT
GTTACGGATGTCGACATTAATACCTATATTTCTAGCATGACACTTGATCAAAAAATTGGA
CAAATGTTTGTAGCACGAACCTCACAAGATACTGATAAAGCTCGTGCTGATATAGCAAAA
TATAATCTTGGCGGGCTGATTGTTTATGGTGTTGATTTCACTAGTGTTAAAGGGACAACA
GCTACAGAAGCTCAGAATAACTTCAAGATGAAGATGCAAGGCTTTCAAAACTCGGCAAGT
CTGCCACTATTGATTGGTGTTGATCAAGAAGGAGGGGCAGTCTCACGCTTATCACAAAAT
CCTCTAATTGCCAACGGCAGAAGTTTTCCTTCACCACAAATGGCTTATGCTAATGGTGGA
ATGACCAATGTAACAAAAGAAGCTAGTGAAGTCGGAACTATTCTAAAAAATCTGGGCATT
AACTGGAACTATGCACCAGTTGCCGACAGTACGCCTGACACCTCTAGTTTTATTTATGGT
AGAACCTTTGGTCAAGATTACTTGGCTACTGCAAACTATATTACGAATGTGATCCCTGCG
TGGCAAAATGCTGGCATTGCCGCAACTCTCAAGCATTTCCCTGGTTATGGATCCGCGATT
GATACGCATACGGATTTTGCAGTCGTTACAAAGTCTAAGGAGGATTTTGAAAAGAGGAC
TTGCTTCCCTTTAAGTCCGGTATTACAGCAGGGGCAGATTCTGTAATGATTGCACATATA
GTAATGCAAGCTGTTGACCCAGTGTATCCAGCATCATTATCACGGAAGGTCGTTACCGAT
TTGTTGCGTAATGAACTTGGGTATAATGGCTTAATAATTACCGATGCATTGGAAATGGGG
GCCATCAAGCAATTTGCTCAAGAACATGATCAAGTTCCTGTTGATGTTCTTGCTGTTGAA
GCAGGGAATGATTGCATCATGAATAACGATTATGAAACCGCTATTCCACAGATTCATGCA
GCAGTAACTAATGGAACTATTAAGGAATCAGAAATCAATGAACACGTTTTCCGTATTCTT
GATCTCAAACGCAAATTAGGGTTGTTAACTAAAGGACAACTTCAGCAAAAAAAGTTCAG
GTTGACAATGTTTCCTACAGCAGTGACAACAAAAAGGCAACTGTGAGTGGAACAGTTGTT
GATAGTGATTGGCAAGTTGGAGAACCATTATCGGTTAAAGACTCGACTGGGAAGGTCATT
ATTACCGCAGACGTTGGTGCCGGTGGTAAGTTTACTTTCGATGTTCCTACTAAGTCCCAA
GAACAAGTATTAACTCTGACTACTAATTTACCCAACATCGCTGATTCTCAAATAACTATT
AAGGCTGTGAGTTCATCGAATACTAACAAAGCTTTGCTAGAAAACTTGATCAACGCTGCT
GAACAGTTGGATAGTAATCAATATACTGTCAAGTCGTGGGAAGAATTACAAACTAAACTA
ACTGAATCAAAATCGATTCTGAACAATGATAGTGCTACACAAGATCAAGTAGACGCTTCC
GTTAATGCTCTACAAATTGCCCTTAAGCAATTAGTTCCTGTATCAAATAGCGGAAATAAT
GGTCAAAGCTCTAATGATAGCAGTAACCAAAGTTCATCTAGCAGTAGTGGCAAAGAATCA
TCCAGCAATAGCAATGCCAATATTACTAGTAAGGATCAGTCAGCTAAGGATTCAAATACG
```

-continued

AGGCCTAAAGACCATAGTCTTTTGCCAAGTACAGGTGAACGGGTGATGACGGGAATTTCT

GTTCTAGGGGTAATTTTAATAGCTTGTGTGACTATATTATATATTCGGAAAAAAGGACGC

AGCTTTTAATTAGTCTCTGCGTCAACTGGCGTTAAAAACTAGATTGAAGTAATAAAGTTA

CCACCTGGAAAGAGGCATGCTCATTGCTTGCAAGGGTGTCGACGTGTAATAGAAAAGTTG

GGG

SEQ ID 12 Position 325750 . . . 327159
TGGCGTGGGCAACGTGCACGTTTTCTAGTCGCTAAACTGTGAACAATGCTCGTGCTAAAT

GCAAAACTGAGCAAGGAGATGAACTATAAGCGGGGGACCCTTTGCTATTGAGGAGGAAGG

CGAAGTAGAGAAAGAGCGGTGATTTGAACTCGAAACAGCGGCGCCGCAGGCTAGCAGCAC

TGTTAGATTAATCGCCAGCAGCAGATACTAGACAGCTTCTTAAAGGCTTGATAATAGCGT

TGCGCCATTTCAATGGAACTAGTGGTCAAAATCGCATTGTAGTTGCCATGACCCAAACTC

GTTTTACGCGGGCCTTTTTGTAAAATATATTGAACAACTTGGTTAATATGTTCATCGGTC

TCAAAGTCAGCCGGAGTTAAATACGTTTCTTCCAAGTCCTTCACTGACATCGCTTGAATC

TTGGCTTGAATTTTCGCTTCATCAGCCGTACTCAGCAGGCGGCCTTGCTTATCACGACGA

GCTTTAACGCGCTGAGTTTCTTTTTCAAGGGCCCGGGTTATTAAAGCGTCTTTACCAATC

GTTGTCACGTGTTCCACATTAAATGGTAACACTGCTTGGTCCTCTAAGGCGTCTCGCAAG

TTATAAACATGACAGACTTTACCAAATAGCTCCTCCGTCGTAACTGCTAGATCACCTTTG

AGCTGTTTCTTATTTTCATTAAAAATGGGGGTGCCAGTGTAACCATACCAGTTACTATTG

ATAAACGCTGCTCGAATTTCCTTTTGCATCTTACCAAACTGCGACCGGTGGACTTCTTCA

ACAAAGAAGATCACCCGTTGCTTTAAAGTCTTACTAAAGCGGGATTGCTTACCGGTTGCC

AGCTGGACTTGCGTTTTTTGACCGCCCGATGGAGCTTTTGAATCGAGGTGACCAAGACC

TTACCGTCATTTTGTTGCAATTTACGCATTAAATCACCGGTGTTTTGGGCTTCGTTAATG

GCAATATCATCATTGGCAGCATAGGCACTAAAGTTGCTGGTTGTCTGTTCGTCTAAATCC

CGCCGGTCAACTAAGAAGATGACCTTATCGACACCAGGATCTTGCGCAGCTAATTTAGCG

GTTTTATATGAGGTGAGTGTTTTACCAGAACCCGTGGTATGCCAAACGAAACCATCCTGA

TGGTCATGAATCCGGTGCATCACGGCTTCAATCGCATAAATCTGGTAAGGCCGTAAGAGA

ATTAAGCTTTGCCGCTCTTGGTCGATGACTGTATATTCACTGACCATTTTGTGGGCCATG

GGAATATTAAGGACTTGGCGCGTGAACGCTAACCCGTTTTCCACGGGGTGATTATCCCGC

GTCCGCCAATTGAACAAAAAGGCTTTATTGAAATGATCCGGTTCGGCATTCGCAAAATAC

GCCGTACTATCCGGCGTCATAATCACAAAC

SEQ ID 13 Position 328723 . . . 329314
CGATCTAAAAGCTAAGTTATTTTCCAAGATATCAAACAACTTCTTAACCCAAGAATCTTC

CACACATAGGACAATAATGAATCCAAATAGATTCAGCTTTTTCCTGCAAACCGGGATCAG

TATAAACGTCCAGTACCGGATAATCACGCATTAAGTTCAGCTGCCAATGGGTATCATCTA

AATTAAAAAGATCCGATTTAGTGTCTCCCCTTACTACATTATGGCAATACACACAACTGT

TGTTATACATGCTTCCTTGCTTTTTGATTTTAAACTCCTCCATTTTGCATATTATAAGAA

GATTACTTCTACTTGATATATAGATGCTTTCCTTGCGAGGGTAAGTCAGACAAGGAAGCA

TTTCTAACTTGAGATACTTAAGCTTGTCTCAATAGATGTAGATAGCGGCTCCCCAATCGG

ATATTAACAGCTCAACTAGTCAAACCAGATATATAAATGTGACACAAGCTGGAATATATA

TCATTATCTAGATAATTCAAATTGAGCTAATAAAATCAATAAAGAAAATTTTAAATAACA

TTATTTTATAAACCCCTTTAGGATTTTCCCGATTTGATATTCTACGTATGTT

SEQ ID 14 Position 2002858 . . . 2005090
GAGTATCCAAAAATACGACGGGTATTTGAATAGGATACTTATTAAGCGAGAATGGTATTG

GAAATCTGTGGCAGCCACTCAGCGGAACCATACCTTTATCCCAACCCCACGCAAAAAAA

CATCAAGTAATCCGTCAGATATGATGACTTAATTGTGGGACAGTTCTAATATGAAGAAAA

CAGGTTAGATAATTGGGGTGAAAAGATGGCAACCTATTCGCAGATAGAACTAGACATAAT

CAAATCATTTAAAGGGCTGATGAAAGACCATGAATTCACTGAGATCTCAATTAAAATGAT

CGCTGAAAAAGCCGATATCACTCGACGCGGCTTTTACAATCACTTCTTAGATAAATATGA

TCTTGTCAGTACCATCTTTGAGCATGATCTTTTTCCAACAGTCATCAGTTTGACGAATAT

CAATGACTGGGATCAAGGGTCGCTGTTTATCGTGAATTATCTCCAAGACAATCGCGACTA

CTATAAAAAATTGTTGTCGCTTGAAGGACAAAACTGTTTACAGACAGACTTTTATAAATT

GACTGAGATGCAGATTGGGATCTTGATCCCAGAAATATTGGTCGGTAGGAAAATTTCTGA

CGAAGATCAGGCATTTTTAAGCGATTATTATTTTCACGCTTATATGGGACTGACTACCGA

ATGGGTCAAAGGTAAATATGGTTTTTCAACTCAGGAGTTCGTTAAACGGTGGAAAGCCTT

ACTCAATAATTCAATGCATAATTATCTGGACAACTACGCTCGATGAATTACACAGATTGG

ATTAAATGAGAAAGATGTTACATTTGTGCCAATATGTGAATTGATAAATATTTCACAAGG

AACTATTCTTTCCCTGTAAACGAAAGTTGACTTGAAAGGAGTTAGTTCTGATGAGTAAAT

ATAAAGTTATTATTTGGGGATTAGGAAACGTTGGTCGTTCCGCAGTGAGAATGATCGCGG

AAAGACAAAATATTTTTGAATTGGTTGCAGCCGTTGACGTTGATCCAAAGAAGTTAGGTA

AGGATGCCGGAGAAGTCTTTGATTTTGACAAAGTCGGCGTCAAAGTTTCAGATGATATTG

ATGCAGCCTTGAAACTTCCAGCTGACATTGTGCTCGACTTTTGCCCAACGGAAATGGACA

AACAAGGAACATTCATGCCTTCTGCTATTCGACTCGCCAAATCGCTCGATGCCGGTAAAA

ACGTTATTACCACGATTCCGGTATATCATGTTCAAGACAGTCAGCCAGAAGTATATGAAT

ATCTAAATGAACATGCTAAAGCACATAATGTTGCTTTTGTACCATTTGGACTTTTGCCAG

GCGATTATGCCTCATATATCCCACTAGTTTTGGCCGGGGCCATGGGCCACGTGGATAAAA

TTGTTGTTCAATCCGGTGAAGATGACTGGCACAACACATCAGGCTGGGTCGATGTCTTCT

CATATGGCGGCGATATCAATAAATATCCAAAACCAGACTCAGACGAAGATCTCTTGGCTA

AGTTCATTTATGCTTATTATTCATCCGGCGTATACGAGATGGCCGATAGGATCGGTCTGA

AATATGATACCTTCAAACCAGAGCATGAAGTCTTCACTGCACCCAAAGATTTGGAAACGA

TCAAGGGTACAGTCAAAAAGGGCAGCATTTATGCCCACAGATTTACCATGGCACTTTACA

ACGGCAACGAACAAGTAGCCGCCTTAAGTATGTTCATAAAGTTGATAATAAAGAGACAC

CAGAATTACCGATCAATAATACGATTCATATTGAAGGCTTGCCGTCAGTCGATGCGCAGA

TCGATGGATTGATCCCAGAAAGAGAAGGCTACGTTTCATCAGCCGCTCCAGCAGTCAACT

TGATCCCTAGCATTCTCGAGACCGACAAGACAGGTTATGTTGAAGTCTGCGACCTTCCAG

TAGTGATTGCCAGGCCATTGGATATTGGCGCAAAAAAATTAGTCTAGACTAGGCTTTCGA

AGCTGCTTTGACCATTAAGGTTGGAGTAGCTTTTTCATTTGCAAGTAAATCATTACGGCT

TGTGTATACGGTATACAAAATGGAGAAAACGCTGACTAGTTTATAAATCATTGAGACTTA

ACGGCCGGATAAATGCTGATCTGATTATAGAAATAACAACAAAAAGGCCACGCTAAAAAT

CATATTAATTATAATCGGGAAATTTATTAATAATATTCAAGAAAAATAAAAACCGTGGGT

ACATTATTTAAAA

SEQ ID 15 Position 2262750 . . . 2268615
TTTGAAACTAAGACGAAAGCTGCCATGTCAAACAAAGCCGCCATAAATGCCACTGTCACA

GATCCATCAGCCGCAATGCCAGCATCTTGCTGAAGTTCTTTAACAGCATTAAGGGTGTTA

-continued

```
TTCGTGAACTCATTATTAAAGTCTACTGGACTAATCCCTTTGCACCAGAAAGCCCCTTGA
ATGAGTTGAGCAATGTTCCCCTTATATCCTGGCTTCAGACTACCTACAACAGGTGCTAAG
GCGTTTTTGGTCGTCTCGCCAAAGCCTTCACCAATAGCACTAATACCGATTTCGTGCTGT
AATCCCATTCTTAGGCTATAAATTGTTGGCCATCCCGTTTGCCCGTTTTCTGGAGCTGCG
ACAAAGCCAGGAACGCTACCATACGTTTTGTTGAGCCATTTTTGAACGGCTCGTACTGCT
TCATCTGCCATTTTAAAGTCTCCTTTTTTGTTTTAGACAGCACGTCTGCCGTCACAAAAA
GCAAACATATGTTCGGATTCATTTCATCTCTTCAAAGCTTCGAAAGGCAACCCTGATCCA
CAAATAATCCTTTTATTTTGAACTTAGCAAAAAATGAGGCCCTCACATAGTGTTGAAGT
TGCCTCATTCTTAATGTCTATATTTAAAGTATTGCCACAACGATGGATCATCGAACGCTC
ATGGACTTGGTTAGACATGTATCGACGACTATGAAAATGTGGGCGCAAGCTCAATTTCAC
CTTCCAAATGTTTGTGCTATCTCATTTAGCGCTGGTTTTTTTAGGATAGACTAGACAAGG
ACTAATAATTTCTCAAGAATCCCGCAACTCCACTATTCATTCGTCGAAATCCCCACTGAT
ACTCTTGTCCTTGCACGTTCGACCAAGCAAGAATGTTTATTCCGATAACCGAATTGTTGC
CATCAAGTAATGGACCTCCCGACATGCCATGATACGAATTAATTTGTTGTGAAATATATA
TTCCTAGTGGGTCCTCTGAAAAGGGTGTGACAGTCCCACTTGATTGAACCATGACTCCTT
GAAGTTCGTACCCTGATTGCGGATCGCCAGGGAATCCAATGGATCTTGCTGCCATCGTAT
CAGCAGGGTTCGTATTTAAATTAAGACCCGCAGGCATACTACCAGACTTCATAGAGACAA
TTGCAGCCCCGTAATCATTCGAAGTAGCTGTTGAATTATTAATCCATGCCTGTGGCACTA
TCAATCTATTCAATACTCCGTAACCGACCCCTTGATGATTTGCTTGACTATCACCAAAGT
TAATAATTCCTCCAGAAATATAATGACCATCATATAACATGTGTGCTGCTGTCCCTATAC
GGTCTACTCCAATGCTAAATCCAGTACCGCCAGAAGTTCCACTGCTCAGCTCTGTGCCAT
TTGAGTTAGAGATGATTTTTTTATACGAACTGTCAAGGTATGGTGAGTTAATGACCATGA
CACCATTTGCCATCGAAAACCACGTGCTCAAAACCCCAACGGAACTGTACGGCGCCGAAT
TGGGGTTTGACACAGGTGATACCGTCCTCACAGATAGATGATTAGACGATTTATTCAGTT
TCGCAAGATATTCGGACGTAATTCCTTGAACTTTCTTTCCTTCTTTTAAATCCTGATATT
GATCAGGTGTATAAGCTTTGACACTCCCTTTAAAATCGGGATAAGAATACTGATATTGTC
GAATGATTTCATTCAAAAACTGTTGTGTTGTCGTCTGGTTAGTCAAAACAATATCATTCT
TTGGTAAAACATGGCTATTCGCTGCCAAAGGATTTGCCATACTATCAGCACTTACACTTA
CCGTTTGAACTTGAATTATCGCTAAGGCTGCAGCTATCATAGTGATATATGCCCATACTT
TTCGCAATTTAATTCCCCCTTTTTCTTAAAATGAAACCGCATTCACGGAGGCTTGTCAAT
GCTTTTAAAAAACAAACGTTACTTTTGGCTCATCTTGGCTGTCAGCATAATTGGAGTAAT
TGTTCTTGCGGTGTTATGGCGCATGAACCCTGAAGGAACGGCCTCAAATAAGTTTGAACG
TCCCACCATTACTATTAAAAAAGTCAAACTTATTAAGCACAGTAACAGTATTGCTGTCAC
ATTTGCTACCTCTCCAAAAAGCAAATATACGATAAGTGATCTTAAAGAGAATCAACTTTC
TTCTGGCATTTCGAATAAAAGAGAAAATACCGTTTCGGAATTAAAGCCCTCCTCCTCTAA
GCTTGCAATACGGGTTAAGCATAACAATAATATACAAACCAAAGTGGTTTCTGTTCCCAT
TGGTTATCATATTATGAAAAGTGCCATTTCAAGAAAGCCAATTCCTATGGGAGAAGAGTT
TAAGTACAATGGAAAGTCGCATGTTTTATTTAGCATGACCATTACCCCTAAAAAACAAAA
CAAGAACAGTATAAAAAACACCACTGCTTTTAACATAACGGTTAAAAATGATCACTACCT
TGTCCCTGTCGTATTAGATACCAAATACCTTACTGTTTCTGATTCAGAAGGTAACTCATT
```

-continued

```
AAAAGTAAAGCCATTCTCAAAAATTTCTATTCCAGCAAAAAAGAAAAAGACCATTGCAAT

AACTATTGAGGGCGTTCCCGCAAGCTCTGCCAATGGTCTAGTTATAACGTATAATACTGT

CGATTTAGACTTACCAATCTCCTTTATAAATTCCTGAAATTACACTAACTGTCCCCCACC

TTGACAGTCAGTACACTCAAACTGTCTCTTATGCTTACAAACACGTAATTTAGGCGGTTT

TTAAGCAAAAGTCGTTAGTTTTCATAAATGTTATCTTATACTCTAATGAGATCTAGCTTG

TGATAATAAGGCTGTTTTTCTTTGACAGCCTTATTAAGCACACTAATCAATGTCAATTCG

AAGTTTTTGGTTTCCTACTTGGCCAACTTTGTTATCAGAAATTCCAAAACTCATTGCCTC

CCGCCACCATATATTTATCGAGCCATTTTGAAAATGAAAAATCGAAATATCGGTCTGCTT

CTATTCCGGGATGAGTTAGATATGATTTTCCTAACCGATACTTCTCTATATCAATATACA

TATCTCCGACATCCCTTATATGGAGAATGGGTACTTTATTTACAAAACTTTTAGGCAGTG

CCTCTTTTTCTTTAATCATTTTTCTAATTGAATAGACTTCACACGTATATCCCATAGGAA

TCCCTTCGATTGTTGTGTCAAATAAAAATAGTCCATTAGTAATCGAGAGAAACTCAATGT

AATCCTGTGGAAGGTTCCACCTTTTTATTTTTCTATATCATCAGCGTGTGCAGGAGGTT

CTATCTTAAAAGAAACATTTTGCACATCTCCATCTAATTGGAATGTTGAGAGCGCTTTTT

CCCCATTTTTCGTCACCTTTATTAAAGAATTAATTCTTCGCCGAATTAGAGATTCCAAAT

GAGTTCCTCCTCAATAGTTGTTAAACCACGCGGTGATCAACCGATGATTTGGTGTTAACA

CCGGCATCAAATTATTAAAGTCATTTGTTCCGCCATAAACTCTCGGGCGAATATGATGCA

CTTCTCGAGAACTCCAAAAATCTGCAGATTGATTGCCATATGTTTCACTGAACGTTTTAA

TATAAATATATCTATCTTTTGATGACCAACTAGGAGATTTTGATAACTTAGTCCAGGTAG

TATTAATAGGTGTTTCTGCATCTTTTTTAGACACGGGATCAACATATTCAGGGAAATTCT

GTCCTATTTTATTTTGTAAATAGATGGCCGTTGGTGGGATTGGTTTTACATTAGCCGCTC

CATTAACTCCTATAAATCCAACAGCGCCAGCAACGTTAAAAAATGTGGTTTTGGCTGGCA

ATTCTGTAAAACCAAGTAATCCTGTTTGCAAACCGCCTATTTTGCTAATGGGTGCCAGCG

TATTGGCATTCACCGGACCTGCAAGGGTAGGCTCAGTATTAAATTCAATTTGCACATCAA

CTGCGGCTGGCGGGACACCCTCAATAGAATCAATCCAGAAATTGACTCTGAATTTTCCGG

ATATGTATTCTTCCGATAAGTGCCAGGTAATATTTGTAACAGGAACTTCTGCACGAGAAC

TTATGCCATTGCCATGACTATTATTCAGTACCACTTGTTTTCCAGAAGCGATAATTGGTT

GTCCATTTTCTGGATTACTTCTTGATAACTTGTCAGCATTGGTCAGTTGAGTATTGTTAT

CGCTAATACGGCTTTCAGTTGAAACAATTTGATTTAAAGATTGTGTTGTGTCTGCGGATA

CAATTGTTGAATACCCAAGCAAATTGACTAGAAAGAGCCCGAATATTAGCCCAATAACTT

TCCACTTTTTCACGCCTATTATCTTCTTTCCAAAGTTCTTCAGTGCCTGGCAATAACTGT

ATACATTGAGCAGTATAGTCGCTATTTTATAGCTGAACAACTCATAAAGCTCAATTATTA

TTAGCCTATAAAACCACTGCCTAAGTGAATTGATCTAGAACGAAGCACGCCGAAGAAGTC

GCTAAATGTGCTAAGAAAAATGTGCTTGAATAGCTCAAAAGTAATTAGCGTCTCCATTGA

AAATCCGTTATTTTTAAGTGATCTAGTGTTAACTATGAATCCCAAATAAAAAGCAAAATC

CGTAAATGCCAAATTTTCCTTTTTGACGTTTTTCTACTGTCGCGAGATTTGCAAGTGTAC

GTACACTTACGATGAATTGACAGAATCTCAGCTGCGCTGATCGTCAATTTTGTTTGGGGG

CACGCCCCCAATCCCCCTGTTATTTTGAAGGGAGGTGAGTCCCCCTTCAAAATCAAAATT

TAAACAGCATCTGCCGCCATCTTTTCGCTGACCTTCTCACGATGTTACACGTGGTGTTGA

CACCCACTTGCATTTAGAGTTTCATTCAAGTTGAACATTGTGTAATATATGAGTTGCATT

TGATAAACATATCAGTTGCTATTTGTGCAACTTTAAAGCTTCGGCTAATTCAACGTTCTG
```

```
TTAATTTACAAGCATCTCGACAGTTTCTGTTAAAGCAACATCTACGCTTCAATTCGAGCA

ACTCACTATACGTATGCCGAGTTGCAGACAAGCTACTATATAGCTGTACGCGCTGAAACA

CCAAAAATCGTTCGTTTATGCCCAATAAGCGAATAATCTTGCTCAGGTGTAGTAAAAAAC

TGTTTACGTGTAGTGAATGGCGCTAGCCCTTGTCGTAACTGGCATCATCCACGTGTAGTA

AAACGCGTTTTACTACACGTTCGTAATTTTTTCACGTGGAGTAAATGGCGTTTTACTACA

CCTTTTGACCCCAACGTGCTATCACGACAAACCAAACCGCACTGCGGTTTACCCCAATTT

TGGGGTCAGTTTTGCCTTATGCTCTTTCATGATTTTAGGCGCGTTCCAAGCAGTCTCAAA

AAGTGGTCGATCCAGGCGAGCCGATTTTTGAGAAGGATTGGATAGCAACTCAATTTATTT

TGATCTTTTGCTTGGAGAAAAACGTTCACGTTTTGACCAGGGCCGTCGCAACTGTTGACC

AAAACTCGTCCGGTAACGTGACGCTATTTAAACGCCGCGTTGGTTTGCTAGACGACCATT

CATCATCACCATTCAGGAGGTTTTTGAAATGACAAAGCAAGACGAAACACACCGGGTCAT

GTTCACTTTGACCGATCAGGCGATTGCAAAATTGAATCAGCTGGTCGCAAAAAAGCAACA

GGAAGTGAATCAAAATCCGGAACTGGCTAAGTACCATGTCAGCGTGACCAAATCAAATAT

CATTGAGGACTGGTTATCAAAGCAGTGAGTTTAAAAAGCGCTAAAGGGCCTGTACTAGCG

TTTCTTACTCTGGTGGGTATAATTAATGCTCTCTACATCAAAAACG

SEQ ID 16 Position 2776965 . . . 2787971
GCCACGAACCTGTAGCCGTTTGGATGAAGCCATATAATACTGGACCAACCGCCGCAAATA

AGTAGCCGACACTTTGAGCAAAATCAGGAATACTAATCTACTTTGCCCTTAAAAAATCTT

GAGATGATCCATATCTTGTTTTGCCTTCATTACTGTAGTTGGTCATAAGAAGTGCCCTAC

ATTCATTAGATTACTTGTCTAATAATTGTAGGGCACTTGGGTTGAGAAAAATGATGTTAA

CTAAGAATGCAAACGAACTAAAATCTTTGCTTGCTTTTTATCCTTTTCTAAGGATTCAAT

TCCTTCTGAAACTAATTCATTTAATTCAATCTTTTTTGTAATGACCTGTTTGAATAGTGA

ACGATGGGTATCTATAATCTTAATTACTCGATCGAAGATATTGGCATATCCATAAGATGT

TAATAAACTACCACCTTTTTTAAGAAGAGCTCTAACATCTACAACTGGTGGATGTTGAAA

TAATGCAATCACGGTAACCTTGCCACCATTTTTAAGAGCCTGAATGGCACCAGTAAGTGT

GGGTTGTACACCGGCGCAATCAAACGCAATATCCACTCCCTGATTTTCCGTGATAGTGCT

GATAGCGTGAGCTAATGACTTTTGACTATCAGCACGTATTGGGTATTGAATTCCTAATTC

ATTTGCTAAATTCAAACGTTCCTCTGACATGTCATTTATTATGACGTGATGTGCACCAGA

AATTTGTGCTATTAAGGCCGTGAACAATCCAATTGGACCAGCACCTTGAATTAAAACATC

ATCTCCAGGAGACACTCGGCTTGCCATAACTGCCTGTGCAGCAACTGAAACTGGTTCAAC

TAAGGCCCCTAAATCAAGCGGAAAGCTAGCTGGTAAGAGATGTGCAAAGGTACTTTTTAC

ATTGCACTTTTCAGCTAAGCCACCGTTAGCCGAAAATCCTAAGAATCCTGCTGATTGATC

ACTACCTATAGCATGTTCACACCAATTATAATGACCAGAAAGACATTCCGGACATTTTCC

ACAAGCAATCATTGGTTCGACTGCAACTTTATCTCCAATTCTTAATTTAGATACTTGTTT

TCCAATTTTAGAAATCGTCCCAGAAAATTCATGACCAGGAATTAGCGGGGCTTGCATATG

GGTTAGCGGATGAGGTATTGTCGCCAAATCCATACCCTCTAAATATTCATGAATGTCACT

ACCGCAAATACCATTAAATGCAACCTCAATTTGAACTTCATCTGGTGCGGGATCAGGAAT

ATTTCTTTTTTCAAAGCGGATATCCTTAGGACCGTAAATAACAGCTGCCTTCACCATAGT

CATAGTGCTTCGCTTCCTTCATGTTCAATATAGCACAATCGTATATAAAATAGTGAATAG

ATTTCAGTAATGAAGTTACCATCTTGACTTAACAAAAACTTGCTAACTGATTATATGAGA

AACTTTTACTTGAAACATTTTTGGTGATTACCATTAATTCCCTCGGACATATTTTGAAAA
```

-continued

```
ACCCTATTTGATGCTGATTGCAAATTATTTTATGCGTATTTATTAAGGGTTTCTATGTTG
AAGTATATAGCAAACTTGTTCAAGTAACTGACTTTCACGTGGGCTTTAGCCAAGAGATGC
TGAGCAGCGAACCCAAGGGGTGTTACTCGCCCACGCAAAAAAGAAATCCAATTGCATTCC
AGTATGAGCGAGAAGCAAGCCATTAAGACGCTGATTCATGAACTCGCGCACAGTGAATTA
CATTGTGATCCGAAGTTAAAATTGGATCGTTCAACCATGGAATTGGAAGCTGAAAGTACC
GCGTTTATCGTTTGTCAACATTTGGGAATTGACACGAGTGATTATACGTTTCCTTACCTT
GCTGTTTGGTCGAAAGATAAGGATCTTTCCCAGCTCTCCAAAAGCTTAACGCGTATCCAA
TCCACCGTCGAAAAATTCAATAAAACCGTCGATCAAAACCTTGAAAAGATTCGTGAGAAA
CCGTTGACGCTTGATCAAAAAATAGAACGCGCTAAAACCATTGCGACAACGGAAAACATC
GCAAAAAAGAGCAAGGGCTGGTGCAAGCAACGCAGGAGAAAACACGCTAACCCATTTGT
TGAATACTCTCACTCAAGAGGACACTCCAGCCCTTGATCACCCAAGAAAGGAATTACCAA
CATGAAAACCATTGACGAAATGAACGAATTCGATCGTGACATTATCTTACTTCACCGCAA
GTCTGTGAGCGAAGATACACCGCAGGCAATTCTTGTGAAAGTGAAACAGATTCGTAACGC
AATTGCCGACGAAAAGGCGGGTAAAGAAGATCCAATTGAGAAAGAATTTACACTCGAATG
TTACGACGAAGCAATCAGAAAACTAAGGGACCTTTCGGTCGCTGATTATCAGTTGTGGTT
GCGTCAAAACAAAGACCTGGAAGGGTTTGAATTTTGATTTTGAAGGGTGTCGTAGACCCC
TTCAAAATAACGGGGGATTGGGGGCGTGCCCCCAAAACAAAATTGACTATCAGCGGAGCT
GATATTGGATCAATTTATCGCAAGTGGACGTCCACTTGCAAATCTCGCGACAGTAGAAAA
AGCCCCAGAAAAGCAAATCTGAAAAAATGTAACAGGCACTTGATATCAAGTGCCTTATTG
TTTCTAGGATCGCTAAAAATAACAGGAGGTGGTTACATGAAGCAATCTGATGAACACCGC
ACGCGTTCAGTGAGAAGCACTGTGCGTATGACCCCAGAGGAGCGTGCTTGGGTTGATATG
AGAAGAGCCTCTGTCGGCAATCCAAAGTTCAATGCATTTGCCTGTCGCGCACTCACGACG
AGCAAGATCGTTCATGTACATTTTACTGATACTAAAAAGTTACTTAGACAGCTGTCAAGA
ATTGGGAATAAGGCTCCTATGCTGTAATTACGGACAAAAATAGTTTGTGCGATAATTACA
GCATAAGGGCCTCTAGGTCGGAGCCCAGGAGGCGGAGACCGCCGCACAGCCCAACCCCAC
GCCGAACCGGAGGCCAGCCCGCCCGCACCGCGGCCGCAATCATCCACCCAACGCCCCCCA
AGTTTTTGATAGCGGTAACAACGCCTGTGCGCTTGTCGTGGCCGGCCTTTTTTCATAAGG
TTGGAGGAGAAAGGAAGGGTGGTTATGGGCGCTTGGTATGAACACGCAATTATTTACCAA
ATCTATCCAAAATCGTTTCAAGACAGCAACGGCGACGGCATCGGGGACCTGAACGGGATC
CGGCAACGGATCCCGTACCTGCAAGCCCTCGGCATCAACACGGTGTGGCTGAACCCGATC
TTCGTCTCCCCACAGGTGGATAACGGCTACGATGTTGCCAATTACTTCGCCGTGGACGAA
ACCATGGGTACGATGGCCGACCTGGAGGCGCTGATCGCGGCTCTGCACGCGGCCGGCATC
CGTCTGATCATGGACTTTGTGCTAAACCACACCTCGGATCAGCACCCGTGGTTCCAGGAC
GCCATTCACGCCAAAAATAGTCTGTACCGCGACTACTACATTTTCTCTGGCCACGACGGG
CAGCTGCCAAACAACTGGGGCAGCTTCTTCGGCGGATCGGTTTGGGCGCCGGATCCGGCG
GGAACCGGGCAGTCGTATTTTCATCTGTTCGACCGGCGGATGCCGGATCTGAACTGGGCC
AATCCCGAGGTGCGGCGGGCGATGGGAGACGTCGCCACGTTCTGGCTCGGCAAGGGCATC
GACGGACTGCGGCTGGATGCCTTCATCCACATTGCCAAGGCCGATCTGGGGCAGGATTAC
CCCCTGGCTCCGGGGCAGCAGACGCCGGTGGTGGCGGAGCCGTTTTTCTCCAACCTCCCG
AAGGTGCAGGAATGGCTGCGGCCGTTCTGCGACCGGATCAAAACCGACTACCCCGACGCG
```

-continued

```
TTTCTGCTCGGCGAGGCGGCATCGGCCAACGTTAACCTGGCGGCGGATTACACCGCGCCT

AGCCAGCACCTGATGGACAGCGTGATCACGTTCCGCTACTTCACCGAGGACGAAAGCGGC

CTGGATCCGCGGCTGCCGGCGCAGTACCAGCCGCGGACGCTGGATTTCCCGGCGTTCAAG

CAAACCCAGGCGGTGTGGCAGCAGACCCTCGCCGGGGTGTCGATGCCGACGCTGTACTGG

GGCAACCACGACATGGCCCGGCTGGCGACGCGGGTGGCCAAAACCACCACCCAGGCGCGC

AGTCTGGCCATGCTGATGTACCTGCAGCGCGGCCTGCCGGTGATCTACTATGGCGAGGAG

CTCGGGCTACACAACCTGCAGTTCGATCACGTTGATCAGTTTGCGGACGTTTCGGTGGCG

CCGTTCGTGGCCGCGGTCGAGGCCACCGGGCAGTCGCGGAGCGCGGCGCTGGCCATGGTG

TCGGCGACGCACAAACTGCCGGCACGGGGGCCGATGCCTTGGACGACCGGGTTGCACCAG

GGCTTTTCCAATCACCTGCCGTGGCTGGTTGGGCGCAGCGAGGACGTGACCAGCGTGGCC

GCGCAGCAGGCCGATGAGGCCAGCATGCTGCACTTCTACCAAGCGCTGATTGCCCTGAAG

AAGCAGCCGCTGTTTCAGGCCGGGCATTACCGGCTGCTGACGACGGCGCCGAACCTGTAC

GTCTACGAACGCACGCTGGCCAGCCGGCGGGCCCTGGTGGCGGTGGCCTTGGATGAGCAA

GGCGCCACCTTCACCGTGCCTGAAGGCCTGACGACCGTGGCGCTGGCCGCCGGCGATTAC

CAACTCGAAGGTCAAACGCTCACGCTTGGCGCGAACGCCGGCGTGGTGTTAAACGAAAGG

GGAACTCGATAACCATGCAACTTGCAGCATTACGGCACCGCCCAGAAAGCGAAGATTGTT

TTTTGTACACTCCAGATGAGCTGCGGCTGCGGCTCCACACAGCCAAGGCCGACGTGCAGG

CGGTCATCGTACTGTACGGGGATCCGTATGTCACCGCGCCGAACCCGACCACCGGAGAAC

CGGAATTCGCCTACCAAGAGGCGGCGATGATCAAAACCGGCACCGGCCAAACCAGCGACT

ACTGGACCATCAGCCTGACCGCGCCTTATCACCGCCTGCAGTACCAGTTCCTGGTGACCG

GTCAGGACGGCAACACCGTCCTGCTCGGCGACCGCGGCTTGCGGGCCGACAGCGCCGCCA

ACCGCCGGGCCGATCTGTTCCGGGTGCCGTACTTCCACGCCATCGACACGGTACAGACGC

CGGCCTGGGTCAAGGAAACCGTGTGGTACCAGATATTCCCGGAACGCTTCGCCAACGGGG

ACAAGACGAACGACCCCAAGGGCACCAAGCCTTGGCGTCCGGCGGATCACCCGGGCCGTG

AGGATTACTACGGTGGCGACTTGCAAGGGGTGCTGGACCACCTGGACGACCTGCAGGCGC

TCGGCGTGAACGGGCTGTACTTCTGCCCGGTGTTCACGGCGATGTCGAATCACAAGTACG

ACACCATCGACTACTTCAACATCGACCCTGCGTTTGGCGACAAGGCCTTGTTCGCCGATC

TGGTCAACCAAGCGCACCGCCGCGGCATGCGGGTGATGCTGGACGCTGTGTTCAACCACA

TGGGCAGCCGCAGCATGCAGTGGCAAGACGTGCTGAAGTTCGGTCCGCAGTCGCGCTTCG

CCTCCTGGTTCCACATCAACCGTTTTCCGGCGGCGCCCTTCGCCGCGCCGGAACAGGGCG

GCGTGCCGCAGTACGACACCTTCGCCTTCGAACCGCACATGCCGAAGCTCGACACCAGCA

ACCCGGCGGTGCAGGACTACCTGCTTGAGGTGGCGACGTACTGGATCAAACAGTTCGACA

TCGACGCCTGGCGGCTGGATGTGGCCAACGAGGTGGACCATCACTTCTGGAAACGGTTCA

ATCAGGCAACCAAAGCGCTCAAGCCCGATTTCTTCGTGCTGGGCGAGGTCTGGCACTCCA

GCCAGCCGTGGCTTAACGGGGATGAGTTCGATGGGGTCATGAACTACGCGTTCACCGAGC

AGATCGAGGCCCACTTCCTGACCGGCAAGCTGAGTGCTCCTGAGCTGACGGCGGCGCTGA

CGGATCAGCTGATGCTGTACCGCGACCAAACCGACCAGGCGATGCTGAACATGCTGGACT

CGCATGACACCGCGCGGCTGCTAACGGTGGCCGGCGGCGACGAGGACCTGGCCCTGCAGG

CGCTGGCCTTCACCTTCCTGCAAACCGGGATGCCGTGCCTGTACTATGGCACGGAAATGG

GCATGGCCGGAGAAAACGATCCCGACTGCCGGCGGCCAATGGACTGGGCCCAGCTGAAGG

GCCCGATTTGGCAGCGTGTGCAGGCCCTTGTGACCTTCCGCCGCGCCCAGTCGGCAACGC
```

-continued

```
TAGGCACCGGCACCACGGCGCTGAGCGTGACCGCAGCCGGGCTGCTTAAGGTAACCCGCA

CAGGTGAGCACACCGTGACGGCGTATTTTAACACCACCAAGCAGATGGCGACACTGACCG

TCAGTCCATTACTGGCGCAGGGTTACGCCGGCCAGCGGCTGGCGCCAACCGGGTTTGCTG

TTATGGTTCAGTAAGATTATGTTAGCGGTAACAGGCAATTTGACCTTTTAAAAGCGTTTT

CATATTATCATAATCAAAAGTGTAGAAAAGTTCAGGTGGCGCAATTCACCTCCCGAAAGT

GAAGGATGCAAGATGAAACGGATATTTGAAATCGACCCGTGGCTGGTGCAAAGCCACCAA

TTGAACCCCAACGAGAAACGCCTGCAGGAAAGCATGACCGCCATCGGCAACGGCTACATG

GGTCTGCGCGGTAACTTCGAAGAAGGTTACAGCGGTGATCACCTGCAAGGCACGTACCTC

GGCGGCGTCTGGTTCCCAGATAAAACCGTCGTCGGTTGGTGGAAAAACGGCTACCCGGAT

TACTTCGGCAAGGCGATCAACGCGCCGAGCTTCATCGGCATGGCGCTCACCGTGAACGGC

GAGCGCGTCGATCTGGCCACCAGCGTCTACCGCGATTTCACCCTCACGCTTGACCTGCAC

CAGGGCCTGCTGACCCGGAGCTTCGTGTTCGAGGGCAAAAAGGCCACGGTGCGCTTCACC

TTCAAGCGTTTCCTCAGCAACGTAATCAAGGAGGCGGCGCTGGTGCAGCTCACCGCCGAA

AGCCTTGTCGGACCGGCCGAGCTGACGGTGGCCGCACAGCTCGACGGCAACGTCACGAAC

GAGGACAGCAACTACGACGAGCGCTTCTGGGCACCGCAGGGGAAAACGCCGCGGCAGGC

ACCATCCAGCTGCAGACCAAGCCCAACCCGTTCGGGGTCCCGCAGTTCACGGTGCTGCTC

AAGCAAAGCCTGCGCCAAGGGGCAACCCTTTTACCCGGCACCGTGACCACCAGCACCGGC

CAGCTGACCAGCACGGTCACGCTGCCGCTGGCGCCAAACGTGCCGGTCCAGCTGGAAAAG

GACGTCATCGTGGTCACGAGCCGCGACGTCGCCCCTGAGGCCCAGGCCGAAGCGGCCGCG

GAGCTGATGACACAGCTGCAGGGCCAAAGCTTTGCGGCCCAGCTGGCGGCACACACCGCC

CTGTGGGCCAAGCGCTGGGCCCAAAGCGACGTGGTGATTGAAGGCGACGACGCGGCCCAG

CAGGGGATCCGCTTCAACCTCGCCCAGCTGTTCATGACCTATTACGGCGACGATAAGCGG

CTCAACGTGGGGCCGAAGGGTTTCACCGGCGAGAAGTACGGCGGGGCGACCTACTGGGAC

ACCGAGGCGTACGTGGTGCCGATGTACGTCGCCGCCACCCCTCCGGCCGTGACCCGGGCA

CTGCTGCAGTACCGGCACGACCAGCTGCCCGGCGCCTACCACAACGCCCAGCAGCAGGGG

CTCAAAGGGGCCTTGTTCCCGATGGTGACCTTCAACGGCATCGAGTGCCACAATGAATGG

GAAATCACCTTCGAGGAGCTGCACCGTAACGCAGCGGTCGCCTTCGCGATTTACCAGTAC

ACGGCCTACACCGGCGATGAAAGCTACGTCAACCACGACGGCATGGAGGTGCTGGTGGGC

ATCAGCCGCTTCTGGGCGGACCGGGTCCACTTCTCCAAGCGCGCCGGCAAGTACATGATC

CACGGCGTCACCGGGCCGAACGAGTACGAAAACAACGTCAACAACAACTGGTACACCAAC

ACGATGGCCGCCTGGTGCCTGGAGTACACGCTGGCCCGGCTGCCGAAGGCCGATGCCGCC

ATTCAGGCCAAGCTGGCCGTGAGCGCCGCCGAGCAGCGCCAGTGGCAGGACATTATCGAC

CACATGTACTATCCGGAGGACAAGAAGCTGGGCATCTTCGTCCAGCACGACACCTTCCTG

GATAAGGACCTGCGGCCGGCAAGCTCGATTCCGGCCGACCAGCGGCCAATCAACCAGCAC

TGGTCCTGGGACCGAATCCTGCGGTCGCCGTTCATCAAGCAGGCGGATGTGCTCCAGGGC

CTGTACTTCCTGAACAATCGCTTCACCCGCGAGCAGAAGGAACGCAATTTTGACTTCTAC

GAGCCGCTGACGGTGCACGAAAGCTCGCTGAGTGCCTCGATTCACGCGGTGCTGGCCGCC

GAGCTCGGTAAGCAGGATAAGGCCGTTGAACTCTATCAGCGTACGGCTCGTCTGGACCTG

GACAACTACAACAACGATACGGCAGACGGTCTGCACATCACCTCGATGACCGGCGGCTGG

CTGGCTATCGTGCAGGGCTTCGCCGGCATGCGCTACGACCACGATCAGCTGCGGTTCGAT
```

-continued

```
CCGTTCCTGCCGAAGCAGTGGCAGGGTTACCAGTTCCGCATCAACTACCGCGGCCGGGTG

ATCCAGGTCGCGGTGGGGAAAACCGTTGCAGTGACCCTGCTGGCCGGCCCGCCGCTGACC

GTCATGGTTGCCGGCCAGCCGCAGCATTTGGAGGTGAGCGCGCATGCTTAAAGGATTGCT

GTTCGACCTCGACGGCGTCTTGACCGACTCGGCCAAGTTCCACCTGCAGGCCTGGAGCCA

GCTGGCCACCCAGCTGGGCATCACCCTGACGCCGGCCGAGCGCGAAGGCCTGCGCGGCCG

CTCGCGGCTGGACTCGCTGAACCTGATTTTGGCGGCAGGCGCCCAGGAAGACCGGTTCAG

TGCCGCAGAGAAAACGGCGCTAACCGACCAGAAGAACGCGGTGTACCTGAAGCTGATTCA

GACGATGACGCCGGTGGACATCCTGCCGGGCATTCCGCAACTGCTGAAGGACGCGCAGGC

GGCCGGCCTGAAAATGGCAATCGCCTCGGCGTCGCGGAACGCCCCGACAATTCTTGACCA

CCTGGGCCTGGCCGCCAGTTTCGACGCCATCGTCGATCCGGCGACCCTGCACCGCGGCAA

GCCCGACCCGGAGATCTACCAGCAGGCGCAAGCGCTGCTGGGGCTCCAGGCCGCCGAGGT

GATCGGCTTCGAGGATGCCTCGGCCGGGGTCGCCGCCATCAAAGCGGCCGGTCAGTTCGC

GGTTGGCATCGGGGATGCCCGGCTTCTGGCCGCAGCGGATTACCTAGTGAAAGACACGGC

GGCCCTGCAGCTGAGCCAGTTGCAAGCGGCGTTCGCCAAAGAAAGTGGGGAGACTAATGG

TTGAAATCGACTTGGACCACCTCTACAAGAAGTACGACGACGGCGAGGATTACTCGGTGG

TGGACTTCGACCTTCACATCAAGGATAAGGAGTTCATCGTGTTCGTCGGCCCCTCGGGCT

GCGGGAAGTCCACCACGCTGCGTATGATTGCGGGGCTGGAGGACATTACCAAAGGCGAGC

TGAAAATCGACGATAAGGTGATGAACGACGTGGCCCCCAAGGACCGCAACATCGCCATGG

TGTTTCAGAACTACGCCTTGTACCCGCACATGTCAGTGTACGACAACATGGCGTTCGGCC

TAAAGCTACGGCACTACAAGAAGGAGGACATCGACAAACGCGTGCAAAACGCGGCGGAGA

TCCTCGGCCTGAAGCCGTTTCTCGACCGGAAGCCGGCCGCCTTGTCCGGGGGCCAGCGGC

AGCGGGTGGCCTTGGGCCGGGCCATCGTCCGCGACGCCCCAATTTTCCTGATGGATGAGC

CGTTGTCGAACCTGGACGCGAAGCTGCGGGTGTCCATGCGGGCGGAAATCGCCAAGCTCC

ACCAGCGCCTGAACACCACCACGATTTACGTGACCCACGACCAAACCGAGGCCATGACTA

TGGCCGACCGGGTTGTCGTCATGTCCGTTGGCCACGTGCAGCAGATTGGCACCCCGGCCG

AGATTTACCAGAACCCGCGGAACCAGTTCGTGGCCGGGTTCATCGGGTCGCCGGCGATGA

ACTTCTTCAACATGACCTACCAGGACGGCTTCGTCAGCGACGGCCAAAGCATTCGCCTCA

AAGTGCCGGAAGGCCGGGCGAAGATTCTGGACGACCAAGGGTACAACGGCAAGGAAGTCG

TGTTCGGCATCCGGCCGGAGGACATCCATTCGGAGGAGGCCTTCCTGGAGACCTGGCCGG

ACGCGGTTATCAGCTCAACCGTGTCGGTGTCAGAGCTCCTGGGCGCCACCGAGCAGCTTT

ACCTGAAGGCGGATGACACCGAGTACGTTGCCAACGTCAACGCGCGCGACTTCCACAATC

CCGGGGATCATGTGAAAATGGGCTTCGACGTCAACAAGGCGCACTTCTTCAACAAGGACA

CGACCATGGCCATCGTGGCTAAGCCGATTCCGCTGGAAGGCTGAGGAGGTGAGTGCATGA

CCCCATGGTGGCAGCAAGCCGTCATTTACCAGATCTACCCGAAGAGTTTTCAGGACAGCA

ACGGGGATGGCATCGGCGATTTGCCGGGGATTACCAGTCGCCTTGATTACCTTAAGCGGC

TGGGCGTCGATGCCCTTTGGCTGAGCCCAGTGTATGTGTCGCCCGGCGAGGACAACGGCT

ACGACATCGCGGACTACGAGGCCATCGATCCCCAGTTCGGGACGATGGCCGACATGGACG

CCTTGATCGCCGCCGCCAAGCAGCGCG

SEQ ID 17 Position 2793833 . . . 2794809
CCCGCGATTTTGGCGTGATTGGCTTCGACGGGGTATTCCTGGACCAGGTGTCCAACCCCA

AGCTGACCACGGTGAAGCAGCCCGTGCAGCGCCTCGGCGAACTGCTGGCCCGCATGCTCC
```

```
                       -continued
TGCAGAAGGTGGCACAGTCCGGCGCCCAACAGGGGGAGCTGCTGGTCGATCCTGAGCTGA

TTGCTCGGGACACGACGCGAAAGTAGATCGGATTTCAACTGTCCTTACCGCTATGGTAGG

GCCAGTTTTTAGGCTCTATGTCAAATCTAATTCATAGCTAATAGTTGATTTGGCAACGCC

TAAGGCGTCAGCCATATCTTGGTAAGTATGATGGCCTTCACTGACCAGTTGAGCTAGCGC

ACCACGTTGAAAACGTGATAAAGTAGAAGTACCCAAAGTAATCACTCCTTATAGCTGGTT

GGAATTAACTACTCCATTGTAAGAGATTGCTTTGGGCCTTTTTTATTTTTGTTCGGATT

AATTATAGAATTTGTCTAATTAGTTGAAAATTCTTAGGGTTGCCCATATATCTTTTAGTC

TGGTCATTAGTTTTTATGTTTGATCTGCTTTTTTCTGATCGCAAACACCCACAACTGCGA

GTGAGTCCTTTTTGAAGTCGTTGACTGTCAACAATACATTTATTTCCACATTGACATTGA

CAGAGCCAAAGCGCGTTGCCATTAGAACTGCTTCCAAAAAAGCTAATAACTGTGAGTCGC

CCAAACGTTTGATTAGCTAAATCGATACGCTTTTGCATACTAATCCTCCCGCTTGATAAG

AAGGTACTTAAATAGTTGCTTTCAATTGATCTAATCGCCATTGGCACCATGAAATAAAGG

CTAATTCGTCAATCTTTGGAATGCCATAGGTTCTAGCATACGTTAACTTTTGAGTGGTGA

GTAGTTGATCATAGGGTTTACTAATAATACCAACCACAAGGATATCGACTTTTTTGTCAA

TCCCGTTGACAGGCTTT

SEQ ID 18 Position 2967081 . . . 2968319
AAATACGCAAAAGAACCCGACGAGAGTTAAGTCTCATCGGGTTCTCAGTCGTGGATGAAT

TAGAAGCATTGTTAGCTGCATAACCTTCAACATAGGATCAATAGCTGGTTAGATGGTCAT

CTCTCAGACTGTTTGCACCAGATCCAGGCAAACGTGTTTATATCCTTGGTCATACTCAGG

ATAGATGGGCATTGTGAGTGCAACAGGACTTAGTTGCTTGTATGCTAGGCAATGTTGGCC

TTGATACAGAGGATCACTCTGTTTCTGATCTGGATGATAACCTCGTTTTTCCATTTCAGG

ACGCTGTCCCAATAATTGTTGCCCTGGGAGTTTGTCGAATTAAGTCTTGGTGCCACAAAC

ACACGCTACGGCTTCTTTTCTTGCAAACTGATCTTAGTATTTAGGGCAGTTGCATGATTA

CGGAATTGAACCATTTTATAATGAATCGTCTTTTCTATAAGTCTATAGAAAGTGCAGGTA

ATGGCATTTTCTCCAGATCGGATTGTCTAATCAATTTAATTGATTTTTTGGTGTGTTTG

ATTATATTGCTTTTGCAAAGGTACAATATACCTTTTCTCTGCTGCCTTGCGAGCAGCGAT

GGCATCCTCCATATGAACATATACACGATTTAGGACAAGATGGCCTTGAAAGTACAGCCT

TGCGACCCACTTTTGAGCAGTTTTATCCCAACTAACTCCGATAACGCCAGATTTGTTATT

GGACCGTTTAAGTGTAGAAGCAACTAAATTTGTTCGATTAATTAGTTGAAAATTCTTGGG

ATTGCCCATGTATTTTTAGTCTGGTTATTAGCTTTTATGTTTGATCTGCTTATTTCTGA

TCGCAAACACCCACAACTGCGAGTGAGTCCTTTTTGAAGTCGTTGACTGTCAACGATACA

TTTATTTCCACATTGACATTGACAGAGCCAAAGCGCGTTTCCATTAGAACTGCTTCCAAA

AAAACTAATGACTGTGAGTCGTCCAAACGTTTGATTGGCCAAATCGATACGCTTTTGCAT

ACTAATCTCCCGTTTGATAAGAAGGTACTTAAAGAGTTGTTTTCAATTGATCTAGTCGC

CATTGGCACCATGAAATAAAGGCTAATTCGTCAATCTTTGGAATGCCATAGGTTCTAGCA

TACGTTAACTTTTGAGTGGTAAGTAGTTGATCATAGGGTTTGCTAATAATACCAACCACA

AGGATATCGACATTTTTGTCAATCCCGTTGACAGGTTTT
```

REFERENCES

Bjerkan, L., Schreurs, O., Engen, S. A., Jahnsen, F. L., Baekkevold, E. S., Blix, I. J., and Schenck, K. (2015). The short form of TSLP is constitutively translated in human keratinocytes and has characteristics of an antimicrobial peptide. Mucosal Immunol 8, 49-56.

Capone, K. A., Dowd, S. E., Stamatas, G. N., and Nikolovski, J. (2011). Diversity of the human skin microbiome early in life. J Invest Dermatol 131, 2026-2032.

Cho, I., and Blaser, M. J. (2012). The human microbiome: at the interface of health and disease. Nat Rev Genet 13, 260-270.

Dominguez-Bello, M. G., Costello, E. K., Contreras, M., Magris, M., Hidalgo, G., Fierer, N., and Knight, R. (2010). Delivery mode shapes the acquisition and structure of the initial microbiota across multiple body habitats in newborns. Proc Natl Acad Sci USA 107, 11971-11975.

Ehlers, S., Kaufmann, S. H., and Participants of the 99 Dahlem, C. (2010). Infection, inflammation, and chronic diseases: consequences of a modern lifestyle. Trends Immunol 31, 184-190.

Fornasa, G., Tsilingiri, K., Caprioli, F., Botti, F., Mapelli, M., Meller, S., Kislat, A., Homey, B., Di Sabatino, A., Sonzogni, A., et al. (2015). Dichotomy of short and long thymic stromal lymphopoietin iso forms in inflammatory disorders of the bowel and skin. The Journal of allergy and clinical immunology 136, 413-422.

Hanabuchi, S., Ito, T., Park, W. R., Watanabe, N., Shaw, J. L., Roman, E., Arima, K., Wang, Y. H., Voo, K. S., Cao, W., and Liu, Y. J. (2010). Thymic stromal lymphopoietin-activated plasmacytoid dendritic cells induce the generation of FOXP3+ regulatory T cells in human thymus. J Immunol 184, 2999-3007.

Jang, Y., Jeong, S. H., Park, Y. H., Bae, H. C., Lee, H., Ryu, W. I., Park, G. H., and Son, S. W. (2013). UVB induces HIF-1alpha-dependent TSLP expression via the JNK and ERK pathways. J Invest Dermatol 133, 2601-2608.

Jin, S. H., Choi, D., Chun, Y. J., and Noh, M. (2014). Keratinocyte-derived IL-24 plays a role in the positive feedback regulation of epidermal inflammation in response to environmental and endogenous toxic stressors. Toxicol Appl Pharmacol 280, 199-206.

Kong, H. H., Oh, J., Deming, C., Conlan, S., Orrice, E. A., Beatson, M. A., Nomicos, E., Polley, E. C., Komarow, H. D., Program, N. C. S., et al. (2012). Temporal shifts in the skin microbiome associated with disease flares and treatment in children with atopic dermatitis. Genome Res 22, 850-859.

Naik, S., Bouladoux, N., Wilhelm, C., Molloy, M. J., Salcedo, R., Kastenmuller, W., Deming, C., Quinones, M., Koo, L., Conlan, S., et al. (2012). Compartmentalized control of skin immunity by resident commensals. Science 337, 1115-1119.

Noh, M., Yeo, H., Ko, J., Kim, H. K., and Lee, C. H. (2010). MAP17 is associated with the T-helper cell cytokine-induced down-regulation of filaggrin transcription in human keratinocytes. Exp Dermatol 19, 355-362.

Schaper, K., Rossbach, K., Kother, B., Stark, H., Kietzmann, M., Werfel, T., and Gutzmer, R. (2016). Stimulation of the histamine 4 receptor upregulates thymic stromal lymphopoietin (TSLP) in human and murine keratinocytes. Pharmacol Res 113, 209-215.

Siracusa, M. C., Saenz, S. A., Hill, D. A., Kim, B. S., Headley, M. B., Doering, T. A., Wherry, E. J., Jessup, H. K., Siegel, L. A., Kambayashi, T., et al. (2011). TSLP promotes interleukin-3-independent basophil haematopoiesis and type 2 inflammation. Nature 477, 229-233.

Volpe, E., Pattarini, L., Martinez-Cingolani, C., Meller, S., Donnadieu, M. H., Bogiatzi, S. I., Fernandez, M. I., Touzot, M., Bichet, J. C., Reyal, F., et al. (2014). Thymic stromal lymphopoietin links keratinocytes and dendritic cell-derived IL-23 in patients with psoriasis. J Allergy Clin Immunol 134, 373-381.

Watanabe, N., Wang, Y. H., Lee, H. K., Ito, T., Cao, W., and Liu, Y. J. (2005). Hassall's corpuscles instruct dendritic cells to induce CD4+CD25+ regulatory T cells in human thymus. Nature 436, 1181-1185.

Wilson, S. R., The, L., Batia, L. M., Beattie, K., Katibah, G. E., McClain, S. P., Pellegrino, M., Estandian, D. M., and Bautista, D. M. (2013). The epithelial cell-derived atopic dermatitis cytokine TSLP activates neurons to induce itch. Cell 155, 285-295.

Yockey, L. J., Demehri, S., Turkoz, M., Turkoz, A., Ahern, P. P., Jassim, O., Manivasagam, S., Kearney, J. F., Gordon, J. I., and Kopan, R. (2013). The absence of a microbiota enhances TSLP expression in mice with defective skin barrier but does not affect the severity of their allergic inflammation. J Invest Dermatol 133, 2714-2721.

Ziegler, S. F. (2012). Thymic stromal lymphopoietin and allergic disease. The Journal of allergy and clinical immunology 130, 845-852.

The invention claimed is:

1. A method of treating or preventing an inflammatory dermatological disease, an allergic skin disease, or dysbiosis of epidermis or dysbiosis of cutaneous microbiota in a human in need thereof, the method comprising topically administering a therapeutically effective amount of a composition comprising a postbiotic second fermented supernatant of a *Lactobacillus* species selected from the group consisting of *Lactobacillus casei* and *Lactobacillus paracasei*, wherein the postbiotic second fermented supernatant is produced by a method comprising:
   (i) fermenting a first culture of *Lactobacillus casei* or *Lactobacillus paracasei* to form a bacterial suspension comprising a first biomass of the *Lactobacillus casei* or the *Lactobacillus paracasei* and a first fermented supernatant;
   (ii) separating the *Lactobacillus casei* or the *Lactobacillus paracasei* first biomass from the first fermented supernatant;
   (iii) fermenting the *Lactobacillus casei* or the *Lactobacillus paracasei* biomass from step (in a minimum solution consisting of water, saline, phosphate buffer and a lactate salt to form a further fermented biomass comprising the *Lactobacillus casei* or the *Lactobacillus paracasei* and a second fermented supernatant; and
   (iv) separating the *Lactobacillus casei* or the *Lactobacillus paracasei* from the further fermented biomass from step (iii) to obtain the postbiotic second fermented supernatant;

wherein the *Lactobacillus casei* or the *Lactobacillus paracasei* comprises in its DNA genome a DNA sequence 100% identical to one of the sequences selected from the group consisting of SEQ ID NO: 2 and SEQ ID NO: 5.

2. The method according to claim 1, wherein the minimum solution is a solution which does not contain carbon and/or nitrogen sources or micromolar concentration of minerals.

3. The method according to claim 1, wherein the second fermented supernatant is prepared at a temperature of 0° C.-10° C.

4. The method according to claim 1 wherein the second fermented supernatant is a dry powder.

5. The method according to claim 1, wherein the first and the second fermented supernatants, when analyzed by MALDI TOF mass spectrometry, have the following peptide signal profile:

| SN1 m/z | SN2 m/z |
|---|---|
| NO signal | 357.07 |
|  | 423.06 |
|  | 373.05 |
|  | 406.07 |
|  | 439.04 |
|  | 489.05 |
|  | 505.03 |
|  | 538.05 |
|  | 557.1. |

6. The method according to claim 1, wherein the second fermented supernatant, when analyzed by MALDI TOF/TOF mass spectrometry, has the following peptide signal profile:

| SN2 | |
|---|---|
| Fractions | m/z |
| 3 | 1193.2 |
|  | 855.2 |
|  | 756.38 |
| 4 | 524.06 |
|  | 542.08 |
|  | 664.12 |
|  | 756.38 |
|  | 644.37 |
| 5 | 756.43 |
| 6 | 610.34 |
| 12 | 1006.8 |
| 13 | 1393.2 |
|  | 1153.77 |
|  | 1033.68 |
|  | 707.28 |
|  | 855.54 |
| 15 | 1153.76 |
|  | 1393.8 |
|  | 1033.65 |
|  | 855.34 |
| 16 | 1153.76 |
|  | 1393.8 |
|  | 1033.65 |
|  | 855.34. |

7. The method according to claim 1, wherein
(a) the fermentations in steps (i) and (iii) are conducted at a temperature ranging from 4 to 40° C. for 12 to 36 hours;
(b) the first biomass is separated from the first supernatant in step (ii) by centrifugation; and
(c) the *Lactobacillus casei* or *Lactobacillus paracasei* is separated from the second fermented supernatant in step (iv) by centrifugation.

8. The method according to claim 1, wherein the *Lactobacillus* species is *Lactobacillus paracasei*.

9. The method according to claim 1, wherein the *Lactobacillus paracasei* is the strain deposited according to Budapest Treaty with the accession no. CNCM I-5220.

10. The method according to claim 1, wherein the postbiotic second fermented supernatant is present at 0.1-1% w/w in the composition.

11. The method according to claim 1, wherein the lactate salt is sodium lactate, calcium lactate, or potassium lactate.

12. The method according to claim 1, wherein the postbiotic second fermented supernatant comprises 2-6 mg/L of 7 hexadecenoic acid, 2-6 mg/L of tridecanoic acid, 10-15 mg/L vaccenic acid, and/or 3-5 mg/L oleic acid.

13. The method according to claim 1, wherein the composition administered topically is selected from the group consisting of a cream, an emulsion, a dispersion, a gel, an ointment, a lotion, and a serum.

14. The method according to claim 1, wherein the human has psoriasis, contact or atopic dermatitis, eczema, rosacea, itching, acne, dry skin, surgical scars, sunburn, greasy or itchy dandruff, cold sores, trichodynia, or seborrheic dermatitis.

15. The method according to claim 1, wherein:
the first fermented supernatant comprises 3-9 mg/L of oleic acid, 1-3 mg/L of decanoic acid, 1-4 mg/L of benzopropanoic acid, and/or 10-15 mg/L of citric acid; and
the second fermented supernatant comprises 2-6 mg/L of 7 hexadecenoic acid, 2-6 mg/L of tridecanoic acid, 10-15 mg/L vaccenic acid, and/or 3-5 mg/L oleic acid.

16. A method of treating or preventing an inflammatory dermatological disease, an allergic skin disease, or dysbiosis of epidermis or cutaneous microbiota in a human in need thereof, the method comprising topically administering a therapeutically effective amount of a composition comprising a postbiotic second fermented supernatant of *Lactobacillus paracasei*,
wherein the postbiotic second fermented supernatant is produced by a method comprising:
(i) fermenting a first culture of *Lactobacillus paracasei* to form a first bacterial suspension comprising a biomass of the *Lactobacillus paracasei* and a first fermented supernatant;
(ii) separating the *Lactobacillus paracasei* biomass from the first fermented supernatant;
(iii) fermenting the *Lactobacillus paracasei* biomass from step (ii) in a minimum solution consisting of water, saline, phosphate buffer and sodium lactate to form a further fermented biomass comprising the *Lactobacillus paracasei* and a second fermented supernatant; and
(iv) separating the *Lactobacillus paracasei* from the further fermented biomass from step (iii) to obtain the postbiotic second fermented supernatant;
wherein the *Lactobacillus paracasei* comprises in its DNA genome a DNA sequence 100% identical to one of the sequences selected from the group consisting of SEQ ID NOs: 1-18.

* * * * *

UNITED STATES PATENT AND TRADEMARK OFFICE
CERTIFICATE OF CORRECTION

PATENT NO. : 12,324,820 B2
APPLICATION NO. : 16/965469
DATED : June 10, 2025
INVENTOR(S) : Maria Rescigno, Giuseppe Penna and Francesca Algieri Page 1 of 1

It is certified that error appears in the above-identified patent and that said Letters Patent is hereby corrected as shown below:

In the Claims

In Claim 1:
Column 89, Line 67 "step(in" should read --step (ii) in--.

Signed and Sealed this
Twenty-second Day of July, 2025

Coke Morgan Stewart
*Acting Director of the United States Patent and Trademark Office*

SEQUENCE LISTING

```
<160> NUMBER OF SEQ ID NOS: 41

<210> SEQ ID NO 1
<211> LENGTH: 165
<212> TYPE: DNA
<213> ORGANISM: Lactobacillus casei and Lactobacillus paracasei

<400> SEQUENCE: 1
atgaatcaaa aagctttgaa tcaatttcct gaacttacct acacagaaca agtgtcggtt    60
gttggcggcg atttgtcagt cgaagtcatc atgaaaggta tcttcaccgg tatctttgat   120
gctgggtacc aagtgggtca gtcaatcgca aaatgggtta agtaa                   165

<210> SEQ ID NO 2
<211> LENGTH: 108
<212> TYPE: DNA
<213> ORGANISM: Lactobacillus casei and Lactobacillus paracasei

<400> SEQUENCE: 2
atgaaaggta agcggcagca cttactttta tattttgttc tgggtatgat gacaggactg    60
gtgacggcag cgattttttca tatcatttat gcctggcttt tcattga                108
```

```
<210> SEQ ID NO 3
<211> LENGTH: 462
<212> TYPE: DNA
<213> ORGANISM: Lactobacillus casei and Lactobacillus paracasei

<400> SEQUENCE: 3
atgcccaaaa gggtcgatca acatatacgt tcacgcctta aaggctttac tttaattgaa      60
gtggtggtca gcctgatttt acttgcggcg tcatgctgt tatggcgacc ggttttattg     120
catgtcacgc ggttcacgct tcaagaccat gtgctaatca cgtcattgca agcagagcat    180
gacttgcaaa tgtttgtacg agataaaaag ttgcggtctg tggccttaat gtcggtaagg    240
gtgagaagtc ccgagaaagc ttacacgatc aatttttatc agaccaaaca ttttcgcggt    300
atggttcgtg tgatgggatc tgaaaatggg catatgccat tatttacgca tctaaccggt    360 gtcaattttta gcaaggtagc tcaaggcttt cgctatcgtc tgtatttgac gacttcgcag   420
aagattgacg gtggggtgca atcgatgaa gatacgcggt ag                        462

<210> SEQ ID NO 4
<211> LENGTH: 507
<212> TYPE: DNA
<213> ORGANISM: Lactobacillus casei and Lactobacillus paracasei

<400> SEQUENCE: 4
atggccgctg atttcaccca attacaacaa gccattcgct tgctcaatgc ccatactcga     60
gctgctgatg agcaagcgtg gcaagtgctt tttgatcgtt ggctggcaac tttatcctct   120
gaaactcgcc ggcaaatgca aacagttcgg tttaatcatg cccaattgac gttactcaca   180
acgctggatc aaagcagtcg caaacaactg cgcaatcagg atttaaccgc tgctgttccg   240
ttctcacaag gcctagtctc acgctatgtt gctcgccttg ttcaattaaa cttgctgaca   300
aaattatcct tgcccgacaa tcgcaaggcc tacattgttg cactaactcc gcttggtcaa   360
caagtcgctg ccttacatca gcaaatgcat catcacacaa atgctcaact cgcctctgta   420
cttcataccc ttgatccaca agatgttcaa actaccattc aggtactcac aaaactgacg   480
gctcagcctt tacatcccaa gtcttag                                        507

<210> SEQ ID NO 5
<211> LENGTH: 261
<212> TYPE: DNA
<213> ORGANISM: Lactobacillus casei and Lactobacillus paracasei

<400> SEQUENCE: 5
atgggcggtg tcatttgtta cgcggtgccg gtcttttgga aaagaatact tcgcagacac     60
ctgattcacg agattaagac cctgaatcaa ggattgcagt tatcaagcaa agccatgagc   120
caattaattg atccggaaaa tcctatatg gtatttgctg atgaaaatgg tgaactggat    180
ttttcatttt tgtggctagg caacttgcgt caattgaggc gtgaactgcg tctaattaaa   240
gaacagaaag ctagggtttg a                                              261

<210> SEQ ID NO 6
<211> LENGTH: 1077
<212> TYPE: DNA
<213> ORGANISM: Lactobacillus paracasei

<400> SEQUENCE: 6
atgagtaaat ataaagttat tatttgggga ttaggaaacg ttggtcgttc cgcagtgaga     60
atgatcgcgg aaagacaaaa tattttttgaa ttggttgcag ccgttgacgt tgatccaaag   120
```

-continued

```
aagttaggta aggatgccgg agaagtcttt gattttgaca aagtcggcgt caaagtttca      180
gatgatattg atgcagcctt gaaacttcca gctgacattg tgctcgactt ttgcccaacg      240
gaaatggaca acaaggaac attcatgcct tctgctattc gactcgccaa atcgctcgat      300
gccggtaaaa acgttattac cacgattccg gtatatcatg ttcaagacag tcagccagaa      360
gtatatgaat atctaaatga acatgctaaa gcacataatg ttgcttttgt accatttgga      420
cttttgccag gcgattatgc ctcatatatc ccactagttt tggccggggc catgggccac      480
gtggataaaa ttgttgttca atccggtgaa gatgactggc acaacacatc aggctgggtc      540
gatgtcttct catatggcgg cgatatcaat aaatatccaa aaccagactc agacgaagat      600
ctcttggcta agttcattta tgcttattat tcatccggcg tatacgagat ggccgatagg      660
atcggtctga aatatgatac cttcaaacca gagcatgaag tcttcactgc acccaaagat      720
ttggaaacga tcaagggtac agtcaaaaag ggcagcattt atgcccacag atttaccatg      780
gcactttaca acggcaacga acaagtagcc gccttaagat atgttcataa agttgataat      840
aaagagacac cagaattacc gatcaataat acgattcata ttgaaggctt gccgtcagtc      900
gatgcgcaga tcgatggatt gatcccagaa agagaaggct acgtttcatc agccgctcca      960
gcagtcaact tgatccctag cattctcgag accgacaaga caggttatgt tgaagtctgc     1020
gaccttccag tagtgattgc caggccattg gatattggcg caaaaaaatt agtctag       1077

<210> SEQ ID NO 7
<211> LENGTH: 561
<212> TYPE: DNA
<213> ORGANISM: Lactobacillus paracasei

<400> SEQUENCE: 7
atggcaacct attcgcagat agaactagac ataatcaaat catttaaagg gctgatgaaa       60
gaccatgaat tcactgagat ctcaattaaa atgatcgctg aaaaagccga tatcactcga      120
cgcggctttt acaatcactt cttagataaa tatgatcttg tcagtaccat ctttgagcat      180 gatcttttc caacagtcat cagtttgacg aatatcaatg actgggatca agggtcgctg      240
tttatcgtga attatctcca agacaatcgc gactactata aaaaattgtt gtcgcttgaa      300
ggacaaaact gtttacagac agactttat aaattgactg agatgcagat tgggatcttg      360
atcccagaaa tattggtcgg taggaaaatt tctgacgaag atcaggcatt tttaagcgat      420 tattatttc acgcttatat gggactgact accgaatggg tcaaaggtaa atatggtttt      480
tcaactcagg agttcgttaa acggtggaaa gccttactca ataattcaat gcataattat      540
ctggacaact acgctcgatg a                                              561

<210> SEQ ID NO 8
<211> LENGTH: 1077
<212> TYPE: DNA
<213> ORGANISM: Lactobacillus paracasei

<400> SEQUENCE: 8
atgagtaaat ataaagttat tatttgggga ttaggaaacg ttggtcgttc cgcagtgaga       60
atgatcgcgg aaagacaaaa tattttttga ttggttgcag ccgttgacgt tgatccaaag      120
aagttaggta aggatgccgg agaagtcttt gattttgaca aagtcggcgt caaagtttca      180
gatgatattg atgcagcctt gaaacttcca gctgacattg tgctcgactt ttgcccaacg      240
gaaatggaca acaaggaac attcatgcct tctgctattc gactcgccaa atcgctcgat      300
gccggtaaaa acgttattac cacgattccg gtatatcatg ttcaagacag tcagccagaa      360
```

```
gtatatgaat atctaaatga acatgctaaa gcacataatg ttgcttttgt accatttgga    420
cttttgccag gcgattatgc ctcatatatc ccactagttt tggccggggc catgggccac    480
gtggataaaa ttgttgttca atccggtgaa gatgactggc acaacacatc aggctgggtc    540
gatgtcttct catatggcgg cgatatcaat aaatatccaa aaccagactc agacgaagat    600
ctcttggcta agttcattta tgcttattat tcatccggcg tatacgagat ggccgatagg    660
atcggtctga aatatgatac cttcaaacca gagcatgaag tcttcactgc acccaaagat    720
ttggaaacga tcaagggtac agtcaaaaag gcagcatttt atgcccacag atttaccatg    780
gcactttaca acggcaacga acaagtagcc gccttaagat atgttcataa agttgataat    840
aaagagacac cagaattacc gatcaataat acgattcata ttgaaggctt gccgtcagtc    900
gatgcgcaga tcgatggatt gatcccagaa agagaaggc acgtttcatc agccgctcca    960
gcagtcaact tgatccctag cattctcgag accgacaaga caggttatgt tgaagtctgc   1020
gaccttccag tagtgattgc caggccattg gatattggcg caaaaaaatt agtctag      1077

<210> SEQ ID NO 9
<211> LENGTH: 429
<212> TYPE: DNA
<213> ORGANISM: Lactobacillus paracasei

<400> SEQUENCE: 9
aaaaacggct tagaacgctc atatttgcgt tctaagccgt ttttatcagc ataggttctt     60
gacaccaata aacatcttta gtaattgatc aaatttaggc aatgtgcttt tgtcggtgaa    120
tggcgatagc cctaccgaag cttcagctga ggttcttctg agccacgcaa gcgaagcgcg    180
ctagggcaag ccaacggcgc gcaggcgaag ccggagttaa atgtggcgca gccacacctt    240
tttagggagc aacgcgacca gaattttgta tggggtttgg gaagaggttc tccccaaggt    300
cttttgtggt tattaacaag caaaacacaa acacaagcct cgcgcgcgtt atatatactt    360
ctaaatactt ttaaatactt taagtactta gggagacgag aatggctcaa ccacgcgttt    420
aaatcgact                                                             429

<210> SEQ ID NO 10
<211> LENGTH: 241
<212> TYPE: DNA
<213> ORGANISM: Lactobacillus paracasei

<400> SEQUENCE: 10
acgacctctc gaccacccac tgcctcacca atccccaggt gaaccgggcc aagggcacta     60
ccgagcaacc cgacccctat atcccggtgg gcgtggtgaa gcagaccgat gggggcatcg    120
tggtgcgggg cgcgcggatg ctctccacgc tgcccacggc ggatgagctt ttagtcttcc    180
ccagcacttt gctcaaagaa gggccgggag ccgacaagta cgccgtggcc ttcgccatcc    240
c                                                                     241

<210> SEQ ID NO 11
<211> LENGTH: 7384
<212> TYPE: DNA
<213> ORGANISM: Lactobacillus paracasei

<400> SEQUENCE: 11
attgatcgcc tccgggtcac ttatatgtaa ctaataatac tcccttctct ctttagttac     60
aatagggtac agcctatcga atcacttacg cttccacttt gagataactt ttcgttatta    120
```

```
tttatcaacg gcattaacga tatcattaac tgtttgcaat gcatcgctca gtacactaat    180
tggtgcttgt tcaatatact gcatgtgtcg ttgtacaaaa tcaaaggtgt gaaattgtaa    240
cggattcacg taccottcta ttttttcagt ctgaatcggt accatcaagc ctgtttcagc    300
taagcgatta tgtttggcat gcgtgatcgg acaaaccaac gctaatccag tcattttggc    360
atattgttga ttgctaataa cgagcgctgg tcgtctttt  tgaatttcat gaccccgact    420
tggcatgaaa tcaatactca caacatcacc tttgcgtggt tgataatgcc tagtcccact    480
cacttggtaa tacctcgttt tctaacgtaa tatcttgttg gtgtacttgt tgcttgtacc    540
aatcaccttc aaatggattg cggtgcttcg gcagataaag aatgccacca tcatcacgtt    600
gctcaactgt aaattcagtt ccatcggcga ttttaatact ctttggaatg gttaatgtaa    660
tggaattgcc aacccttctt gctttaactg tcattgaaat catcctttcg tatacaccga    720
gtatacacca gcgcgaatga atctgcaact cttgtgccct cttgtgtaca aacaccactg    780
tcaatttact tttgcctatt gtgctttatc tcttctcgtt ctgtcattag tatgccacca    840
acacggccga cttcatccgg ctcacctttg atgacgcctt gaataccatc gatttgcttc    900
caagtcttta cttccaagtt ttcaaagac tttgatatcg tttttcgatg ccggcaaaca    960
cttcttcatt ctgatgcctt tcaaagaatt cctctagatc attcatcaga gattctcctc   1020
acttaaacct agttggcgtc aaattccatc tcagcaatcg aatcttctag gctgtccatt   1080
acttcgtatg tttcaatgaa gttaacccag ctgtcatatg gatgtagttt gctttctta   1140 atgctagttc taagcttttc gtacacgttg tcaataaact gctcaaccat cctattaacc   1200
gcactattaa taaccgcttc gttccactgc ttagatgctg cacgctttcg attttgacta   1260
tgctgatggg acagcgcccg gcttctgaac aacgctactg ccctgctgtt agcattcaga   1320
taggtttcaa attcttcacg atccattacg tttcctcctc aaaataagcc tcatttcata   1380
gcacagcttc agcaaaaggc atgtcatcct acatgccttt tttctgttgc tcttcaatat   1440
cagtataaaa cgtcctgccg ctttaggcaa acgtatgttc gctattaaga acatacgttt   1500
gtataataac tataaaagat ttaaaggagg tcaatcgtat ggaaaacaat gtcccgcgtg   1560
aaaaatggct ttaccctgac cgctgcatga agaaatggct gggctggatt ctaagcgacc   1620
attccgccta tatggaagaa gcggctatct cagaacaacc ggtgctccca aagcctgaac   1680
agacacaaga aaccattaat ggcgtactcg aagatgcttg gcaaaactca aaaattgtcg   1740
cagttcaaat cggtacgcca tacgatgatc ttctgttacc ggatattgaa ggcgccgtga   1800
ttggtcattg ggacgctcag gtttatctac agcttaaaac tggtgagatg caatccatta   1860
atgcagcgga cattcgcaat gtgcaactgc tcaatccaga tcggtggtgg gcgttagtat   1920
gacgacacca ttagatgatc caacaaggtt accggtacac gacattatgt gcattgactg   1980
taagtccttt tacgcctcag ttgaagctat cagacgcggg attcatccgt tagccgccga   2040
cattgctgtt ctcagcaaag gtaattctcc tggcggtttg gtgctggctg ctagtcccaa   2100
ctgcaaaaag cgttaccacg taggactgag tacacgccgt tttcagctaa gggacgatat   2160
gtaggtagaa cttgctgaac cgcggatggc taattacatt cgcaagaatt acggtatcaa   2220
tcgtatttac cgtcagttta ctgacgatgc tcactggtct ccctattccg ttgacgagtc   2280
ctttattgac gttaccacc  cccacaatct cttcggttct aatgaagaaa ttgctaccca   2340
aatacagaag aaggtgtttg atcagtttgg cattgtcaca acagttggca ttgggcaaaa   2400 tccctattg  gcaaaattag ccctagataa cgaggctaag aagtcaacgc cttggcaagc   2460
cacttggact tacgatcgtg tgccagaaac aatatggaaa cttgatgact ggttgatttt   2520
```

```
ttggtcgatt ggtaatcgaa ctgccaagaa gcttaacgcg attggccttc ataatcttta   2580
cgacttggct catgcagacc gcgccattct gcaccaaaga ttcggtgttc tcggtgatgc   2640
catgtacttt cacgcatggg gtattgatta ctcagactta acccgccgct acttaccacg   2700
ggccgaaaat aaaggctacg gcaatagtca ggtactcatg cgtgattaca ctcaggcaag   2760
ggagattgaa gtcatgctta gcgagattgc tgatcaagtg gctggccgaa ttcgccatca   2820
ccaagtccaa ggtgaggtca ttagcgttgg cattggttat gctgatgcag aagaagctgg   2880
cacctccggt ttcggtgcgc aaatgaagat tgatcccaca aatcgcacag acgatttaat   2940
tcgcgctact cgatttctct tccatagtaa gtggaacgga cacgctgtta gaaatgtctc   3000
agttcgcgtt aatcgcatca gccaagcaag tacaatgcaa cttagtctat tgaatcagc   3060
agagaaggag gaagcaaacg cggctcctat gctgtaatta cggataaaag aatcaccatc   3120
attaggtttt tcgtctaaca attttaggaa acttcacttt ctaggtcgta actttatttt   3180
tgcaatctag ggttttttaa atatatacat tttagctcgt tgtgtttaa tattataatc    3240
acaactatac caatgataaa tgtctaacat aaatatacaa acatgttgac agaagctctt   3300
gaatacgttt acaattattt cgttcaggcg agctttgttt ttgaaaaagt attaatacaa   3360
gataactagg ttagtggctg ttgaattagg cccccgattt cgggaccacg acagtcactt   3420
gatactcgat ttttatcgtt tgctggcttg atcgtacatt gaacgaaatt ggtacagaaa   3480
aaagagctaa gagccgctcc aaattagcca aaacgattgc ggcgtcaatg cttacggcga   3540
tcgtttctgc agttttagct gttaccagat caagtcctag tttcccttg atgaaggcaa    3600
actcacgctc gatctcacct cgtcgatttt cggcttgtcg gtctgcctta cgtttggccg   3660
gatcgacctg cttcggccga cggcccaatc taggaccgct aagtttgatc ccaagatctg   3720
cgcacagccc gatattcgcc cgagtccgat aaagcgtatc agccaagatc tcatccgggt   3780
atgtaccata cgtgtcaaaa taatggtcga tcgttgctgg taagtcagca ctttcgttaa   3840
acgcattgaa cgcaaaccgt tcaacggcca cgacgccatg actgatcgat acgtcgatct   3900
tgggcccgaa ttcgaccgga tcctttgctt tgccgcgaat gatcggtcgg atcgctggtt   3960
gatcaaggct tacgatccga tccgcgactc ggtgagtgtg ctgtcgatac atttcagttt   4020
gttgctcata caattttcga atgatcgtta atcgttgtgt ctgccgttga ttcaattgcc   4080
cgccttgtgc ttgcagttct ttgacgtaac gcaagtcacg tcggatgtac tgtaattgag   4140
ccttgatctg cttatgggtc gttttcaccc aacggcgggg tttacgtgaa aaggcggtcc   4200
acgtttggtg ggccttgcgc ttataggtac gcggcggttt gaccgctaat tgcttggcca   4260
tggctgcgat gaatcgctct aaattgagcc gcgcctgatt gagtagctgc gtatcctgcg   4320
gatacttgat ctttactggg accgcagtcg catcagtgat caagatcttc tgatggccaa   4380
gtttagcttg gaggcgatcg cggacaaaat cgctaatgat gttcgtgatc aactcggaaa   4440
gcggcgcgat ccggcgcctg aaataggaca gcaccgaaaa tgaaaacggt gcttgcggct   4500
gatactctgg caggccaata aaatactgat aagccggtgt atcgcggatc gctgcgacta   4560
actcacggtc cgatagctga gtgcgctgct tgatcagttg ggcgccataa agcagccgaa   4620
agggtttacc tgcccatcct aagttagacg ggaaagccaa ttggtacgcc tcttctagtt   4680
gcggccacgg aacttggtcg gccagttgga cccactcgtt atctggactt aatggggtgc   4740
ttaagccgct accaaacgat ttgatcgata attgaacggc ttttcgacga taaaccatga   4800
tccatgcctc cgatagggtc gtgtcaaatg caaacgaaat gagcacgatc cgtaaattca   4860
```

```
tatgcattca ttatacgacg ataacgggtt caactcgcat caaatgtggt tatatcaaat    4920
tattcaacag ccactaggtt aagatcttca tttaagtgat attcatttgc aagcaattga    4980
aaattactca tcacgaagag gatttcattg gccatattgg atagcacgca aatcacttgc    5040
tttaagaaaa tcagttcctt taatgagtct cttaaaggac ggggctctca cttgtactca    5100
caatcaatgt taactggaga tcaacaatat ggtcatagat tcccataata acattgactt    5160
gactatctaa aagaggcttc taactttgat attggtgggg ttattggttg cttggctgta    5220
agcagataat cttaacttgg gttattttca ttgtgttgta aagacatttg ttataaaggc    5280
cgaagttatc gctttgactt gtaataaatt attttttgatt gagatatcag aaaataaacg    5340
ggggataata atgaaaaaga ttattaggat tgttctttgt gttgttagtt gcgttagtat    5400
catggtcgga tcgcttgggt tctattcaac tccaaagatc gttaaagccg acagtacatc    5460
tgttacggat gtcgacatta atacctatat ttctagcatg acacttgatc aaaaaattgg    5520
acaaatgttt gtagcacgaa cctcacaaga tactgataaa gctcgtgctg atatagcaaa    5580
atataatctt ggcgggctga ttgtttatgg tgttgatttc actagtgtta aagggacaac    5640
agctacagaa gctcagaata acttcaagat gaagatgcaa ggctttcaaa actcggcaag    5700
tctgccacta ttgattggtg ttgatcaaga aggaggggga gtctcacgct tatcacaaaa    5760
tcctctaatt gccaacggca gaagttttcc ttcaccacaa atggcttatg ctaatggtgg    5820
aatgaccaat gtaacaaaag aagctagtga agtcggaact attctaaaaa atctgggcat    5880
taactggaac tatgcaccag ttgccgacag tacgcctgac acctctagtt ttatttatgg    5940
tagaaccttt ggtcaagatt acttggctac tgcaaactat attacgaatg tgatccctgc    6000
gtggcaaaat gctggcattg ccgcaactct caagcatttc cctggttatg gatccgcgat    6060
tgatacgcat acggattttg cagtcgttac aaagtctaag gaggattttg aaaaagagga    6120
cttgcttccc tttaagtccg gtattacagc aggggcagat tctgtaatga ttgcacatat    6180
agtaatgcaa gctgttgacc cagtgtatcc agcatcatta tcacggaagg tcgttaccga    6240
tttgttgcgt aatgaacttg ggtataatgg cttaataatt accgatgcat tggaaatggg    6300
ggccatcaag caatttgctc aagaacatga tcaagttcct gttgatgttc ttgctgttga    6360
agcagggaat gattgcatca tgaataacga ttatgaaacc gctattccac agattcatgc    6420
agcagtaact aatggaacta ttaaggaatc agaaatcaat gaacacgttt ccgtattct    6480 tgatctcaaa cgcaaattag ggttgttaac taaaggacaa cttcagcaaa aaaaagttca    6540
ggttgacaat gttccctaca gcagtgacaa caaaaaggca actgtgagtg gaacagttgt    6600
tgatagtgat tggcaagttg gagaaccatt atcggttaaa gactcgactg ggaaggtcat    6660
tattaccgca gacgttggtg ccggtggtaa gtttactttc gatgttccta ctaagtccca    6720
agaacaagta ttaactctga ctactaattt acccaacatc gctgattctc aaataactat    6780
taaggctgtg agttcatcga atactaacaa agctttgcta gaaaacttga tcaacgctgc    6840
tgaacagttg gatagtaatc aatatactgt caagtcgtgg gaagaattac aaactaaact    6900
aactgaatca aaatcgattc tgaacaatga tagtgctaca caagatcaag tagacgcttc    6960
cgttaatgct ctacaaattg cccttaagca attagttcct gtatcaaata gcggaaataa    7020
tggtcaaagc tctaatgata gcagtaacca aagttcatct agcagtagtg gcaaagaatc    7080
atccagcaat agcaatgcca atattactag taaggatcag tcagctaagg attcaaatac    7140
gaggcctaaa gaccatagtc ttttgccaag tacaggtgaa cgggtgatga cgggaatttc    7200
tgttctaggg gtaattttaa tagcttgtgt gactatatta tatattcgga aaaaaggacg    7260
```

| | |
|---|---|
| cagcttttaa ttagtctctg cgtcaactgg cgttaaaaac tagattgaag taataaagtt | 7320 |
| accacctgga aagaggcatg ctcattgctt gcaagggtgt cgacgtgtaa tagaaaagtt | 7380 |
| gggg | 7384 |

<210> SEQ ID NO 12
<211> LENGTH: 1410
<212> TYPE: DNA
<213> ORGANISM: Lactobacillus paracasei

<400> SEQUENCE: 12

| | |
|---|---|
| tggcgtgggc aacgtgcacg ttttctagtc gctaaactgt gaacaatgct cgtgctaaat | 60 |
| gcaaaactga gcaaggagat gaactataag cgggggaccc tttgctattg aggaggaagg | 120 |
| cgaagtagag aaaagagcggt gatttgaact cgaaacagcg gcgccgcagg ctagcagcac | 180 |
| tgttagatta atcgccagca gcagatacta gacagcttct taaaggcttg ataatagcgt | 240 |
| tgcgccattt caatggaact agtggtcaaa atcgcattgt agttgccatg acccaaactc | 300 |
| gttttacgcg ggccttttg taaaatatat tgaacaactt ggttaatatg ttcatcggtc | 360 |
| tcaaagtcag ccggagttaa atacgttct tccaagtcct tcactgacat cgcttgaatc | 420 |
| ttggcttgaa ttttcgcttc atcagccgta ctcagcaggc ggccttgctt atcacgacga | 480 |
| gctttaacgc gctgagtttc tttttcaagg gcccgggtta ttaaagcgtc tttaccaatc | 540 |
| gttgtcacgt gttccacatt aaatggtaac actgcttggt cctctaaggc gtctcgcaag | 600 |
| ttataaacat gacagacttt accaaatagc tcctccgtcg taactgctag atcacctttg | 660 |
| agctgtttct tattttcatt aaaaatgggg gtgccagtgt aaccatacca gttactattg | 720 |
| ataaacgctg ctcgaatttc cttttgcatc ttaccaaact gcgaccggtg gacttcttca | 780 |
| acaaagaaga tcacccgttg ctttaaagtc ttactaaagc gggattgctt accggttgcc | 840 |
| agctggactt gcgtttttt gaccgcccga tggagctttt gaatcgaggt gaccaagacc | 900 |
| ttaccgtcat tttgttgcaa tttacgcatt aaatcaccgg tgttttgggc ttcgttaatg | 960 |
| gcaatatcat cattggcagc ataggcacta agttgctgg ttgtctgttc gtctaaatcc | 1020 |
| cgccggtcaa ctaagaagat gaccttatcg acaccaggat cttgcgcagc taatttagcg | 1080 |
| gttttatatg aggtgagtgt tttaccagaa cccgtggtat gccaaacgaa accatcctga | 1140 |
| tggtcatgaa tccggtgcat cacggcttca atcgcataaa tctggtaagg ccgtaagaga | 1200 |
| attaagcttt gccgctcttg gtcgatgact gtatattcac tgaccatttt gtgggccatg | 1260 |
| ggaatattaa ggacttggcg cgtgaacgct aacccgtttt ccacggggtg attatcccgc | 1320 |
| gtccgccaat gaacaaaaa ggcttattg aaatgatccg gttcggcatt cgcaaaatac | 1380 |
| gccgtactat ccggcgtcat aatcacaaac | 1410 |

<210> SEQ ID NO 13
<211> LENGTH: 592
<212> TYPE: DNA
<213> ORGANISM: Lactobacillus paracasei

<400> SEQUENCE: 13

| | |
|---|---|
| cgatctaaaa gctaagttat tttccaagat atcaaacaac ttcttaaccc aagaatcttc | 60 |
| cacacatagg acaataatga atccaaatag attcagcttt ttcctgcaaa ccgggatcag | 120 |
| tataaacgtc cagtaccgga taatcacgca ttaagttcag ctgccaatgg gtatcatcta | 180 |
| aattaaaaag atccgattta gtgtctcccc ttactacatt atggcaatac acacaactgt | 240 |

| | |
|---|---|
| tgttatacat gcttccttgc tttttgattt taaactcctc cattttgcat attataagaa | 300 |
| gattacttct acttgatata tagatgcttt ccttgcgagg gtaagtcaga caaggaagca | 360 |
| tttctaactt gagatactta agcttgtctc aatagatgta gatagcggct ccccaatcgg | 420 |
| atattaacag ctcaactagt caaaccagat atataaatgt gacacaagct ggaatatata | 480 |
| tcattatcta gataattcaa attgagctaa taaaatcaat aaagaaaatt ttaaataaca | 540 |
| ttattttata aacccctta ggattttccc gatttgatat tctacgtatg tt | 592 |

<210> SEQ ID NO 14
<211> LENGTH: 2233
<212> TYPE: DNA
<213> ORGANISM: Lactobacillus paracasei

<400> SEQUENCE: 14

| | |
|---|---|
| gagtatccaa aaatacgacg ggtatttgaa taggatactt attaagcgag aatggtattg | 60 |
| gaaatctgtg gcagccactc agcggaacca tacctttatc ccaacccac gcaaaaaaaa | 120 |
| catcaagtaa tccgtcagat atgatgactt aattgtggga cagttctaat atgaagaaaa | 180 |
| caggttagat aattggggtg aaaagatggc aacctattcg cagatagaac tagacataat | 240 |
| caaatcattt aaagggctga tgaaagacca tgaattcact gagatctcaa ttaaaatgat | 300 |
| cgctgaaaaa gccgatatca ctcgacgcgg cttttacaat cacttcttag ataaatatga | 360 |
| tcttgtcagt accatctttg agcatgatct ttttccaaca gtcatcagtt tgacgaatat | 420 |
| caatgactgg gatcaagggt cgctgtttat cgtgaattat ctccaagaca atcgcgacta | 480 |
| ctataaaaaa ttgttgtcgc ttgaaggaca aaactgttta cagacagact tttataaatt | 540 |
| gactgagatg cagattggga tcttgatccc agaaatattg gtcggtagga aaatttctga | 600 |
| cgaagatcag gcatttttaa gcgattatta ttttcacgct tatatgggac tgactaccga | 660 |
| atgggtcaaa ggtaaatatg gttttcaac tcaggagttc gttaaacggt ggaaagcctt | 720 |
| actcaataat tcaatgcata attatctgga caactacgct cgatgaatta cacagattgg | 780 |
| attaaatgag aaagatgtta catttgtgcc aatatgtgaa ttgataaata tttcacaagg | 840 |
| aactattctt tccctgtaaa cgaaagttga cttgaaagga gttagttctg atgagtaaat | 900 |
| ataaagttat tatttgggga ttaggaaacg ttggtcgttc cgcagtgaga atgatcgcgg | 960 |
| aaagacaaaa tattttgaa ttggttgcag ccgttgacgt tgatccaaag aagttaggta | 1020 |
| aggatgccgg agaagtcttt gattttgaca aagtcggcgt caaagtttca gatgatattg | 1080 |
| atgcagccctt gaaacttcca gctgacattg tgctcgactt ttgcccaacg gaaatggaca | 1140 |
| aacaaggaac attcatgcct tctgctattc gactcgccaa atcgctcgat gccggtaaaa | 1200 |
| acgttattac cacgattccg gtatatcatg ttcaagacag tcagccagaa gtatatgaat | 1260 |
| atctaaatga acatgctaaa gcacataatg ttgcttttgt accatttgga cttttgccag | 1320 |
| gcgattatgc ctcatatatc ccactagttt tggccggggc catgggccac gtggataaaa | 1380 |
| ttgttgttca atccggtgaa gatgactggc acaacacatc aggctgggtc gatgtcttct | 1440 |
| catatggcgg cgatatcaat aaatatccaa accagactc agacgaagat ctcttggcta | 1500 |
| agttcatta tgcttattat tcatccggcg tatacgagat ggccgatagg atcggtctga | 1560 |
| aatatgatac cttcaaacca gagcatgaag tcttcactgc acccaaagat ttggaaacga | 1620 |
| tcaagggtac agtcaaaaag ggcagcattt atgcccacag atttaccatg gcactttaca | 1680 |
| acggcaacga acaagtagcc gccttaagat atgttcaataa agttgataat aaagagacac | 1740 |
| cagaattacc gatcaataat acgattcata ttgaaggctt gccgtcagtc gatgcgcaga | 1800 |

| | |
|---|---:|
| tcgatggatt gatcccagaa agagaaggct acgtttcatc agccgctcca gcagtcaact | 1860 |
| tgatccctag cattctcgag accgacaaga caggttatgt tgaagtctgc gaccttccag | 1920 |
| tagtgattgc caggccattg gatattggcg caaaaaaatt agtctagact aggctttcga | 1980 |
| agctgctttg accattaagg ttggagtagc tttttcattt gcaagtaaat cattacggct | 2040 |
| tgtgtatacg gtatacaaaa tggagaaaac gctgactagt ttataaatca ttgagactta | 2100 |
| acggccggat aaatgctgat ctgattatag aaataacaac aaaaaggcca cgctaaaaat | 2160 |
| catattaatt ataatcggga aatttattaa taatattcaa gaaaaataaa aaccgtgggt | 2220 |
| acattattta aaa | 2233 |

<210> SEQ ID NO 15
<211> LENGTH: 5866
<212> TYPE: DNA
<213> ORGANISM: Lactobacillus paracasei

<400> SEQUENCE: 15

| | |
|---|---:|
| tttgaaacta agacgaaagc tgccatgtca acaaagccg ccataaatgc cactgtcaca | 60 |
| gatccatcag ccgcaatgcc agcatcttgc tgaagttctt taacagcatt aagggtgtta | 120 |
| ttcgtgaact cattattaaa gtctactgga ctaatcccctt tgcaccagaa agccccttga | 180 |
| atgagttgag caatgttccc cttatatcct ggcttcagac tacctacaac aggtgctaag | 240 |
| gcgttttgg tcgtctcgcc aaagccttca ccaatagcac taataccgat ttcgtgctgt | 300 |
| aatcccattc ttaggctata aattgttggc catcccgttt gcccgttttc tggagctgcg | 360 |
| acaaagccag gaacgctacc atacgttttg ttgagccatt tttgaacggc tcgtactgct | 420 |
| tcatctgcca ttttaaagtc tccttttttg ttttagacag cacgtctgcc gtcacaaaaa | 480 |
| gcaaacatat gttcggattc atttcatctc ttcaaagctt cgaaaggcaa ccctgatcca | 540 |
| caaataatcc ttttattttg aacttagcaa aaaaatgagg ccctcacata gtgttgaagt | 600 |
| tgcctcattc ttaatgtcta tatttaaagt attgccacaa cgatggatca tcgaacgctc | 660 |
| atggacttgg ttagacatgt atcgacgact atgaaaatgt gggcgcaagc tcaatttcac | 720 |
| cttccaaatg tttgtgctat ctcatttagc gctggttttt ttaggataga ctagacaagg | 780 |
| actaataatt tctcaagaat cccgcaactc cactattcat tcgtcgaaat ccccactgat | 840 |
| actcttgtcc ttgcacgttc gaccaagcaa gaatgtttat tccgataacc gaattgttgc | 900 |
| catcaagtaa tggacctccc gacatgccat gatacgaatt aatttgttgt gaaatatata | 960 |
| ttcctagtgg gtcctctgaa aagggtgtga cagtcccact tgattgaacc atgactcctt | 1020 |
| gaagttcgta ccctgattgc ggatcgccag ggaatccaat ggatcttgct gccatcgtat | 1080 |
| cagcagggtt cgtatttaaa ttaagacccg caggcatact accagacttc atagagacaa | 1140 |
| ttgcagcccc gtaatcattc gaagtagctg ttgaattatt aatccatgcc tgtggcacta | 1200 |
| tcaatctatt caatactccg taaccgaccc ttgatgatt tgcttgacta tcaccaaagt | 1260 |
| taataattcc tccagaaata taatgaccat catataacat gtgtgctgct gtccctatac | 1320 |
| ggtctactcc aatgctaaat ccagtaccgc cagaagttcc actgctcagc tctgtgccat | 1380 |
| ttgagttaga gatgattttt ttatacgaac tgtcaaggta tggtgagtta atgaccatga | 1440 |
| caccatttgc catcgaaaac cacgtgctca aaaccccaac ggaactgtac ggcgccgaat | 1500 |
| tggggtttga cacaggtgat accgtcctca cagatagatg attagacgat ttattcagtt | 1560 |
| tcgcaagata ttcggacgta attccttgaa cttctttcc ttcttttaaa tcctgatatt | 1620 |

```
gatcaggtgt ataagctttg acactccctt taaaatcggg ataagaatac tgatattgtc    1680
gaatgatttc attcaaaaac tgttgtgttg tcgtctggtt agtcaaaaca atatcattct    1740
ttggtaaaac atggctattc gctgccaaag gatttgccat actatcagca cttacactta    1800
ccgtttgaac ttgaattatc gctaaggctg cagctatcat agtgatatat gcccatactt    1860
ttcgcaattt aattccccct ttttcttaaa atgaaaccgc attcacggag cttgtcaat     1920 gcttttaaaa acaaacgtt actttttggct catcttggct gtcagcataa ttggagtaat    1980
tgttcttgcg gtgttatggc gcatgaaccc tgaaggaacg gcctcaaata agtttgaacg    2040
tcccaccatt actattaaaa aagtcaaact tattaagcac agtaacagta ttgctgtcac    2100
atttgctacc tctccaaaaa gcaaatatac gataagtgat cttaaagaga atcaactttc    2160
ttctggcatt tcgaataaaa gagaaaatac cgtttcggaa ttaaagcccct cctcctctaa   2220 gcttgcaata cgggttaagc ataacaataa tatacaaacc aaagtggttt ctgttcccat    2280
tggttatcat attatgaaaa gtgccatttc aagaaagcca attcctatgg gagaagagtt    2340
taagtacaat ggaaagtcgc atgttttatt tagcatgacc attaccccta aaaaacaaaa    2400
caagaacagt ataaaaaaca ccactgcttt taacataacg gttaaaaatg atcactacct    2460
tgtccctgtc gtattagata ccaaatacct tactgtttct gattcagaag gtaactcatt    2520
aaaagtaaag ccattctcaa aaatttctat tccagcaaaa aagaaaaaga ccattgcaat    2580
aactattgag ggcgttcccg caagctctgc caatggtcta gttataacgt ataatactgt    2640
cgatttagac ttaccaatct cctttataaa ttcctgaaat tacactaact gtcccccacc    2700
ttgacagtca gtacactcaa actgtctctt atgcttacaa acacgtaatt taggcggttt    2760
ttaagcaaaa gtcgttagtt ttcataaatg ttatcttata ctctaatgag atctagcttg    2820
tgataataag gctgtttttc tttgacagcc ttattaagca cactaatcaa tgtcaattcg    2880 aagttttttgg tttcctactt ggccaacttt gttatcagaa attccaaaac tcattgcctc    2940
ccgccaccat atatttatcg agccattttg aaaatgaaaa atcgaaatat cggtctgctt    3000
ctattccggg atgagttaga tatgattttc ctaaccgata cttctctata tcaatataca    3060
tatctccgac atcccttata tggagaatgg gtactttatt tacaaaactt ttaggcagtg    3120
cctctttttc tttaatcatt tttctaattg aatagacttc acacgtatat cccataggaa    3180
tcccttcgat tgttgtgtca aataaaaata gtccattagt aatcgagaga aactcaatgt    3240
aatcctgtgg aaggttccac ctttttattt tttctatatc atcagcgtgt gcaggaggtt    3300
ctatcttaaa agaaacattt tgcacatctc catctaattg gaatgttgag agcgcttttt    3360
ccccattttt cgtcaccttt attaaagaat taattcttcg ccgaattaga gattccaaat    3420
gagttcctcc tcaatagttg ttaaaccacg cggtgatcaa ccgatgattt ggtgttaaca    3480
ccggcatcaa attattaaag tcatttgttc cgccataaac tctcgggcga atatgatgca    3540
cttctcgaga actccaaaaa tctgcagatt gattgccata tgtttcactg aacgttttaa    3600
tataaatata tctatctttt gatgaccaac taggagattt tgataactta gtccaggtag    3660
tattaatagg tgtttctgca tcttttttag acacgggatc aacatattca gggaaattct    3720
gtcctatttt attttgtaaa tagatggccg ttggtgggat tggttttaca ttagccgctc    3780
cattaactcc tataaatcca acagcgccag caacgttaaa aaatgtggtt ttggctggca    3840
attctgtaaa accaagtaat cctgtttgca aaccgcctat tttgctaatg ggtgccagcg    3900
tattggcatt caccggacct gcaagggtag gctcagtatt aaattcaatt tgcacatcaa    3960
ctgcggctgg cgggacaccc tcaatagaat caatccagaa attgactctg aatttttccgg   4020
```

```
atatgtattc ttccgataag tgccaggtaa tatttgtaac aggaacttct gcacgagaac    4080
ttatgccatt gccatgacta ttattcagta ccacttgttt tccagaagcg ataattggtt    4140
gtccattttc tggattactt cttgataact tgtcagcatt ggtcagttga gtattgttat    4200
cgctaatacg gctttcagtt gaaacaattt gatttaaaga ttgtgttgtg tctgcggata    4260
caattgttga atacccaagc aaattgacta gaaagagccc gaatattagc ccaataactt    4320 tccactttt cacgcctatt atcttctttc caaagttctt cagtgcctgg caataactgt    4380
atacattgag cagtatagtc gctatttat agctgaacaa ctcataaagc tcaattatta    4440
ttagcctata aaaccactgc ctaagtgaat tgatctagaa cgaagcacgc cgaagaagtc    4500
gctaaatgtg ctaagaaaaa tgtgcttgaa tagctcaaaa gtaattagcg tctccattga    4560
aaatccgtta tttttaagtg atctagtgtt aactatgaat cccaaataaa aagcaaaatc    4620
cgtaaatgcc aaattttcct ttttgacgtt tttctactgt cgcgagattt gcaagtgtac    4680
gtacacttac gatgaattga cagaatctca gctgcgctga tcgtcaattt tgtttggggg    4740
cacgccccca atcccctgt tattttgaag ggaggtgagt ccccccttcaa aatcaaaatt    4800 taaacagcat ctgccgccat cttttcgctg accttctcac gatgttacac gtggtgttga    4860
cacccacttg catttagagt ttcattcaag ttgaacattg tgtaatatat gagttgcatt    4920
tgataaacat atcagttgct atttgtgcaa ctttaaagct tcggctaatt caacgttctg    4980
ttaatttaca agcatctcga cagtttctgt taaagcaaca tctacgcttc aattcgagca    5040
actcactata cgtatgccga gttgcagaca agctactata tagctgtacg cgctgaaaca    5100
ccaaaaatcg ttcgtttatg cccaataagc gaataatctt gctcaggtgt agtaaaaaac    5160
tgtttacgtg tagtgaatgg cgctagcccct tgtcgtaact ggcatcatcc acgtgtagta    5220
aaacgcgttt tactacacgt tcgtaatttt ttcacgtgga gtaaatggcg ttttactaca    5280
ccttttgacc ccaacgtgct atcacgacaa accaaaccgc actgcggttt accccaattt    5340
tggggtcagt tttgccttat gctctttcat gattttaggc gcgttccaag cagtctcaaa    5400
aagtggtcga tccaggcgag ccgatttttg agaaggattg gatagcaact caatttattt    5460
tgatcttttg cttggagaaa aacgttcacg ttttgaccag ggccgtcgca actgttgacc    5520
aaaactcgtc cggtaacgtg acgctatta aacgccgcgt tggtttgcta gacgaccatt    5580
catcatcacc attcaggagg tttttgaaat gacaaagcaa gacgaaacac accgggtcat    5640
gttcactttg accgatcagg cgattgcaaa attgaatcag ctggtcgcaa aaaagcaaca    5700
ggaagtgaat caaaatccgg aactggctaa gtaccatgtc agcgtgacca aatcaaatat    5760
cattgaggac tggttatcaa agcagtgagt ttaaaaagcg ctaaagggcc tgtactagcg    5820
tttcttactc tggtgggtat aattaatgct ctctacatca aaaacg             5866
```

<210> SEQ ID NO 16
<211> LENGTH: 11007
<212> TYPE: DNA
<213> ORGANISM: Lactobacillus paracasei

<400> SEQUENCE: 16

```
gccacgaacc tgtagccgtt tggatgaagc catataatac tggaccaacc gccgcaaata     60
agtagccgac actttgagca aaatcaggaa tactaatcta ctttgcccctt aaaaaatctt    120 gagatgatcc atatcttgtt ttgccttcat tactgtagtt ggtcataaga agtgccctac    180
attcattaga ttacttgtct aataattgta gggcacttgg gttgagaaaa atgatgttaa    240
```

-continued

```
ctaagaatgc aaacgaacta aaatctttgc ttgcttttta tcctttttcta aggattcaat    300
tccttctgaa actaattcat ttaattcaat cttttttgta atgacctgtt tgaatagtga    360
acgatgggta tctataatct taattactcg atcgaagata ttggcatatc cataagatgt    420
taataaacta ccaccttttt taagaagagc tctaacatct acaactggtg gatgttgaaa    480
taatgcaatc acggtaacct tgccaccatt tttaagagcc tgaatggcac cagtaagtgt    540
gggttgtaca ccggcgcaat caaacgcaat atccactccc tgattttccg tgatagtgct    600
gatagcgtga gctaatgact tttgactatc agcacgtatt gggtattgaa ttcctaattc    660
atttgctaaa ttcaaacgtt cctctgacat gtcatttatt atgacgtgat gtgcaccaga    720
aatttgtgct attaaggccg tgaacaatcc aattggacca gcaccttgaa ttaaaacatc    780
atctccagga gacactcggc ttgccataac tgcctgtgca gcaactgaaa ctggttcaac    840
taaggcccct aaatcaagcg gaaagctagc tggtaagaga tgtgcaaagg tacttttttac    900
attgcacttt tcagctaagc caccgttagc cgaaaatcct aagaatcctg ctgattgatc    960
actacctata gcatgttcac accaattata atgaccagaa agacattccg gacattttcc   1020
acaagcaatc attggttcga ctgcaacttt atctccaatt cttaatttag atacttgttt   1080
tccaattttta gaaatcgtcc cagaaaattc atgaccagga attagcgggg cttgcatatg   1140
ggttagcgga tgaggtattg tcgccaaatc catccctct aaatattcat gaatgtcact    1200
accgcaaata ccattaaatg caacctcaat ttgaacttca tctggtgcgg gatcaggaat   1260
atttcttttt tcaaagcgga tatccttagg accgtaaata acagctgcct tcaccatagt   1320
catagtgctt cgcttccttc atgttcaata tagcacaatc gtatataaaa tagtgaatag   1380
atttcagtaa tgaagttacc atcttgactt aacaaaaact tgctaactga ttatatgaga   1440
aactttttact tgaaacattt ttggtgatta ccattaattc cctcggacat attttgaaaa   1500
accctatttg atgctgattg caaattattt tatgcgtatt tattaagggt ttctatgttg   1560
aagtatatag caaacttgtt caagtaactg acttttcacgt gggctttagc caagagatgc   1620
tgagcagcga acccaagggg tgttactcgc ccacgcaaaa aagaaatcca attgcattcc   1680
agtatgagcg agaagcaagc cattaagacg ctgattcatg aactcgcgca cagtgaatta   1740
cattgtgatc cgaagttaaa attggatcgt tcaaccatgg aattggaagc tgaaagtacc   1800
gcgtttatcg tttgtcaaca tttgggaatt gacacgagtg attatacgtt tccttacctt   1860
gctgtttggt cgaaagataa ggatctttcc cagctctcca aaagcttaac gcgtatccaa   1920
tccaccgtcg aaaaattcaa taaaaccgtc gatcaaaacc ttgaaaagat tcgtgagaaa   1980
ccgttgacgc ttgatcaaaa aatagaacgc gctaaaacca ttgcgacaac ggaaaacatc   2040
gcaaaaaaag agcaagggct ggtgcaagca acgcaggaga aaacacgcta acccatttgt   2100
tgaatactct cactcaagag gacactccag cccttgatca cccaagaaag gaattaccaa   2160
catgaaaacc attgacgaaa tgaacgaatt cgatcgtgac attatcttac ttcaccgcaa   2220
gtctgtgagc gaagatacac cgcaggcaat tcttgtgaaa gtgaaacaga ttcgtaacgc   2280
aattgccgac gaaaaggcgg gtaaagaaga tccaattgag aaagaattta cactcgaatg   2340
ttacgacgaa gcaatcagaa aactaaggga ccttcggtc gctgattatc agttgtggtt   2400
gcgtcaaaac aaagacctgg aagggtttga attttgattt tgaagggtgt cgtagaccc    2460
ttcaaaataa cggggggattg ggggcgtgcc cccaaaacaa aattgactat cagcggagct   2520
gatattggat caatttatcg caagtggacg tccacttgca aatctcgcga cagtagaaaa   2580
agccccagaa aagcaaatct gaaaaaatgt aacaggcact tgatatcaag tgccttattg   2640
```

```
tttctaggat cgctaaaaat aacaggaggt ggttacatga agcaatctga tgaacaccgc    2700
acgcgttcag tgagaagcac tgtgcgtatg accccagagg agcgtgcttg ggttgatatg    2760
agaagagcct ctgtcggcaa tccaaagttc aatgcatttg cctgtcgcgc actcacgacg    2820
agcaagatcg ttcatgtaca ttttactgat actaaaaagt tacttagaca gctgtcaaga    2880
attgggaata aggctcctat gctgtaatta cggacaaaaa tagtttgtgc gataattaca    2940
gcataagggc ctctaggtcg agcccagga ggcggagacc gccgcacagc caacccccac     3000
gccgaaccgg aggccagccc gcccgcaccg cggccgcaat catccaccca acgcccccca    3060
agtttttgat agcggtaaca acgcctgtgc gcttgtcgtg gccggccttt tttcataagg    3120
ttggaggaga aaggaagggt ggttatgggc gcttggtatg aacacgcaat tatttaccaa    3180
atctatccaa aatcgtttca agacagcaac ggcgacggca tcggggacct gaacgggatc    3240
cggcaacgga tcccgtacct gcaagccctc ggcatcaaca cggtgtggct gaacccgatc    3300
ttcgtctccc cacaggtgga taacggctac gatgttgcca attacttcgc cgtggacgaa    3360
accatgggta cgatggccga cctggaggcg ctgatcgcgg ctctgcacgc ggccggcatc    3420
cgtctgatca tggactttgt gctaaaccac acctcggatc agcacccgtg gttccaggac    3480
gccattcacg ccaaaaatag tctgtaccgc gactactaca ttttctctgg ccacgacggg    3540
cagctgccaa acaactgggg cagcttcttc ggcggatcgg tttgggcgcc ggatccggcg    3600
ggaaccgggc agtcgtattt tcatctgttc gaccggcgga tgccggatct gaactgggcc    3660
aatcccgagg tgcggcgggc gatgggagac gtcgccacgt tctggctcgg caagggcatc    3720
gacggactgc ggctggatgc cttcatccac attgccaagg ccgatctggg gcaggattac    3780 ccctggctc cggggcagca gacgccggtg gtggcggagc cgttttctc caacctcccg      3840 aaggtgcagg aatggctgcg gccgttctgc gaccggatca aaaccgacta ccccgacgcg    3900
tttctgctcg gcgaggcggc atcggccaac gttaacctgg cggcggatta caccgcgcct    3960
agccagcacc tgatggacag cgtgatcacg ttccgctact tcaccgagga cgaaagcggc    4020
ctggatccgc ggctgccggc gcagtaccag ccgcggacgc tggatttccc ggcgttcaag    4080
caaacccagg cggtgtggca gcagaccctc gccggggtgt cgatgccgac gctgtactgg    4140
ggcaaccacg acatgccccg gctggcgacg cgggtggcca aaaccaccac ccaggcgcgc    4200
agtctggcca tgctgatgta cctgcagcgc ggcctgccgg tgatctacta tggcgaggag    4260
ctcgggctac acaacctgca gttcgatcac gttgatcagt ttgcggacgt ttcggtggcg    4320
ccgttcgtgg ccgcgtcga ggccaccggg cagtcgcgga gcgcggcgct ggccatggtg      4380
tcggcgacgc acaaactgcc ggcacggggg ccgatgcctt ggacgaccgg gttgcaccag    4440
ggcttttcca atcacctgcc gtggctggtt gggcgcagcg aggacgtgac cagcgtggcc    4500
gcgcagcagg ccgatgaggc cagcatgctg cacttctacc aagcgctgat tgccctgaag    4560
aagcagccgc tgtttcaggc cgggcattac cggctgctga cgacggcgcc gaacctgtac    4620
gtctacgaac gcacgctggc cagccggcgg gccctggtgg cggtggcctt ggatgagcaa    4680
ggcgccacct tcaccgtgcc tgaaggcctg acgaccgtgg cgctggccgc cggcgattac    4740
caactcgaag gtcaaacgct cacgcttggc gcgaacgccg cgtggtgtt aaacgaaagg      4800 ggaactcgat aaccatgcaa cttgcagcat tacggcaccg cccagaaagc gaagattgtt    4860
ttttgtacac tccagatgag ctgcggctgc ggctccacac agccaaggcc gacgtgcagg    4920
cggtcatcgt actgtacggg gatccgtatg tcaccgcgcc gaacccgacc accggagaac    4980
```

```
cggaattcgc ctaccaagag gcggcgatga tcaaaaccgg caccggccaa accagcgact    5040
actggaccat cagcctgacc gcgccttatc accgcctgca gtaccagttc ctggtgaccg    5100
gtcaggacgg caacaccgtc ctgctcggcg accgcggctt gcgggccgac agcgccgcca    5160
accgccgggc cgatctgttc cgggtgccgt acttccacgc catcgacacg gtacagacgc    5220
cggcctgggt caaggaaacc gtgtggtacc agatattccc ggaacgcttc gccaacgggg    5280
acaagacgaa cgaccccaag ggcaccaagc cttggcgtcc ggcggatcac ccgggccgtg    5340
aggattacta cggtggcgac ttgcaagggg tgctggacca cctggacgac ctgcaggcgc    5400
tcggcgtgaa cgggctgtac ttctgcccgg tgttcacggc gatgtcgaat cacaagtacg    5460
acaccatcga ctacttcaac atcgaccctg cgtttggcga caaggccttg ttcgccgatc    5520
tggtcaacca gcgcaccgc cgcggcatgc gggtgatgct ggacgctgtg ttcaaccaca    5580
tgggcagccg cagcatgcag tggcaagacg tgctgaagtt cggtccgcag tcgcgcttcg    5640
cctcctggtt ccacatcaac cgttttccgg cggcgccctt cgccgcgccg aacagggcg    5700 gcgtgccgca gtacgacacc ttcgccttcg aaccgcacat gccgaagctc gacaccagca    5760 acccggcgt gcaggactac ctgcttgagg tggcgacgta ctggatcaaa cagttcgaca    5820
tcgacgcctg gcggctggat gtggccaacg aggtggacca tcacttctgg aaacggttca    5880
atcaggcaac caaagcgctc aagcccgatt tcttcgtgct gggcgaggtc tggcactcca    5940
gccagccgtg gcttaacggg gatgagttcg atggggtcat gaactacgcg ttcaccgagc    6000
agatcgaggc ccacttcctg accggcaagc tgagtgctcc tgagctgacg gcggcgctga    6060
cggatcagct gatgctgtac cgcgaccaaa ccgaccaggc gatgctgaac atgctggact    6120
cgcatgacac cgcgcggctg ctaacggtgg ccggcggcga cgaggacctg gccctgcagg    6180
cgctggcctt caccttcctg caaaccggga tgccgtgcct gtactatggc acggaaatgg    6240
gcatggccgg agaaaacgat cccgactgcc ggcggccaat ggactgggcc cagctgaagg    6300
gcccgatttg gcagcgtgtg caggcccttg tgaccttccg ccgcgcccag tcggcaacgc    6360
taggcaccgg caccacggcg ctgagcgtga ccgcagccgg gctgcttaag gtaacccgca    6420
caggtgagca caccgtgacg gcgtatttta acaccaccaa gcagatggcg cactgaccg    6480 tcagtccatt actggcgcag ggttacgccg ccagcggct ggcgccaacc gggtttgctg    6540
ttatggttca gtaagattat gttagcggta acaggcaatt tgacccttta aaagcgtttt    6600
catattatca taatcaaaag tgtagaaaag ttcaggtggc gcaattcacc tcccgaaagt    6660
gaaggatgca agatgaaacg gatatttgaa atcgacccgt ggctggtgca aagccaccaa    6720
ttgaacccca acgagaaacg cctgcaggaa agcatgaccg ccatcggcaa cggctacatg    6780
ggtctgcgcg gtaacttcga agaaggttac agcggtgatc acctgcaagg cacgtacctc    6840
ggcggcgtct ggttcccaga taaaaccgtc gtcggttggt ggaaaaacgg ctacccggat    6900
tacttcggca aggcgatcaa cgcgccgagc ttcatcggca tggcgctcac cgtgaacggc    6960
gagcgcgtcg atctggccac cagcgtctac cgcgattca ccctcacgct tgacctgcac    7020
cagggcctgc tgacccggag cttcgtgttc gagggcaaaa aggccacggt gcgcttcacc    7080
ttcaagcgtt tcctcagcaa cgtaatcaag gaggcggcgc tggtgcagct caccgccgaa    7140
agccttgtcg gaccggccga gctgacggtg ccgcacagc tcgacggcaa cgtcacgaac    7200
gaggacagca actacgacga gcgcttctgg gcaccgcagg ggaaaacgcg cgcggcaggc    7260
accatccagc tgcagaccaa gcccaacccg ttcggggtcc cgcagttcac ggtgctgctc    7320
aagcaaagcc tgcgccaagg ggcaacccctt ttacccggca ccgtgaccac cagcaccggc    7380
```

```
cagctgacca gcacggtcac gctgccgctg gcgccaaacg tgccggtcca gctggaaaag   7440
gacgtcatcg tggtcacgag ccgcgacgtc gccctgagg cccaggccga agcggccgcg    7500
gagctgatga cacagctgca gggccaaagc tttgcggccc agctggcggc acacaccgcc   7560
ctgtgggcca agcgctgggc ccaaagcgac gtggtgattg aaggcgacga cgcggcccag   7620
caggggatcc gcttcaacct cgcccagctg ttcatgacct attacggcga cgataagcgg   7680
ctcaacgtgg ggccgaaggg tttcaccggc gagaagtacg gcggggcgac ctactgggac   7740
accgaggcgt acgtggtgcc gatgtacgtc gccgccaccc ctccggccgt gacccgggca   7800
ctgctgcagt accggcacga ccagctgccc ggcgcctacc acaacgccca gcagcagggg   7860
ctcaaagggg ccttgttccc gatggtgacc ttcaacggca tcgagtgcca caatgaatgg   7920
gaaatcacct tcgaggagct gcaccgtaac gcagcggtcg ccttcgcgat ttaccagtac   7980
acggcctaca ccggcgatga agctacgtc aaccacgacg gcatggaggt gctggtgggc    8040
atcagccgct tctgggcgga ccgggtccac ttctccaagc gcgccggcaa gtacatgatc   8100
cacggcgtca ccgggccgaa cgagtacgaa aacaacgtca caacaactg gtacaccaac    8160 acgatggccg cctggtgcct ggagtacacg ctggcccggc tgccgaaggc cgatgccgcc   8220
attcaggcca agctggccgt gagcgccgcc gagcagcgcc agtggcagga cattatcgac   8280
cacatgtact atccggagga caagaagctg ggcatcttcg tccagcacga caccttcctg   8340
gataaggacc tgcggccggc aagctcgatt ccggccgacc agcggccaat caaccagcac   8400
tggtcctggg accgaatcct gcggtcgccg ttcatcaagc aggcggatgt gctccagggc   8460
ctgtacttcc tgaacaatcg cttcacccgc gagcagaagg aacgcaattt tgacttctac   8520
gagccgctga cggtgcacga aagctcgctg agtgcctcga ttcacgcggt gctggccgcc   8580
gagctcggta agcaggataa ggccgttgaa ctctatcagc gtacggctcg tctggacctg   8640
gacaactaca acaacgatac ggcagacggt ctgcacatca cctcgatgac cggcggctgg   8700
ctggctatcg tgcagggctt cgccggcatg cgctacgacc acgatcagct gcggttcgat   8760
ccgttcctgc cgaagcagtg gcagggttac cagttccgca tcaactaccg cggccgggtg   8820
atccaggtcg cggtggggaa aaccgttgca gtgaccctgc tggccggccc gccgctgacc   8880
gtcatggttg ccggccagcc gcagcatttg gaggtgagcg cgcatgctta aaggattgct   8940
gttcgacctc gacggcgtct tgaccgactc ggccaagttc cacctgcagg cctggagcca   9000
gctggccacc cagctgggca tcaccctgac gccggccgag cgcgaaggcc tgcgcggccg   9060
ctcgcggctg gactcgctga acctgatttt ggcggcaggc gcccaggaag accggttcag   9120
tgccgcagag aaaacggcgc taaccgacca gaagaacgcg gtgtacctga agctgattca   9180
gacgatgacg ccggtggaca tcctgccggg cattccgcaa ctgctgaagg acgcgcaggc   9240
ggccggcctg aaaatggcaa tcgcctcggc gtcgcggaac gccccgacaa ttcttgacca   9300
cctgggcctg gccgccagtt tcgacgccat cgtcgatccg gcgaccctgc accgcggcaa   9360
gcccgacccg gagatctacc agcaggcgca agcgctgctg gggctccagg ccgccgaggt   9420
gatcggcttc gaggatgcct cggccggggt cgccgccatc aaagcggccg gtcagttcgc   9480
ggttggcatc ggggatgccc ggcttctggc cgcagcggat tacctagtga aagacacggc   9540
ggccctgcag ctgagccagt tgcaagcggc gttcgccaaa gaaagtgggg agactaatgg   9600
ttgaaatcga cttggaccac ctctacaaga agtacgacga cggcgaggat tactcggtgg   9660
tggacttcga ccttcacatc aaggataagg agttcatcgt gttcgtcggc ccctcgggct   9720
```

```
gcgggaagtc caccacgctg cgtatgattg cggggctgga ggacattacc aaaggcgagc    9780
tgaaaatcga cgataaggtg atgaacgacg tggcccccaa ggaccgcaac atcgccatgg    9840
tgtttcagaa ctacgccttg tacccgcaca tgtcagtgta cgacaacatg gcgttcggcc    9900
taaagctacg gcactacaag aaggaggaca tcgacaaacg cgtgcaaaac gcggcggaga    9960
tcctcggcct gaagccgttt ctcgaccgga agccggccgc cttgtccggg ggccagcggc   10020
agcgggtggc cttgggccgg ccatcgtccc gcgacgcccc aattttcctg atggatgagc   10080
cgttgtcgaa cctggacgcg aagctgcggg tgtccatgcg ggcggaaatc gccaagctcc   10140
accagcgcct gaacaccacc acgatttacg tgacccacga ccaaaccgag gccatgacta   10200
tggccgaccg ggttgtcgtc atgtccgttg gccacgtgca gcagattggc accccggccg   10260
agatttacca gaaccgcgg aaccagttcg tggccgggtt catcgggtcg ccggcgatga   10320
acttcttcaa catgacctac caggacggct tcgtcagcga cggccaaagc attcgcctca   10380
aagtgccgga aggccgggcg aagattctgg acgaccaagg gtacaacggc aaggaagtcg   10440
tgttcggcat ccgccggag gacatccatt cggaggaggc cttcctggag acctggccgg   10500
acgcggttat cagctcaacc gtgtcggtgt cagagctcct gggcgccacc gagcagcttt   10560
acctgaaggc ggatgacacc gagtacgttg ccaacgtcaa cgcgcgcgac ttccacaatc   10620
ccggggatca tgtgaaaatg ggcttcgacg tcaacaaggc gcacttcttc aacaaggaca   10680
cgaccatggc catcgtggct aagccgattc cgctggaagg ctgaggaggt gagtgcatga   10740
ccccatggtg gcagcaagcc gtcatttacc agatctaccc gaagagtttt caggacagca   10800
acggggatgg catcggcgat ttgccgggga ttaccagtcg ccttgattac cttaagcggc   10860
tgggcgtcga tgcccttttgg ctgagcccag tgtatgtgtc gcccggcgag gacaacggct   10920
acgacatcgc ggactacgag gccatcgatc cccagttcgg gacgatggcc gacatggacg   10980
ccttgatcgc cgccgccaag cagcgcg                                       11007

<210> SEQ ID NO 17
<211> LENGTH: 977
<212> TYPE: DNA
<213> ORGANISM: Lactobacillus paracasei

<400> SEQUENCE: 17
cccgcgattt tggcgtgatt ggcttcgacg gggtattcct ggaccaggtg tccaaccccca    60
agctgaccac ggtgaagcag cccgtgcagc gcctcggcga actgctggcc cgcatgctcc   120
tgcagaaggt ggcacagtcc ggcgcccaac aggggagct gctggtcgat cctgagctga   180
ttgctcggga cacgacgcga agtagatcg gatttcaact gtccttaccg ctatggtagg   240
gccagttttt aggctctatg tcaaatctaa ttcatagcta atagttgatt tggcaacgcc   300
taaggcgtca gccatatctt ggtaagtatg atggccttca ctgaccagtt gagctagcgc   360
accacgttga aaacgtgata agtagaagt acccaaagta atcactcctt atagctggtt   420
ggaattaact actccattgt aagagattgc tttgggcctt tttttatttt tgttcggatt   480
aattatagaa tttgtctaat tagttgaaaa ttcttagggt tgcccatata tcttttagtc   540
tggtcattag tttttatgtt tgatctgctt ttttctgatc gcaaacaccc acaactgcga   600
gtgagtcctt tttgaagtcg ttgactgtca acaatacatt tatttccaca ttgacattga   660
cagagccaaa gcgcgttgcc attagaactg cttccaaaaa agctaataac tgtgagtcgc   720
ccaaacgttt gattagctaa atcgatacgc ttttgcatac taatcctccc gcttgataag   780
aaggtactta aatagttgct ttcaattgat ctaatcgcca ttggcaccat gaaataaagg   840
```

```
ctaattcgtc aatctttgga atgccatagg ttctagcata cgttaacttt tgagtggtga    900
gtagttgatc atagggttta ctaataatac caaccacaag gatatcgact ttttttgtcaa   960 tcccgttgac aggcttt                                                    977
```

<210> SEQ ID NO 18
<211> LENGTH: 1239
<212> TYPE: DNA
<213> ORGANISM: Lactobacillus paracasei

<400> SEQUENCE: 18

```
aaatacgcaa aagaacccga cgagagttaa gtctcatcgg gttctcagtc gtggatgaat    60
tagaagcatt gttagctgca taaccttcaa cataggatca atagctggtt agatggtcat    120
ctctcagact gtttgcacca gatccaggca aacgtgttta tatccttggt catactcagg    180
atagatgggc attgtgagtg caacaggact tagttgcttg tatgctaggc aatgttggcc    240
ttgatacaga ggatcactct gtttctgatc tggatgataa cctcgttttt ccatttcagg    300
acgctgtccc aataattgtt gccctgggag tttgtcgaat taagtcttgg tgccacaaac    360
acacgctacg gcttcttttc ttgcaaactg atcttagtat ttagggcagt tgcatgatta    420
cggaattgaa ccatttttata atgaatcgtc ttttctataa gtctatagaa agtgcaggta    480
atggcatttt ctccagatcg gattgtctaa tcaatttaat tgattttttt ggtgtgtttg    540
attatattgc ttttgcaaag gtacaatata ccttttctct gctgccttgc gagcagcgat    600
ggcatcctcc atatgaacat atacacgatt taggacaaga tggccttgaa agtacagcct    660
tgcgacccac ttttgagcag ttttatccca actaactccg ataacgccag atttgttatt    720
ggaccgttta gtgtagaag caactaaatt tgttcgatta attagttgaa aattcttggg     780
attgcccatg tattttttag tctggttatt agcttttatg tttgatctgc ttatttctga    840
tcgcaaacac ccacaactgc gagtgagtcc tttttgaagt cgttgactgt caacgataca    900
tttatttcca cattgacatt gacagagcca aagcgcgttt ccattagaac tgcttccaaa    960
aaaactaatg actgtgagtc gtccaaacgt ttgattggcc aaatcgatac gcttttgcat   1020
actaatctcc ccgtttgata agaaggtact taaagagttg ttttcaattg atctagtcgc   1080
cattggcacc atgaaataaa ggctaattcg tcaatctttg gaatgccata ggttctagca   1140
tacgttaact tttgagtggt aagtagttga tcataggggtt tgctaataat accaaccaca   1200
aggatatcga cattttttgtc aatcccgttg acaggtttt                           1239
```

<210> SEQ ID NO 19
<211> LENGTH: 7
<212> TYPE: PRT
<213> ORGANISM: Artificial Sequence
<220> FEATURE:
<223> OTHER INFORMATION: peptide

<400> SEQUENCE: 19

```
Pro Asp Leu Lys Asp Val Gly
1               5
```

<210> SEQ ID NO 20
<211> LENGTH: 9
<212> TYPE: PRT
<213> ORGANISM: Artificial Sequence
<220> FEATURE:
<223> OTHER INFORMATION: peptide

<400> SEQUENCE: 20

```
Leu Glu Ile His Leu Asn Ala Ala Gln
1               5

<210> SEQ ID NO 21
<211> LENGTH: 10
<212> TYPE: PRT
<213> ORGANISM: Artificial Sequence
<220> FEATURE:
<223> OTHER INFORMATION: peptide

<400> SEQUENCE: 21

Gly Thr Asn Phe Ala Thr Ile Glu Asn Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: peptide

<400> SEQUENCE: 22

Gly Thr Asp Thr Arg Ala Glu
1               5

<210> SEQ ID NO 23
<211> LENGTH: 7
<212> TYPE: PRT
<213> ORGANISM: Artificial Sequence
<220> FEATURE:
<223> OTHER INFORMATION: peptide

<400> SEQUENCE: 23

Gly Thr Asp Thr Arg Ala Glu
1               5

<210> SEQ ID NO 24
<211> LENGTH: 5
<212> TYPE: PRT
<213> ORGANISM: Artificial Sequence
<220> FEATURE:
<223> OTHER INFORMATION: peptide

<400> SEQUENCE: 24

Tyr Ile Asn Ala Met
1               5

<210> SEQ ID NO 25
<211> LENGTH: 4
<212> TYPE: PRT
<213> ORGANISM: Artificial Sequence
<220> FEATURE:
<223> OTHER INFORMATION: peptide

<400> SEQUENCE: 25

Phe Met Trp Gln
1

<210> SEQ ID NO 26
<211> LENGTH: 5
<212> TYPE: PRT
<213> ORGANISM: Artificial Sequence
<220> FEATURE:
<223> OTHER INFORMATION: peptide

<400> SEQUENCE: 26
```

```
His Leu Ile Gln Thr
1               5

<210> SEQ ID NO 27
<211> LENGTH: 9
<212> TYPE: PRT
<213> ORGANISM: Artificial Sequence
<220> FEATURE:
<223> OTHER INFORMATION: peptide

<400> SEQUENCE: 27

Thr Ala Phe Ala Ala Leu Thr Glu Leu
1               5

<210> SEQ ID NO 28
<211> LENGTH: 6
<212> TYPE: PRT
<213> ORGANISM: Artificial Sequence
<220> FEATURE:
<223> OTHER INFORMATION: peptide

<400> SEQUENCE: 28

Met Glu Ala Asn Met Leu
1               5

<210> SEQ ID NO 29
<211> LENGTH: 12
<212> TYPE: PRT
<213> ORGANISM: Artificial Sequence
<220> FEATURE:
<223> OTHER INFORMATION: peptide

<400> SEQUENCE: 29

Asn Asp Tyr Glu Lys Ile Ala Met Gly Leu Leu Ser
1               5                   10

<210> SEQ ID NO 30
<211> LENGTH: 8
<212> TYPE: PRT
<213> ORGANISM: Artificial Sequence
<220> FEATURE:
<223> OTHER INFORMATION: peptide

<400> SEQUENCE: 30

Phe Ile Pro Asp Leu Lys Asp Val
1               5

<210> SEQ ID NO 31
<211> LENGTH: 10
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (6)..(10)
<223> OTHER INFORMATION: Xaa can be any naturally occurring amino acid

<400> SEQUENCE: 31

Met Pro Thr Glu Gln Xaa Xaa Xaa Xaa Xaa
1               5                   10

<210> SEQ ID NO 32
<211> LENGTH: 7
<212> TYPE: PRT
<213> ORGANISM: Artificial Sequence
<220> FEATURE:
<223> OTHER INFORMATION: peptide
```

<400> SEQUENCE: 32

Pro Asp Leu Lys Asp Val Gly
1               5

<210> SEQ ID NO 33
<211> LENGTH: 7
<212> TYPE: PRT
<213> ORGANISM: Artificial Sequence
<220> FEATURE:
<223> OTHER INFORMATION: peptide

<400> SEQUENCE: 33

Pro Asp Leu Lys Asp Val Gly
1               5

<210> SEQ ID NO 34
<211> LENGTH: 12
<212> TYPE: PRT
<213> ORGANISM: Artificial Sequence
<220> FEATURE:
<223> OTHER INFORMATION: peptide

<400> SEQUENCE: 34

Asn Asp Tyr Glu Lys Ile Ala Met Gly Leu Leu Ser
1               5                   10

<210> SEQ ID NO 35
<211> LENGTH: 8
<212> TYPE: PRT
<213> ORGANISM: Artificial Sequence
<220> FEATURE:
<223> OTHER INFORMATION: peptide

<400> SEQUENCE: 35

Phe Ile Pro Asp Leu Lys Asp Val
1               5

<210> SEQ ID NO 36
<211> LENGTH: 10
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (6)..(10)
<223> OTHER INFORMATION: Xaa can be any naturally occurring amino acid

<400> SEQUENCE: 36

Met Pro Thr Glu Gln Xaa Xaa Xaa Xaa Xaa
1               5                   10

<210> SEQ ID NO 37
<211> LENGTH: 7
<212> TYPE: PRT
<213> ORGANISM: Artificial Sequence
<220> FEATURE:
<223> OTHER INFORMATION: peptide

<400> SEQUENCE: 37

Pro Asp Leu Lys Asp Val Gly
1               5

<210> SEQ ID NO 38
<211> LENGTH: 12
<212> TYPE: PRT

```
<213> ORGANISM: Artificial Sequence
<220> FEATURE:
<223> OTHER INFORMATION: peptide

<400> SEQUENCE: 38

Asn Asp Tyr Glu Lys Ile Ala Met Gly Leu Leu Ser
1               5                   10

<210> SEQ ID NO 39
<211> LENGTH: 8
<212> TYPE: PRT
<213> ORGANISM: Artificial Sequence
<220> FEATURE:
<223> OTHER INFORMATION: peptide

<400> SEQUENCE: 39

Phe Ile Pro Asp Leu Lys Asp Val
1               5

<210> SEQ ID NO 40
<211> LENGTH: 10
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (6)..(10)
<223> OTHER INFORMATION: Xaa can be any naturally occurring amino acid

<400> SEQUENCE: 40

Met Pro Thr Glu Gln Xaa Xaa Xaa Xaa Xaa
1               5                   10

<210> SEQ ID NO 41
<211> LENGTH: 8
<212> TYPE: PRT
<213> ORGANISM: Artificial Sequence
<220> FEATURE:
<223> OTHER INFORMATION: peptide

<400> SEQUENCE: 41

Lys Leu Thr Glu Ala Thr Val Met
1               5
```